(12) United States Patent
Chabria et al.

(10) Patent No.: US 11,649,268 B2
(45) Date of Patent: May 16, 2023

(54) FIBRONECTIN-BINDING PEPTIDES FOR USE IN TUMOR OR FIBROSIS DIAGNOSIS AND THERAPY

(71) Applicants: ETH ZURICH, Zurich (CH); PAUL SCHERRER INSTITUT, Villigen (CH)

(72) Inventors: Mamta Chabria, Zurich (CH); Alessandra Moscaroli, Zurich (CH); Simon Arnoldini, Zurich (CH); Samuel Hertig, San Francisco, CA (US); Viola Vogel, Baden (CH); Martin Behe, Gelterkinden (CH); Roger Schibli, Baden (CH)

(73) Assignees: ETH ZURICH, Zurich (CH); PAUL SCHERRER INSTITUT, Villigen PSI (CH)

( * ) Notice: Subject to any disclaimer, the term of this patent is extended or adjusted under 35 U.S.C. 154(b) by 388 days.

(21) Appl. No.: 16/309,805

(22) PCT Filed: Jun. 14, 2017

(86) PCT No.: PCT/EP2017/064543
§ 371 (c)(1),
(2) Date: Dec. 13, 2018

(87) PCT Pub. No.: WO2017/216223
PCT Pub. Date: Dec. 21, 2017

(65) Prior Publication Data
US 2020/0181211 A1 Jun. 11, 2020

(30) Foreign Application Priority Data
Jun. 16, 2016 (EP) .................................. 16174824

(51) Int. Cl.
| | | |
|---|---|---|
| C07K 14/435 | (2006.01) | |
| A61K 47/64 | (2017.01) | |
| A61K 47/54 | (2017.01) | |
| A61K 49/00 | (2006.01) | |
| A61K 49/14 | (2006.01) | |
| A61K 49/22 | (2006.01) | |
| A61K 51/04 | (2006.01) | |
| A61K 38/00 | (2006.01) | |

(52) U.S. Cl.
CPC .......... C07K 14/435 (2013.01); A61K 47/549 (2017.08); A61K 47/64 (2017.08); A61K 49/0056 (2013.01); A61K 49/14 (2013.01); A61K 49/221 (2013.01); A61K 51/0497 (2013.01); *A61K 38/00* (2013.01)

(58) Field of Classification Search
CPC .................................................... C07K 14/435
See application file for complete search history.

(56) References Cited

U.S. PATENT DOCUMENTS

| | | |
|---|---|---|
| 6,565,880 B2 | 5/2003 | Cappola et al. |
| 2003/0068340 A1 | 4/2003 | Cappola et al. |
| 2013/0190224 A1* | 7/2013 | Sottile .................. A61K 38/164 |
| | | 514/1.7 |
| 2015/0320825 A1 | 11/2015 | Watnick et al. |
| 2017/0252459 A1* | 9/2017 | Aguilar .................. C07K 14/78 |

FOREIGN PATENT DOCUMENTS

| | | |
|---|---|---|
| WO | WO 99/16892 * | 4/1999 |
| WO | WO 2003/049742 | 6/2003 |
| WO | WO 2005/116064 A2 * | 12/2005 |
| WO | WO 2007/128563 | 11/2007 |
| WO | WO 2011/097401 | 8/2011 |
| WO | WO 2012159164 * | 11/2012 |
| WO | WO 2013/192546 | 12/2013 |
| WO | WO 2013/192546 A1 * | 12/2013 |
| WO | WO 2015/048819 | 4/2015 |

(Continued)

OTHER PUBLICATIONS

Schennings et al, Microbial Pathogenesis, 1993; 15: 227-236 (Year: 1993).*

(Continued)

*Primary Examiner* — Gary B Nickol
*Assistant Examiner* — Lakia J Jackson-Tongue
(74) *Attorney, Agent, or Firm* — Bryan D. Zerhusen; Nicholas R. Herrel; Cantor Colburn LLP

(57) ABSTRACT

The present invention is directed to a composition comprising at least one fibronectin binding polypeptide (FnBP) linked to at least one diagnostic or therapeutic agent, a nucleic acid encoding a fusion polypeptide comprising at least one fibronectin binding polypeptide (FnBP) linked to at least one diagnostic or therapeutic polypeptide agent as well as a corresponding recombinant vector and host cell comprising such a nucleic acid and preferably expressing said fusion polypeptide. The invention also relates to a kit of parts comprising at least one fibronectin binding polypeptide (FnBP), at least one diagnostic or therapeutic agent, and optionally one or more chemical agents for linking the fibronectin binding polypeptide (FnBP) to the diagnostic or therapeutic agent. In addition, the present invention intends said composition, nucleic acid, vector, host cell and kit for use in the therapeutic or prophylactic treatment of a disease, preferably a disease associated with abnormal fibronectin accumulation such as cancer, fibrosis or immune diseases.

16 Claims, 9 Drawing Sheets
Specification includes a Sequence Listing.

(56) References Cited

FOREIGN PATENT DOCUMENTS

WO   WO 2015106226   *   7/2015

OTHER PUBLICATIONS

Lindmark et al., Infection and Immunity, 1996; 64(10): 3993-3999 (Year: 1996).*
Speziale et al., Cell, 2016; 8(12):1516 (Year: 2016).*
Mero et al., Methods Mol Biol, 2011; 751:95-129 (chapter 8; p. 107/602) (Year: 2011).*
Hou, Zhaohua et al. "Perspectives on RNA Interference in Immunopharmacology and Immunotherapy". RNA Interference, edited by Ibrokhim Abdurakhmonov, IntechOpen, 2016. 10.5772/61575 (Year: 2016).*
Hubo et al., Front. Immunol., 2013; 4(82):1-14 (Year: 2013).*
Altschul et al., Basic Local Alignment Search Tool, (1990) J. Mol. Biol., 215:403-410.
Bertrand et al., Cancer nanotechnology: The impact of passive and active targeting in the era of modern cancer biology, Advanced Drug Delivery Reviews 66, (2014): 2-25.
Cao et al., Phage-based molecular probes that discriminate force-induced structural states of fibronectin in vivo, PNAS, vol. 109, 19:7251-7256, May 8, 2015.
Carnemolla et al., A Tumor-associated Fibronectin Isoform Generated by Alternative Splicing of Messenger RNA Precursors, J. Cell Biol. 108(3): 1139-48 (1989).
Chabria et al., Stretching fibronectin fibres disrupts binding of bacterial adhesins by physically destroying an epitope, Nature Communications, 1:135, Dec. 12, 2010, 1-9.
Cicchelero, L., et al., Intratumoural interleukin 12 gene therapy stimulates the immune system and decreases angiogenesis in dogs with spontaneous cancer, (2016), Vet Comp Oncol, 15, 4, pp. 1187-1205.
D'Errico, G., et al., A current perspective on cancer immune therapy: step-by-step approach to constructing the magic bullet, (2017), Clin Transl Med 6(1): 3.
Datta, J., et al. Anti-HER2 CD4+ T-helper type 1 response is a novel immune correlate to pathologic response following neoadjuvant therapy in HER2-positive breast cancer (2015), Breast Cancer Res 17: 71.
Diesendruck, Y. and I. Benhar, Novel immune check point inhibiting antibodies in cancertherapy—Opportunities and challenges, (2017), Drug Resist Updates, 30: 39-47.
Edgar., MUSCLE: multiple sequence alignment with high accuracy and high throughput, (2004) Nucl. Acids Res. 32:5, 1792-1797.
Engvall E., et al. "Binding of soluble form of fibroblast surface protein, fibronectin, to collagen," Int. J. Cancer, vol. 20, No. 1, pp. 1-5, Jul. 1977.
Erler et al., Lysyl oxidase is essential for hypoxia-induced metastasisNature, Apr. 27, 2006, vol. 440, 1222-1226.
Fletcher et al., Lymph node fibroblastic reticular cells in health and disease, 2015 Nature Reviews Immunology, 15(6), 350-361.
Getts, D. R., et al., Harnessing nanoparticles for immune modulation, Trends in Immunology, 2015, 36(7), 419-427.
Gotthardt et al., Indication for Different Mechanisms of Kidney Uptake of Radiolabeled Peptides, Journal of Nuclear Medicine, vol. 48, No. 4, pp. 596-601, Apr. 2007.
Grivas, P., et al., Cancer vaccines at the age of immune checkpoint inhibitors: reasonable approach as combination therapy in advanced urothelial carcinoma?, (2017), Annals of Oncology, 28(4): 680-682.
Hertig et al., Engineering Mechanosensitive Multivalent Receptor-Ligand Interactions: Why the Nanolinker Regions of Bacterial Adhesins Matter, Nano Lett., 12, 5162-5168, Sep. 14, 2012.
Hruby, D. E., Vaccinia Virus Vectors: New Strategies for Producing Recombinant Vaccines, (1990) Vaccinia virus vectors: new strategies for producing recombinant vaccines, Clinical Microbiology Reviews, 3(2), 153-170.
Huang and Miller, A Time-Efficient, Linear-Space Local Similarity Algorithm, (1991) Adv. Appl. Math., 12:337-357.
Hull, E. E., et al., HDAC Inhibitors as Epigenetic Regulators of the Immune System: Impacts on Cancer Therapy and Inflammatory Diseases, (2016), Biomed Res Int 2016: 8797206.
Hynes, R. O., Extracellular matrix: not just pretty fibrils, (2009), Science 326(5957): 1216-1219.
Janakiram, M., et al., Immune checkpoint blockade in human cancer therapy: lung cancer and hematologic malignancies, (2016), Immunotherapy 8(7): 809-819.
Johnson-Buck et al., Super-Resolution Fingerprinting Detects Chemical Reactions and Idiosyncrasies of Single DNA Pegboards, (2013), Nano Letters, 13(2), 728-733.
Jungmann et al., Multiplexed 3D Cellular Super-Resolution Imaging with DNA-PAINT and Exchange-PAINT, (2014), Nat Methods 11(3): 313-318.
Katakowski, J. A., et al., Delivery of siRNAs to Dendritic Cells Using DEC205-Targeted Lipid Nanoparticles to Inhibit Immune Responses, (2016), Mol Ther 24(1): 146-155.
Kelley LA et al., The Phyre2 web portal for protein modelling, prediction and analysis, (2015) Nature Protocols 10, 845-858.
Larkin MA et al., Clustal W and Clustal X version 2.0, Bioinformatics, 23, 2947-2948, 2007.
Lau and Sun, Plant seeds as bioreactors for recombinant protein production, Biotechnol Adv., 27, May 18, 2009, 1015-1022.
Little, W.C., et al, "Assay to mechanically tune and optically probe fibrillar fibronectin conformations from fully relaxed to breakage," Matrix Biology, vol. 27, No. 5, pp. 451-461, Jun. 2008.
Marrone, K. A. and J. R. Brahmer, Immune Checkpoint Therapy in Non-Small Cell Lung Cancer, (2016), Cancer J 22(2): 81-91.
Meenan et al., The Tandem beta-zipper Model Defines High Affinity Fibronectiv-binding Repeats within *Staphylococcus aureus* FnBPA, J. Biol. Chem., vol. 282, No. 35, pp. 25893-25902, Jul. 2, 2007.
Notredame et al., T-Coffee: A Novel Method for Fast and Accurate Multiple Sequence Alignment, (2000) J of Mol. Biology, 302, 205-217.
Paolino, M. and J. M. Penninger, The Role of TAM Family Receptors in Immune Cell Function: Implications for Cancer Therapy, (2016), Cancers, 8, 97, 1-22.
Papaioannou, N. E., et al., Harnessing the immune system to improve cancer therapy, (2016), Ann Transl Med 4(14): 261.
Raab et al., Fluorescence Microscopy with 6 nm Resolution on DNA Origami, (2014), Chemphyschem 15(12): 2431-2435.
Schennings, T., et al., Immunization with Fibronectin Binding Protein from *Staphylococcus aureus* Protects Against Experimental Encocarditis in Rats, Microbial Pathogenesis, Academic Press Limited, New York, NY, US, vol. 15., No. 3, Jan. 1, 1993, 227-236.
Sievers F et al., Fast, scalable generation of high-quality protein multiple sequence alignments using Clustal Omega, (2011) Mol. Sys. Bio. 7: 539.
Swart, M., et al., Combination Approaches with Immune-Checkpoint Blockade in Cancer Therapy, (2016), Frontiers in Oncology, 6: 233.
Topalian, S. L., et al., Mechanism-driven biomarkers to guide immune checkpoint blockade in cancer therapy, (2016), Nat Rev Cancer 16(5): 275-287.
Viti et al., Increased Binding Affinity and Valence of Recombinant Antibody Fragments Lead to Improved Targeting of Tumoral Angiogenesis, Cancer Research, vol. 59, No. 2, pp. 347-352, Jan. 15, 1999.
Westers et al., Bacillus subtilis as cell factory for pharmaceutical proteins: a biotechnological approach to optimize the host organism, (2004) Biochimica et Biophysica Acta, vol. 1694, p. 299-310.
Wilhelm et al, Analysis of nanoparticle delivery to tumours, Nature Reviews Materials 1, (2016) 1-12.
Xia, B. and R. S. Herbst, Immune checkpoint therapy for non-smallcell lung cancer: an update, (2016), Immunotherapy 8(3): 279-298.
Yeku, O. and S. F. Slovin, Immune Therapy for Prostate Cancer, (2016), Cancer J 22(5): 334-341.
Zardi et al., Transformed human cells produce a new fibronectin isoform by preferential alternative splicing of a previously unobserved exon, Embo J. 6(8): 2337-42 (1987).

(56) References Cited

OTHER PUBLICATIONS

Zeglis et al., Optimization of a Pretargeted Strategy for the PET Imaging of Colorectal Carcinoma via the Modulation of Radioligand Pharmacokinetics, (2015), Molecular Pharmaceutics, 12(10): 3575-3587.

Zhao X.-K., Effect of Danshao Huaxian capsule on Gremlin and bone morphogenetic protein-7 expression in hepatic fibrosis in rats, World Journal of Gastroenterology 2014, 20, 14875-14883.

Zhong et al., The Anti-Fibrotic Effect of Bone Morphogenic Protein-7(BMP-7) on Liver Fibrosis, Int. J. of Medical Sciences 2013, 10, 441-450.

Zhou et al., Relaxin inhibits cardiac fibrosis and endothelial-mesenchymal transition via the Notch pathway, Drug Design, Development and Therapy 2015, 9, 4599-4611.

International Search Report and Written Opinion for PCT/EP2017/064543, dated Dec. 1, 2017 (with Corrected Cover Page).

Form PCT/ISA/206—from PCT/EP2017/064543, dated Aug. 17, 2017.

Response to Form PCT/ISA/206—from PCT/EP2017/064543, dated Sep. 13, 2017.

* cited by examiner

$^{111}$In-[FBP-NODAGA], mean IA%/g ± SD (N=4)

| Dissection time | 1h p.i. | 4h p.i. | 24h p.i. | 96h p.i. |
|---|---|---|---|---|
| Blood | 1.81 ± 0.62 | 0.48 ± 0.08 | 0.15 ± 0.008 | 0.06 ± 0.027 |
| Kidneys | 140.58 ± 18.10 | 130.66 ± 10.32 | 92.36 ± 14.25 | 39.69 ± 4.79 |
| Liver | 7.52 ± 1.50 | 3.85 ± 0.16 | 1.64 ± 0.26 | 0.89 ± 0.12 |
| Tumor | 4.74 ± 0.77 | 4.51 ± 0.15 | 3.59 ± 0.53 | 1.87 ± 0.773 |
| Tumor-to-blood | 3.05 ± 1.65 | 9.68 ± 1.834 | 23.93 ± 2.52 | 34.03 ± 18.36 |
| Tumor-to-liver | 0.66 ± 0.22 | 1.18 ± 0.08 | 2.21 ± 0.25 | 2.11 ± 0.82 |
| Tumor-to-kidney | 0.03 ± 0.00 | 0.03 ± 0.00 | 0.04 ± 0.00 | 0.05 ± 0.02 |

FIBRONECTIN-BINDING PEPTIDES FOR USE IN TUMOR OR FIBROSIS DIAGNOSIS AND THERAPY

RELATED APPLICATIONS

This application is a National Stage of PCT/EP2017/064543, filed 14 Jun. 2017, titled FIBRONECTIN-BINDING PEPTIDES FOR USE IN TUMOR OR FIBROSIS DIAGNOSIS AND THERAPY, published as International Patent Application Publication No. WO 2017/216223, which claims the benefit and priority to European Application No. 16174824.9, filed on 16 Jun. 2016, both of which are incorporated herein by reference in their entirety for all purposes.

INCORPORATE BY REFERENCE

In compliance with 37 C.F.R. § 1.52(e)(5), the sequence information contained in electronic file name: 50519PCT_ST25_for_filing_v_14_06_2017.txt; size 60.2 KB; created on: 14 Jun. 2017 using Patent-In 3.5, and Checker 4.4.0 is hereby incorporated herein by reference in its entirety.

FIELD OF THE INVENTION

The present invention is directed to a composition comprising at least one fibronectin binding polypeptide (FnBP) linked to at least one diagnostic or therapeutic agent, a nucleic acid encoding a fusion polypeptide comprising at least one fibronectin binding polypeptide (FnBP) linked to at least one diagnostic or therapeutic polypeptide agent as well as a corresponding recombinant vector and host cell comprising such a nucleic acid and preferably expressing said fusion polypeptide. The invention also relates to a kit of parts comprising at least one fibronectin binding polypeptide (FnBP), at least one diagnostic or therapeutic agent, and optionally one or more chemical agents for linking the fibronectin binding polypeptide (FnBP) to the diagnostic or therapeutic agent. In addition, the present invention intends said composition, nucleic acid, vector, host cell and kit for use in the therapeutic or prophylactic treatment of a disease, preferably a disease associated with abnormal fibronectin accumulation such as cancer, fibrosis or immune diseases.

BACKGROUND

Fibronectin is a high-molecular weight (~440 kDa) glycoprotein of the extracellular matrix (ECM) that binds to membrane-spanning receptor proteins called integrins (Hynes, R. O. (2009), Science 326(5957): 1216-1219). Similar to integrins, fibronectin binds among other residues extracellular matrix components such as collagen, fibrin, and heparan sulfate proteoglycans. Fibronectin exists as a protein dimer, consisting of two nearly identical monomers linked by a pair of disulfide bonds. The fibronectin protein is produced from a single gene, but alternative splicing of its pre-mRNA leads to the creation of several isoforms. Soluble plasma fibronectin is a major protein component of blood plasma that is produced by hepatocytes and circulates in body fluids at high concentrations of about 300 μg/mL. Insoluble cellular fibronectin is a major component of the ECM. It is secreted by various cells, primarily fibroblasts, as a soluble protein dimer and is then assembled into an insoluble matrix in a complex cell-mediated process.

Fibronectin plays a major role in cell adhesion, growth, migration and differentiation, and it is important for processes such as wound healing and embryonic development. Altered fibronectin expression, degradation and organization has been associated with a number of pathologies, including cancer and fibrosis. Several of the morphological changes observed in tumors and tumor-derived cell lines have been attributed to altered fibronectin expression, increased fibronectin degradation and/or altered expression of fibronectin-binding receptors, such as different integrin types ($\alpha 5\beta 1$, $\alpha v\beta 1$, $\alpha v\beta 3$, $\alpha v\beta 5$, $\alpha v\beta 6$ or $\alpha v\beta 8$ integrins).

In lung carcinoma fibronectin expression is increased, especially in non-small cell lung carcinoma. The adhesion of lung carcinoma cells to fibronectin enhances tumorigenicity and confers resistance to apoptosis-inducing chemotherapeutic agents. Fibronectin has been shown to stimulate the gonadal steroids that interact with vertebrate androgen receptors, which are capable of controlling the expression of cyclin D and related genes involved in cell cycle control. These observations suggest that fibronectin may promote lung tumor growth/survival and resistance to therapy, and it could represent a novel target for the development of new anticancer drugs. Fibronectin acts as a potential biomarker for radioresistance. FN-FGFR1 fusion is frequent in phosphaturic mesenchymal tumors.

WO2007/128563A1 teaches fusion proteins comprising an antibody or functional fragment thereof specifically binding the extracellular domain of oncofetal fibronectin (ED-B) and a specific effector selected from the cytokines IL-10, IL-15, IL-24 and GM-CSF (Granulocyte-macrophage colony-stimulating factor) for the manufacture of a medicament for treating tumors or chronic inflammatory diseases, in particular atherosclerosis, arthritis and psoriasis. ED-B is a 91-amino-acid type III homology domain that is inserted into the fibronectin molecule by a mechanism of alternative splicing at the level of the primary transcript whenever tissue remodeling takes place [Zardi et al., Embo J. 6(8): 2337-42 (1987)]. ED-B is essentially undetectable in healthy adult tissues. Its expression is strongly associated with the remodeling of the ECM and angiogenesis. The domain is abundant in many aggressive tumors and, depending on the tumor type, displays either predominantly vascular or diffuse stromal patterns of expression [Carnemolla et al., J. Cell Biol. 108(3): 1139-48 (1989)].

Compared to peptides, nanoparticles and antibodies for targeting live biological targets have a major setback when it comes to their permeability and retention at the target tissue (see Wilhelm et al, Analysis of nanoparticle delivery to tumours, Nature Reviews Materials 1, (2016) 1-12). Antibodies are large proteins with a molecular weight of 150 kDa and a hydrodynamic radius of 15 to 20 nm. Moreover, antibodies and fragments thereof are relatively sensitive to environmental and metabolic challenges. Smaller fragments of antibodies such as monomers and the dimers of the Fab recognition patterns still represent bulky molecules with sizes of around 50 to 100 kDa, respectively. Smaller targeting compounds include proteins, peptides, nucleic acid-based ligands, e.g. aptamers, and small molecules [Bertrand et al., Advanced Drug Delivery Reviews 66, (2014): 2-25]. These smaller molecules have the advantage of a faster diffusion and faster targeting of the target tissue resulting in more homologous distribution within a pathological tissue like cancer or fibrosis.

However, one major and generally accepted drawback of therapeutic peptides is their poor stability in blood plasma leading to a short half-life time and, consequently, reduced therapeutic or diagnostic efficacy. Rapid degradation of peptides in blood serum is often observed to result in a loss of affinity to the target protein. Therefore, strategies for stabilization have to be introduced. There are natural peptides mainly originating from amphibians and reptiles, which show a higher metabolic stability in human blood than the related human analogues due to evolutionary engineering. Another possibility to increase stability is chemically by changing the metabolic cutting sites within a peptide. This includes the replacement of natural amino acids by unnatural amino acids or a chemical modification of the amide bonds.

In the context of bacterial wound infection, Chabria et al. (Nature Communications, 1:135, 2010, 1-9) report that specific binding of bacterial FnBR via backbone hydrogen bonds can be mechanically regulated by "stretching" Fn-fibers in vitro and suggest that cell-generated forces are sufficiently high to deactivate specific binding of bacterial adhesins to Fn-fibers. The authors thus speculate that the mechanobiology of the Fn-comprising ECM might regulate bacterial and cell-binding events, virulence and the course of infection.

Cao et al. [PNAS, vol. 109, 19:7251-7256, May 8, 2015] report phage display-based molecular probes LNLPHG and RFSAFY that discriminate force-induced structural states of fibrillar fibronectin in vivo, a so-called "relaxed" (preferentially bound by LNLPHG) and a "strained" (preferentially bound by RFSAFY) state of Fn fibers. Phages displaying SRWYRI, ARERFY and GSNSKY preferentially also bound the relaxed state with lower but significant binding affinity. Random phage displayed-peptide probes exhibited strain-selective binding to manually extruded fibronectin (Fn) fibers, cell-derived Fn ECM and ex vivo living lung slices. The authors speculate on the possible future use of these peptide probes for mapping molecular strain events in unmodified native ECM microenvironments as well as for targeting Fn (ECM) in altered structural states associated with disease. On the other hand, the authors admit that there still is no direct evidence that extensibility of Fn within fibers and Fn type III domain unfolding events observed under artificial strain conditions actually occur in vivo. Hence, it is highly speculative whether or not peptides identifying either the "relaxed" or "strained" Fn could function as tumor markers, in particular, because only the phages displaying those peptides were tested, but not the peptides alone.

Hertig et al. (Nano Lett., 12, 5132-5168, 2012) disclose the isolation and further engineering of bacterially derived Fn-binding proteins (FnBPs). The natural FnBPs are covalently linked to the bacterial cell membrane and can contain several intrinsically disordered Fn-binding repeats (FnBRs). Interestingly, the FnBRs expressed by several gram-positive bacteria and a spirochete show little homology, though they all recognize and bind the same domains of Fn. Conserved residues are mostly found in the FnI-binding motifs, with the E-D/E-T/S motif being highly conserved and found in almost every FnBR. Fn features five FnI modules, which are spaced apart by peptide linkers and all of which can serve as FnBP binding partners.

In summary, fibronectin is a prevalent protein in the plasma and ECM of tissues, which can be upregulated in fibrosis and cancer tissues. Splice variants of fibronectin have utility for targeting splice variant-specific cancer types. The binding of naturally occurring and phage-display-based FnBPs can vary with the natural relaxed and the artificially strained state of Fn. However, the exact role of relaxed versus strained Fn fibers in mammals remains unknown.

It is the objective of the present invention to provide novel and improved means for targeting diagnostic and/or therapeutic means to tissues associated with increased Fn content, preferably fibrotic and cancer tissues with increased Fn content, or to organs that accumulate injected peptides.

SUMMARY

In a first aspect, the above objective is solved by a composition comprising:

(i) at least one fibronectin binding peptide (FnBP) linked to (ii) at least one diagnostic or therapeutic agent.

It was surprisingly found that the above composition selectively targets Fn fibers in vitro and also Fn-rich tumor or fibrosis tissue when injected in vivo. Furthermore, the composition displays high plasma stability and the clearance of the composition from Fn-rich tissue such as tumor or fibrosis tissue was significantly slower compared to other organs. A further hallmark of the above composition is the effective tissue penetration and long retention time in Fn-specific target tissue (see Examples 5 and 6).

Without wishing to be bound by theory it is noted that the surprising blood stability of the rather short FnBPs could result from protective binding to soluble plasma Fn, the reversible binding of which, however, does not compromise FnBP accumulation at tumor- and fibrosis-associated target tissues (see FIG. 2A). It also seems possible that Fn infiltrates fibrosis and tumor tissue to further improve accumulation of the composition of the invention.

The term "fibronectin binding peptide (FnBP)", as used herein, preferably encompasses FN-binding oligo- and polypeptides that consist of 6 to 100 amino acids but also encompasses polypeptides that feature more than 100 amino acids. The term excludes antibodies and Fn-binding antibody fragments such as Fabs. The polypeptides for practicing the present invention preferably consist of 6 to 60, 6 to 50, 20 to 60, or 30 to 50, more preferably 30 to 45, most preferably about 40 amino acids. In a preferred embodiment, the FnBPs for use in the instant invention bind to soluble plasma Fn and also to insoluble, fibrillar ECM Fn made from either plasma or cellular Fn, or from both. Most preferably, the FnBPs for use in the instant invention bind to at least soluble plasma Fn. It is also preferred that the FnBPs do not specifically and exclusively bind to portions (extra domains) of rare splice variants of FN that are not or only to a small proportion present in common soluble plasma FN and insoluble fibrillar ECM Fn, in particular splice variants containing the extra domains A (EDA) and/or the extra domain B (EDB). The FnBPs for use in the present invention can bind to any site of common soluble and insoluble Fn protein, however, it is preferred that they bind to the N-terminal region of Fn. Furthermore, it is preferred that the FnBPs for use in the present invention bind to stretched as well as to unstreched Fn depending on their specific design.

The Fn-binding properties of the FnBPs for use in the instant invention can be easily assayed and confirmed by binding assays known in the art, e.g. in Chabria et al. (Nature Communications, 1:135, 2010, 1-9). For example, suitable assay conditions are presented in the Examples 2, 3 and 5 below. FnBPs for use in the present invention preferably have a specific binding affinity for soluble plasma and/or insoluble ECM Fn of 100 μM to 5 μM preferably 1 nM to 1 μM, more preferably 1 nM to 100 nM.

The expression "diagnostic agent", as used herein, is not restricted and includes any compound which can be detected and preferably quantified in and/or outside an organism, preferably a mammal, more preferably a human, or parts thereof, such as for example cells, organs and/or fluids, such as for example the serum, through suitable chemical and/or physical measurement methods. A diagnostic agent according to the present invention can also include multiple components which require further components to be detected that are not part of the diagnostic agent per se, e.g. a radioactive or positron-emitting element that is complexed by a chelating agent.

Herein, the expression "therapeutic agent" means any compound which brings about a pharmacological effect either by itself or after its metabolic conversion (pre-drug) in the organism in question, and thus also includes the metabolic derivatives from these conversions.

According to the present invention, there is no specific restriction as to how the FnBP and the diagnostic or therapeutic agent are linked to each other, as long as the FnBP and the agent are linked in a manner that is sufficiently stable under physiological conditions, preferably in blood plasma, to physically and/or chemically connect/allocate/bind the components together until they reach the target site and unfold their effect(s) and as long as the diagnostic or therapeutic agent is still effective for its purpose. The FnBP and the agent may be linked to each other covalently or noncovalently, e.g. by hydrophobic interaction, van der Waals forces, electrostatic attraction, etc. or via one or more spacers or at least one, preferably cleavable, linker. The expression "cleavable linker" means any linker which can be cleaved physically or chemically. Examples for physical cleavage are cleavage by light, radioactive emission or heat, while examples for chemical cleavage include cleavage by redox-reactions, hydrolysis, pH-dependent cleavage or cleavage by enzymes.

This invention even includes applications in which the diagnostic or the therapeutic agents are bound to the Fn binding moiety in vivo after separate concomitant or sequential administration of both components of the composition of the present invention. This may be an approach, which is known as pre-targeting.

One such linking and pre-targeting technology which can be used for linking at least one FnBP to the therapeutic or diagnostic agent may be based on single strand complementary nucleic acid hybridization, where the FnBP comprises a single strand nucleic acid sequence that hybridizes to a complementary single strand nucleic acid sequence that comprises the diagnostic or therapeutic agent. For example, an FnBP linked to a single strand nucleic acid can be administered to a subject in need of therapy or diagnosis at a first time point for binding and imaging or treating Fn-accumulated target areas, and a therapeutic or diagnostic agent with the complementary nucleic acid sequence can be administered at a second time point so that the therapeutic or diagnostic agent accumulates at the pre-targeted Fn site of interest and exerts the desired action on said target. This concept has the advantage that the biodistribution of the targeting hybrid FnBP is controlled separately from the biodistribution of the diagnostic or therapeutic agent. The affinity of the later administered effector molecule (diagnostic or therapeutic agent) to the first target molecule can be easily adapted via the design of the oligonucleotide length, each added nucleotide contributing to the affinity and stability of the hybridization. Of course, the effector can also be administered first and the targeting FnBP hybrid secondly. For further information on this technology, which includes the PAINT technology reference is made to Jungmann et al. (2014), Nat Methods 11(3): 313-318; Raab et al. (2014), Chemphyschem 15(12): 2431-2435; and Johnson-Buck et al. (2013), Nano Letters, 13(2), 728-733. Other pretargeting approaches include the biotin/avidin system, the in vivo click method or any other pretargeting methods, reference is made to Zeglis et al. (2015), Molecular Pharmaceutics, 12(10): 3575-3587.

The diagnostic or therapeutic agent for use in the inventive composition can be selected broadly from those commonly known in the field of diagnosis and medical treatment, preferably it is selected from the group consisting of a radionuclide, cytostatic or cytotoxic agent, thermo-inducing agents, a cytokine, an immunosuppressant, an antirheumatic, an antiphlogistic, an antibiotic, an analgesic, a virostatic, and an antimycotic agent, a transcription factor inhibitor, a cell cycle modulator, an MDR modulator, a proteasome or protease inhibitor, an apoptosis modulator, an enzyme inhibitor, an angiogenesis inhibitor, a hormone or hormone derivative, a radioactive substance, a positron-emitting substance, a light emitting substance, and a light absorbing substance.

In a preferred embodiment, the composition of the present invention is a composition, wherein the at least one fibronectin binding polypeptide (FnBP) is a polypeptide selected from the group consisting of:
(a) polypeptides comprising an amino acid sequence selected from the group consisting of SEQ ID NOs: 1 to 147, preferably SEQ ID NOs: 117-147, more preferably SEQ ID NOs: 141, 143 and 145;
(b) polypeptides comprising an amino acid sequence having an amino acid sequence identity of at least 70 or 80%, preferably at least 90 or 95% with an amino acid sequence selected from the group consisting of SEQ ID NOs: 1 to 147, preferably SEQ ID NOs: 117-147, more preferably SEQ ID NOs: 141, 143 and 145;
(c) polypeptides comprising an amino acid sequence encoded by a nucleic acid having a nucleic acid sequence selected from the group consisting of SEQ ID NOs: 148 to 294, preferably SEQ ID NOs: 264-294, more preferably SEQ ID NOs: 288, 290 and 292;
(d) polypeptides comprising an amino acid sequence encoded by a nucleic acid having at least 80%, preferably at least 90 or 95% nucleic acid sequence identity with a nucleic acid sequence selected from the group consisting of SEQ ID NOs: SEQ ID NOs: 148 to 294, preferably SEQ ID NOs: 264-294, more preferably SEQ ID NOs: 288, 290 and 292; and
(e) functional fragments and/or functional derivatives of any of (a), (b), (c) and (d).

In a preferred embodiment, the composition of the present invention is a composition, wherein the at least one fibronectin binding polypeptide (FnBP) is a polypeptide comprising the CD-loop of IL-7, or having an amino acid sequence identity of at least 70 or 80%, preferably at least 90 or 95% to the CD-loop of IL-7, or functional fragments and/or functional derivatives of the CD-loop of IL-7.

The identity of related amino acid molecules can be determined with the assistance of known methods. In general, special computer programs are employed that use algorithms adapted to accommodate the specific needs of this task. Preferred methods for determining identity begin with the generation of the largest degree of identity among the sequences to be compared. Preferred computer programs for determining the identity among two amino acid sequences comprise, but are not limited to, TBLASTN, BLASTP, BLASTX, TBLASTX (Altschul et al., (1990) J. Mol. Biol., 215, 403-410), ClustalW (Larkin M A et al., Bioinformatics, 23, 2947-2948, 2007) or PHYRE2 (Kelley L A et al., (2015) Nature Protocols 10, 845-858). The BLAST programs can be obtained from the National Center for Biotechnology Information (NCBI) and from other sources (BLAST handbook, Altschul et al., NCB NLM NIH Bethesda, Md. 20894). The ClustalW program can be obtained from clustal.org and the PHYRE2 program.

The term "functional derivative" of a polypeptide for use in the present invention is meant to include any polypeptide or fragment thereof that has been chemically or genetically modified in its amino acid sequence, e.g. by addition, substitution and/or deletion of amino acid residue(s) and/or has been chemically modified in at least one of its atoms and/or functional chemical groups, e.g. by additions, deletions, rearrangement, oxidation, reduction, etc. as long as the derivative still has at least some Fn binding activity to a measurable extent, e.g. of at least about 1 to 10% Fn binding activity of the original unmodified polypeptide for use in the invention, e.g. SEQ ID NOs: 117-147. Functional derivatives of a polypeptide for use in the present invention include non-natural polypeptides and glycosylated, phosphorylated, PEGylated, etc. derivatives.

In this context a "functional fragment" for use in the invention is one that forms part of a polypeptide or derivative for use in the invention and still has at least some Fn binding activity to a measurable extent, e.g. of at least about 1 to 10% Fn binding activity of the original unmodified polypeptide for use in the invention, e.g. SEQ ID NOs: 117 to 147.

Preferably, a functional fragment or functional derivative for use in the composition of the present invention has a binding affinity to soluble and insoluble fibrillary ECM of at least 5 μM, preferably at least 500 nM, most preferably 50 nM.

In a further preferred embodiment, the polypeptide for use in the composition of the present composition binds specifically to at least one of fibronectin subunits $FnI_{1-6}$, $FnII_{1-2}$, $FnI_{7-9}$ or $FnIII_{7-15}$, preferably subunits $FnI_{1-5}$, $FnII_{1-2}$, $FnIII_{7-11}$, more preferably subunit $FnI_{2-5}$.

In another preferred embodiment, the polypeptide for use in the composition of the present invention binds specifically to at least one of fibronectin subunit of its collagen binding site $FnI_6$-$FnII_{1-2}$-$FnI_{7-9}$, preferably subunits $FnII_{1-2}$-$FnI_{7-9}$, more preferably subunit $FnI_{7-9}$.

In another preferred embodiment, the polypeptide for use in the composition of the present invention binds specifically to at least one of fibronectin type Ill subunits, preferably subunits $FnII_{7-15}$ more preferably subunit $FnII_{7-11}$ It is noted that the composition of the present invention may consist of at least one fibronectin binding polypeptide (FnBP) linked to at least one diagnostic or therapeutic agent and as such may comprise one compound only.

The diagnostic agent for use in the inventive composition is preferably selected from the group consisting of radionuclides, MRI active compounds, ultrasound contrast agents, fluorophores, markers for PET and SPECT, preferably $^{18}$F, $^{44}$Sc, $^{64}$Cu, $^{67/68}$Ga, $^{99m}$Tc, $^{111}$In, fluorophores in the far red/near-IR spectral region, Gd-based and Fe particle based MRI contrast agents, more preferably SPECT markers $^{99m}$Tc, $^{111}$In and PET markers $^{44}$Sc and $^{64}$Cu.

For diagnostic purposes, the diagnostic agent for use in the composition of the present invention is preferably suitable for easy identification and quantification, for example, in computed tomography (CT), single photon emission computed tomography (SPECT/CT), magnetic resonance imaging (MRI), positron emission tomography (PET), ultrasound imaging or via in vivo optical detection of fluorophores in the far red/near IR spectral range. The diagnostic agent is preferably radiolabeled by a radionuclide. The radionuclide for use in the composition of the present invention can be selected from the group consisting of $^{123}$I, $^{131}$I, $^{111}$In, $^{99m}$Tc, $^{201}$Tl, $^{67}$Ga, $^{155}$Tb or any other radioisotope emitting a suitable γ-ray. Also, the radionuclide can preferably be a positron emitting atom, preferably selected from the group consisting of an $^{11}$C—, $^{13}$N—, $^{15}$O—, $^{18}$F—, $^{62}$Cu, $^{64}$Cu—, $^{68}$Ga—, $^{76}$Br—, $^{82}$Rb—, $^{124}$I, $^{44}$Sc, $^{43}$Sc, $^{89}$Sr or any other radioisotope emitting a $\beta^+$ which is suitable for PET. Preferably, the radionuclide can be bound covalently to FnBP or via a chelator or any other chemical binding to FnBP. The chelator is preferably selected from the group consisting of DPTA (diethylene triaminepentaacetic acid), DOTA (1,4,7,10-tetraazacyclododecane-1,4,7,10-tetraacetic acid), and NOTA (1,4,7-triazonane-1,4,7-triacetic acid) or derivatives thereof or any chelating agents which can be used to attach a radiometal to the peptide.

In a further preferred embodiment, the therapeutic agent of the present composition is selected from the group consisting of cytostatic agents, cytotoxic agents, cytokines, transcription factor inhibitors, proteasome and protease inhibitors, apoptosis modulators, cell cycle modulators, angiogenesis inhibitors, hormones or hormone derivatives, photodynamic therapy molecules, nanoand microparticles (for thermoablation therapy and as transport vehicle), agents that interfere and alter cell contractility, radionuclides, miR-NAs, siRNAs and immunomodulatory antigen molecules.

Preferred radionuclides are those emitting β ($^{62}$Cu, $^{64}$Cu—, $^{68}$Ga—, $^{76}$Br—, $^{82}$Rb—, $^{124}$I, $^{44}$SC, $^{43}$Sc, $^{89}$Sr or any other $\beta^+$ emitting isotope), $\beta^-$ (e.g. $^{90}$Y, $^{177}$Lu, $^{161}$Tb, $^{64}$Cu, $^{67}$Cu, $^{47}$Sc or any other $\beta^-$ emitting isotope), α ($^{225}$Ac, $^{213}$Bi, $^{211}$At, $^{223/225}$Ra or any other α emitting isotope), or Auger electron emitter ($^{161}$Tb, $^{169}$Er, $^{99m}$Tc, $^{111}$In or any other Auger electron emitting isotope), or any combination of therapeutic applicable radio-emissions.

The therapeutic radioisotope can preferably be bound covalently to the FnBP or via any chelator. As a chelator, derivatives of DTPA, DFO, DOTA, NOTA, cryptate or any other chelating system can be used. The radisotope can be chelated as central atom with a metallic character as well it can be served as ligand.

Especially suitable cytostatic agents for use in the present invention are the N-nitrosoureas such as nimustine, the anthracyclines doxorubicin, daunorubicin, 30 epirubicin, idarubicin, mitoxantrone and ametantrone, and any derivatives thereof such as 2-pyrollinoanthracyclines, morpholinoanthracyclines, diacetatoxyalkylanthracyclines; the alkylating agents chlorambucil, bendamustine, melphalan, and oxazaphosphorines, and any derivatives thereof; the antimetabolites, for example purine antagonists or pyrimidin antagonists, such as 5-fluorouracil, 2'-deoxy-5-fluorouridine, cytarabine, cladribine, fludarabine, pentostatine, gemcitabine and thioguanine, and any derivatives thereof; folic acid antagonists such as methotrexate, raltitrexed, pemetrexed and plevitrexed, the taxanes paclitaxel and 5 docetaxel, and any derivatives thereof; the camptothecins topotecan, irinotecan, 9-aminocamptothecin and camptothecin, and any derivatives thereof; the Vinca alkaloids vinblastine, vincristine, vindesine and vinorelbine, and any derivatives thereof; calicheamicins and any derivatives thereof; maytansinoids and any derivatives thereof; auristatins and any derivatives thereof; epothilones and any derivatives thereof; bleomycin, dactinomycin, plicamycin, mitomycin C and cis-configured platinum(II) complexes.

Most preferred cytostatic agents are Doxorubicin, Paclitaxel, Chlorambucil, Topotecan and Vincristine. Most preferred cytokines are Interleukin-2, Interleukin-7, Interferon-γ and tumor necrosis factors. Most preferred growth factor and cytokine inhibitors include VEGF, FGF, EGF, PGF and TGF inhibitors. Most preferred transcription factor inhibitors are Curcumin, Ribavirin and Genistein. Most preferred apoptosis modulators are Imatinib, Erlotinib and Bryostatin. Most preferred cell cycle modulators are Flavopiridol and Roscovitine. Most preferred angiogenesis inhibitors are Endostatin, Celexocib, ADH-1 (exherin) and Sunitinib. Most preferred hormone and hormone derivatives are Flutamide, Fosfestrol, Tamoxifen and Relaxin. Most preferred radionuclides are $^{64}$Cu, $^{90}$Y, $^{111}$In, $^{131}$I, $^{161}$Tb, $^{169}$Er, $^{177}$Lu. The most preferred therapeutic agents for use in the composition of the present invention are Paclitaxel, Chlorambucil, Endostatin, Sunitinib, Interluekin-7 and $^{90}$Y.

Especially suitable cytokines for use according to the present invention are, for example, interleukin 2, interleukin 7, interferon a-2a, interferon a-2b, interferon-1a, interferon-1b, interferon y-1b, tumor necrosis factor, and any derivatives thereof.

Especially preferred transcription factor inhibitors for use according to the present invention are, for example compounds that inhibit activation of NF-KB such as curcumin (diferuloylmethane) epigallocatechin-3-gallate (EGCG; green tea polyphenols), phenanthrolines, pyrrolinedithiocarbamate (PDTC), quercetin, tepoxaline (5-(4-chlorophenyl)-N-hydroxy-(4-methoxyphenyl)-N-methyl-1 H-pyrazole-3-propan-amide), PMC (2,2,5,7,8-pentamethyl-6-hydroxychromane), benzyisocyanate, resveratol, genistein, lupeol, lycopene, panepoxydone, epoxyquinomicin C, dehydroxymethylepoxyquinomicin (DHMEQ), cycloepoxydon, gliotoxin, as well as 1-KB-alpha phosphorylation and/or degradation inhibitors such as PS-1,145, BAY-11-7082 (E3 [(4-methylphenyl)-sulfonyl]-2-propenenitri le), BAY-11-7085 (E3[(4-t-butylphenyl)-sulfonyl]-2-propenenitrile), cycloepoxydon; 1-hydroxy-2-hydroxy-methyl-3-pent-1-enylbenzene, sanguinarine (pseudochelerythrine, 13-methyl-[1,3]-benzodioxolo-[5,6-c]-1,3-dioxolo-4,5 phenanthridinium), sulfasalazine, capsaicin (8-methyl-N-vanillyl-6-nonenamide), emodin (3-methyl-1,6,8-trihydroxyanthraquinone), erbstatin (tyrosine kinase inhibitor), estrogen (E2), gliotoxin, genistein, resiniferatoxin, and miscellaneous inhibitors of NF-KB such as beta-amyloid protein, glucocorticoids (dexamethasone, prednisone, methylprednisolone), leptomycin B (LMB), 0,0'-bismyristoyl thiamine disulfide (BMT), ADP ribosylation inhibitors, e.g., bi-, tri, or tetracyclic lactames, 1,8-naphtalimide derivatives, phenanthridin-6-ones, 3,4-dihydro-5-methyl-isoquinolin-1 (2H)-one, benzoxazole-4-carboxamide, 1,6-naphthyridine-5 (6H)-ones, quinazolin[3,4-d]pyrimidin-4(3H)-ones, 1,5-dihydroxyisoquinoline, 2-methyl-quinazolin-4[3H]-ones, 1,11b-dihydro-[2H]benzopyrano [4,3,2-de]isoquinolin-3-one, atrial natriuretic peptide (ANP), atrovastatin (HMG-CoA reductase inhibitor), calcitriol (1a,25-dihydroxyvitamine D3), E3330 (quinone derivative), herbimycin A, hypericin, hydroquinone (HQ), KT-90 (morphine synthetic derivatives), mevinolin, 5'-methylthioadenosine (MTA), pentoxifylline (1-(5'-oxohexyl) 3,7-dimethylxanthine, PTX), phenyl-N-tert-butylnitrone (PBN), pituitary adenylate cyclase-activating polypeptide (PACAP), quinadril (ACE inhibitor), ribavirin, secretory leukocyte protease inhibitor (SLPI), serotonin derivative (N-(p-coumaroyl) serotonin, silymarin, vasoactive intestinal peptide (VIP), D609 (phosphatidylcholine-phospholipase C inhibitor), R031-8220 (PKG inhibitor), SB203580 (p38 MAPK inhibitor), triptolide (PG490, extract of Chinese herb), LY294,002, mesalamine, wortmannin (fungal metabolite), or CHS 828 (N-(6-(p-chlorophenoxy)-hexyl)-N'-cyano-N,-4-pyridylguanidine), sesquiterpene lactones such as parthenoilde, helenalin, miller-9E-enolid and budlein A.

Especially preferred proteasome and protease inhibitors for use according to the present invention are, for example, peptide aldehydes: ALLnL (N-acetyl-leucinyl-leucynil-norleucynal, MG101), LLM (N-acetyl-leucinyl-leucynil-methional), Z-LLnV (carbobenzoxyl-leucinyl-leucyni l-norvalinal, MG115), Z-LLL (carbobenzoxyl-leucinyl-leucynil-leucynal, MG132), boronic acid derivatives, e.g. PS-273, PS-293, PS-296, PS-303, PS-305, PS-313, PS-321, PS-325, PS-334, PS-341, PS364, PS-352, PS-383, lactacystine, beta-lactone, boronic acid peptide, ubiquitin ligase inhibitors deoxyspergualin, APNE (N-acetyl-DL-phenylalanine-beta-naphthylester), BTEE (N-benzoyl L-tyrosineethylester), DCIC (3,4-dichloroisocoumarin), DFP (diisopropyl-uorophosphate), TPCK (N-alpha-tosylL-phenylalanine chloromethyl ketone), TLCK (N-alpha-tosyl-L-lysine chloromethyl ketone).

Especially preferred apoptosis modulators for use according to the present invention are, for example, farnesyl transferase inhibitors, e.g. R115777, SCH66336, BMS214662, Imatinib, 17-AAG, EGFR inhibitors, e.g. ZD1839, ZD647, BIBW 2992, or erlotinib, MEK inhibitors, e.g. PD 032590, RAF inhibitors e.g. BAY43-9006, PKG inhibitors, e.g. UCN-01, PKC-412, Bryostatin, ISIS-3521, LY333531, safingol, CGP-41251 (midostaurin), HDAC inhibitors, e.g., suberoyl-3-aminopyridineamide hydroxamic acid, lonidamine, apoptin, survivin, rapamycin, CCI-779, RADO01 (everolimus), PXD101, tyrosine kinase inhibitors, e.g. Iressa, OSI-774, STI-571, inhibitors of enzymes in the mitogen-activated protein kinase pathway e.g., PD-098059, U-0126.

Especially preferred cell cycle modulators for use according to the present invention are, for example, flavopiridol, bryostain-1, roscovitine, BMS-387032, perifosine, or lovastatin.

Especially preferred angiogenesis inhibitors for use according to the present invention are, for example thalidomide, endostatin, celecoxib, ABT-510, combrestatin A4, dalteparin, dimethylxanthenone acetic acid, lenalidomide, LY317615 (enzastaurin), PPI-2458, ADH-1 (exherin), AG-013736, AMG-706, AZD2171, Bay 43-9006 (sorafenib), BMS-582664, CHIR-265, GW786034 (pazopanib), PI-88, PTK787/ZK 222584 (vatalanib), RADO01 (everolimus), SU11248 (sunitinib), suramin, XL184, ZD6474, ATN-161, or EMO 121974 (cilenigtide), and saposin-A derived peptides inducing thrombospondin-1 (preferably featuring Seq. ID Nos. 4 (DWLPK) and 5 (DWLP) of US Patent 2015/0320825 A1). Especially preferred hormones or hormone derivatives for use according to the present invention are, for example, aminogluthemid, buserilin, cyproteronacetate, droloxifen, ethinylestradiol, flutamid, formesta, fosfestrol, gestonoroncaproate, goserilin, leuprolein, lynestrenol, medrogeston, medroxyprogesteronacetate, megestrolactetate, octreotid, relaxin, tamoxifen, toremifin, triptorelin, anastrazole, exemestane, or letrozole.

Especially preferred agents that interfere with cell contractility are for example inhibitors of transforming growth factor-3, such as 3-(6-Methyl-2-pyridinyl)-N-phenyl-4-(4-quinolinyl)-1H-pyrazole-1-carbothioamide, 4-[4-(2,3-Dihydro-1,4-benzodioxin-6-yl)-5-(2-pyridinyl)-1H-imidazol-2-yl]benzamide, 4-[4-[3-(2-Pyridinyl)-1H-pyrazol-4-yl]-2-pyridinyl]-N-(tetrahydro-2H-pyran-4-yl)-benzamide, 4-[3-(2-Pyridinyl)-1H-pyrazol-4-yl]-quinoline, 4-[2-Fluoro-5-[3-(6-methyl-2-pyridinyl)-1H-pyrazol-4-yl]phenyl]-1H-pyrazole-1-ethanol, 2-(3-(6-Methylpyridine-2-yl)-1H-pyrazol-4-yl)-1,5-naphthyridine, 4-[4-(1,3-benzodioxol-5- yl)-5-(2-pyridinyl)-1H-imidazol-2-yl]benzamide, 2-[4-(1,3-Benzodioxol-5-yl)-2-(1,1-dimethylethyl)-1H-imidazol-5-yl]-6-methyl-pyridine, 6-[2-(1,1-Dimethylethyl)-5-(6-methyl-2-pyridinyl)-1H-imidazol-4-yl]quinoxaline or 2-(5-Chloro-2-fluorophenyl)-4-[(4-pyridyl)amino]pteridine. Also inhibitors for tissue transglutaminase, such as 2-[(3,4-Dihydro-4-oxo-3,5-diphenylthieno[2,3-d]pyrimidin-2-yl)thio] acetic acid hydrazide. Also, inhibitors for tumor necrosis factor α signaling, such as pentoxifylline or other xanthine derivatives, as well as bupropion.

An especially preferred radionuclide for use in the present invention can be $^{177}$Lu or $^{131}$I Alternatively, the radionuclide can be selected from the group consisting of $^{90}$Y and $^{111}$In. The radionuclide can be bound to the FnBP or to a linker on the FnBP by a chelator. The chelator can be selected from the group consisting of cyclic DPTA (diethylene triaminepentaacetic acid) anhydride, ethylenediaminetetraacetic acid (EDTA), DOTA (1,4,7,10-tetraazacyclododecane-1,4,7,10-tetraacetic acid), and NOTA (1,4,7-triazonane-1,4,7-triacetic acid) or derivatives thereof or any chelating agent which can be used to attach a radiometal to the peptide.

Further especially preferred therapeutic agents are miRNAs and siRNAs, for example, those that are specific for CD40, CD80 and CD86, and also any agents that target clustered regularly interspaced short palindromic repeat (CRISPR) components for gene-editing purposes, or antigens that modulate the immune system, for example, insulin-associated antigens, P31, whole gliadin, whole peanut extract, myelin oligodendrocyte glycoprotein (preferably amino acids 35-55), proteolipid protein 1 (preferably amino acids 139-151 and 178-191), Factor V (preferably amino acids 75-89, 1723-1737 and 2191-2210).

Also, therapeutic agents for tolerance induction are preferred, which exploit toleragenic immune modifying components (see Getts, D. R., et al., Trends in Immunology, 2015, 36(7), 419-427). The induction of tolerance using, e.g. TIMPs requires that the antigen-loaded particles must be delivered intravenously MARCO, for example, is shown to be involved in particle uptake and tolerance induction. MARCO is expressed on circulating inflammatory monocytes as well as marginal zone macrophages. In the context of activated autoreactive T cells, the upregulation of negative costimulatory molecules on APCs, including PDL-1 and CTLA-4, promote autoreactive T cell anergy and apoptosis.

Preferred embodiments for practicing the present invention are directed to a composition, wherein the therapeutic agent is an antifibrotic agent, preferably selected from the group consisting of
  (a) integrin inhibitors, preferably those integrin inhibitors disclosed in WO 2015/048819 A1, more preferably the αvβ1 integrin inhibitor shown in FIG. 1 and other integrin blocking compounds as listed in table 1 of WO 2015/048819 A1;
  (b) bone morphogenic protein 7 (BMP-7) (see for example Zhong et al., Int. J. of Medical Sciences 2013, 10, 441-450; Zhao X.-K., World Journal of Gastroenterology 2014, 20, 14875-14883);
  (c) relaxin and relaxin-like peptides, preferably relaxin-1 or 2 (see for example Zhou et al., Drug Design, Development and Therapy 2015, 9, 4599-4611);
  (d) lysyl oxidase (LOX) inhibitor beta-aminoproprionitrile (BAPN) (see for example Erler et al., Nature 2006, 440, 1222-1226); and
  (e) interleukin-7 (IL-7) for the treatment of lymph node fibrosis (see for example Fletcher et al., (2015 Nature Reviews Immunology, 15(6), 350-361);

Further preferred embodiments for practicing the present invention are directed to a composition, wherein the therapeutic agent is an immune modulating agent, preferably selected from the group consisting of
  (a) interleukin-12 (11-12) treatment to stimulate the immune system (see for example, Cicchelero, L., et al. (2016), Vet Comp Oncol.)
  (b) inhibitors that target the EGFR signaling cascade for the treatment of cancer (see for example, Datta, J., et al. (2015), Breast Cancer Res 17: 71).
  (c) myelin oligodendrocyte glycoprotein peptide sequence 35-55 for the treatment of multiple sclerosis (see for example, Getts, D. R., et al., Trends in Immunology, 2015, 36(7), 419-427).
  (d) siRNAs for the treatment of (auto)immune diseases and immune modulation (see for example, Katakowski, J. A., et al. (2016), Mol Ther 24(1): 146-155).
  (e) miRNAs for the treatment of (auto)immune diseases and immune modulation (see for example, Getts, D. R., et al., Trends in Immunology, 2015, 36(7), 419-427)
  (f) gene editing machinery to modulate immune cell functions (see for example, Getts, D. R., et al., Trends in Immunology, 2015, 36(7), 419-427).
  (g) cancer vaccines for cancer immune therapy (see for example, Grivas, P., et al. (2017), Ann Oncol 28(4): 680-682).
  (h) Sipuleucel-T, a dendritic cell-based vaccine to treat cancer. Other molecules can include PSA-TRICOM, ipilimumab, and chimeric antigen receptor T cell therapy (see for example, Yeku, O. and S. F. Slovin (2016), Cancer J 22(5): 334-341).
  (i) antibodies to enhance the anti-tumor response of the immune system by targeting immune regulatory pathways, for example, those that target immune checkpoints, such as anti-CTLA-4, anti-PD1 and anti-PD-L1 antibodies (for example, see Diesendruck, Y. and I. Benhar (2017), Drug Resist Updat 30: 39-47; D'Errico, G., et al. (2017), Clin Transl Med 6(1): 3); Xia, B. and R. S. Herbst (2016), Immunotherapy 8(3): 279-298; Topalian, S. L., et al. (2016), Nat Rev Cancer 16(5): 275-287; Marrone, K. A. and J. R. Brahmer (2016), Cancer J 22(2): 81-91.), also including molecules for immune-checkpoint blockade of cytotoxic T lymphocyte antigen-4 and programed death-1 emerged as promising strategies to activate antitumor cytotoxic T cell responses (see for example, Swart, M., et al. (2016), Front Oncol 6: 233; Papaioannou, N. E., et al. (2016), Ann Transl Med 4(14): 261), or TAM Family Receptors (see for example, Paolino, M. and J. M. Penninger (2016), Cancers (Basel) 8(10)), also antibodies that that block the B7 family of immune checkpoints (PD-L1, PD-L2, B7-H3, B7x and HHLA2 (see for example, Janakiram, M., et al. (2016), Immunotherapy 8(7): 809-819).
  (j) HDAC inhibitors to alter the epigenetic regulation of the immune system (see for example, Hull, E. E., et al. (2016), Biomed Res Int 2016: 8797206).

Further preferred embodiments are directed to a composition of the present invention, wherein the composition further comprises nanocarriers, preferably selected from the group consisting of particles, vesicles, liposomes and micelles (see for example Bertrand N. et al., Advanced Drug Delivery Reviews 2014, 66, 2-25).

In a second aspect, the present invention is directed to a nucleic acid encoding a fusion polypeptide comprising (i) at least one fibronectin binding polypeptide (FnBP) linked to (ii) at least one diagnostic or therapeutic polypeptide agent.

Hence, the FnBP and the agent form a fusion polypeptide, wherein the FnBP and the agent may be separated by further bridging amino acids and the fusion protein may also comprise further amino acids at the C-terminus or N-terminus.

In a preferred embodiment, the nucleic acid encoding the fusion polypeptide of the present invention is one, wherein the nucleic acid sequence encoding the at least one fibronectin binding polypeptide (FnBP) comprises a nucleic acid sequence selected from the group consisting of:
(a) nucleic acid sequences selected from the group consisting of SEQ ID NOs: 148 to 294, preferably SEQ ID NOs: 264 to 294 more preferably SEQ ID NOs: 288, 290 and 292;
(b) nucleic acid sequences having at least 80 or 90% identity, preferably at least 95% identity, more preferred at least 98% identity with a nucleic acid sequence listed in SEQ ID NOs: 148 to 294, preferably SEQ ID NOs: 264 to 294 more preferably SEQ ID NOs: 288, 290 and 292, preferably over the whole sequence;
(c) nucleic acid sequences that hybridize to a nucleic acid sequence of (a) or (b) under stringent conditions;
(d) fragments of any of the nucleic acid sequences (a) to (c), that hybridize to a nucleic acid sequence of (a) or (b) under stringent conditions; and
(e) a nucleic acid sequence, wherein said nucleic acid sequence is derivable by substitution, addition and/or deletion of one of the nucleic acids of (a) to (d) that hybridizes to a nucleic acid sequence of (a) or (b) under stringent conditions.

The term "% (percent) identity" as known to the skilled artisan and used herein in the context of nucleic acids indicates the degree of relatedness among two or more nucleic acid molecules that is determined by agreement among the sequences. The percentage of "identity" is the result of the percentage of identical regions in two or more sequences while taking into consideration the gaps and other sequence peculiarities.

The identity of related nucleic acid molecules can be determined with the assistance of known methods. In general, special computer programs are employed that use algorithms adapted to accommodate the specific needs of this task. Preferred methods for determining identity begin with the generation of the largest degree of identity among the sequences to be compared. Preferred computer programs for determining the identity among two nucleic acid sequences comprise, but are not limited to, BLASTN (Altschul et al., (1990) J. Mol. Biol., 215:403-410) and LALIGN (Huang and Miller, (1991) Adv. Appl. Math., 12:337-357). The BLAST programs can be obtained from the National Center for Biotechnology Information (NCBI) and from other sources (BLAST handbook, Altschul et al., NCB NLM NIH Bethesda, Md. 20894).

The nucleic acid molecules according to the invention may be prepared synthetically by methods well-known to the skilled person, but also may be isolated from suitable DNA libraries and other publicly available sources of nucleic acids and subsequently may optionally be mutated. The preparation of such libraries or mutations is well-known to the person skilled in the art.

In a further preferred embodiment, the nucleic acid of the present invention is a DNA, RNA or PNA, preferably DNA or PNA, more preferably DNA.

In some instances, the present invention also provides novel nucleic acids encoding the FnBPs of the present invention characterized in that they have the ability to hybridize to a specifically referenced nucleic acid sequence, preferably under stringent conditions. Next to common and/or standard protocols in the prior art for determining the ability to hybridize to a specifically referenced nucleic acid sequence under stringent conditions (e.g. Sambrook and Russell, (2001) Molecular cloning: A laboratory manual (3 volumes)), it is preferred to analyze and determine the ability to hybridize to a specifically referenced nucleic acid sequence under stringent conditions by comparing the nucleotide sequences, which may be found in gene databases (e.g. the National Center for Biotechnology Information (NCBI) and the Joint Genome Institute (JGI)) with alignment tools, such as e.g. the above-mentioned BLASTN (Altschul et al., (1990) J. Mol. Biol., 215:403-410), LALIGN alignment tools and multiple alignment tools such as e.g. CLUSTALW (Sievers F et al., (2011) Mol. Sys. Bio. 7: 539), MUSCLE (Edgar., (2004) Nucl. Acids Res. 32:1792-7) or T-COFFEE (Notredame et al., (2000) J of Mol. Bio 302 1: 205-17).

Most preferably, the ability of a nucleic acid of the present invention to hybridize to a nucleic acid, e.g. those listed in any of SEQ ID NOs 148 to 294, preferably 264-294, more preferably at least one of SEQ ID NOs: 288, 290, 292, is confirmed in a Southern blot assay under the following conditions: 6× sodium chloride/sodium citrate (SSC) at 45° C. followed by a wash in 0.2×SSC, 0.1% SDS at 65° C.

The term "nucleic acid encoding a polypeptide" as used in the context of the present invention is meant to include allelic variations and redundancies in the genetic code.

Preferably, the nucleic acid of the instant invention encodes a fibronectin binding polypeptide that binds specifically to at least one of $FnI_{1-6}$, $FnII_{1-2}$, $FnI_{7-9}$ or $FnIII_{7-15}$ preferably subunits $FnI_{1-5}$, $FnII_{1-2}$, $FnIII_{7-11}$, more preferably subunits $FnI_{2-5}$.

In a further preferred embodiment, the nucleic acid of the present invention is one, wherein the diagnostic polypeptide agent is selected from the group consisting of fluorescent proteins, preferably fluorescent proteins eGFP, YFP, RFP, mOrange, mCherry, flavin-based fluorescent proteins (FbFPs), more preferably RFP and mCherry.

In yet another preferred embodiment, the nucleic acid according to the present invention is one, wherein the therapeutic polypeptide agent is selected from the group consisting of bone morphogenic proteins, Interleukins, Interferons, Relaxin, prosaposin-derived thrombospondin-1 inducing peptides (see for example US patent 2015/0320825 A1), preferably bone morphogenic protein-7 (BMP-7), Interleukin-2 (IL-2), Interleukin-7 (IL-7), Interferon-γ, tumor necrosis factor (TNF), Relaxin-1, Relaxin-2, and DWLPK and DWLP prosaposin-derived peptides, more preferably BMP-7, IL-7, IL-2 and TNF.

Both, the diagnostic and the therapeutic polypeptide agent can be a polypeptide selected from the list of diagnostic and therapeutic agents described above.

The nucleic acid of the present invention is preferably operably linked to a promoter that governs expression in suitable vectors and/or host cells producing the polypeptides of the present invention in vitro or in vivo.

Suitable promoters for operable linkage to the isolated and purified nucleic acid are known in the art. In a preferred embodiment the nucleic acid of the present invention is one that is operably linked to a promoter selected from the group consisting of the *Pichia pastoris* GAP promoter, AUG1 promoter, FLD1 promoter and AOX1 promoter (see for example *Pichia* Expression Kit Instruction Manual, Invitrogen Corporation, Carlsbad, Calif.), the *Saccharomyces cerevisiae* GAL1, ADH1, GAP, ADH2, MET25, GPD, CUP1 or TEF promoter (see for example Methods in Enzymology, 350, 248, 2002), the Baculovirus polyhedrin p10 or ie1 promoter (see for example Bac-to-Bac Expression Kit Handbook, Invitrogen Corporation, Carlsbad, Calif., and Novagen Insect Cell Expression Manual, Merck Chemicals Ltd., Nottingham, UK), the Lentivirus CMV, UbC, EF1α, or MSCV promoter (see for example System Biosciences, Mountain View, Calif., USA), the Adenovirus CMV promoter (see for example ViraPower Adenoviral Expression System, Life Technologies, Carlsbad, Calif., USA), the Simian virus 40 promoter SV40, the *E. coli* T7, araBAD, rhaP BAD, tetA, lac, trc, tac or pL promoter (see Applied Microbiology and Biotechnology, 72, 211, 2006), the *B. subtilis*, vegI, vegII, σA, $P_{grac}$, $P_{giv}$, manP or P43 promoter (see Applied Microbiology and Biotechnology, 72, 211, 2006), the plant CaMV35S, ocs, nos, Adh-1, Tet promoters (see e.g. Lau and Sun, Biotechnol Adv. 2009, 27, 1015-22) or inducible promoters for mammalian cells as described in Sambrook and Russell (2001).

Hence, in a further aspect, the present invention is directed to a recombinant vector comprising a nucleic acid of the invention, preferably a viral or episomal vector, preferably a baculovirus vector, lentivirus vector, adenovirus vector, yeast or bacterial episomal vector.

The selection of a suitable vector and expression control sequences as well as vector construction are within the ordinary skill in the art. Preferably, the viral vector is a lentivirus vector (see for example System Biosciences, Mountain View, Calif., USA), adenovirus vector (see for example ViraPower Adenoviral Expression System, Life Technologies, Carlsbad, Calif., USA), baculovirus vector such as bacmid (or see for example Bac-to-Bac Expression Kit Handbook, Invitrogen Corporation, Carlsbad, Calif.), the pcDNA, pVITRO, pSV and pCMV series of plasmid vectors, vaccinia and retroviral vectors (see for example Hruby, D. E. (1990). Vaccinia virus vectors: new strategies for producing recombinant vaccines. Clinical Microbiology Reviews, 3(2), 153-170.), bacterial vector pGEX and pET (or see for example Novagen, Darmstadt, Germany)) or yeast vector pPIC (or see for example ATCC Manassas, Va.). Vector construction, including the operable linkage of a coding sequence with a promoter and other expression control sequences, is within the ordinary skill in the art.

In yet another aspect, the present invention is directed to a host cell comprising a nucleic acid or a vector of the invention and preferably producing peptides of the invention. Preferred host cells for producing the polypeptide of the invention are selected from the group consisting of yeast cells preferably *Saccharomyces cerevisiae* (see for example Methods in Enzmology, 350, 248, 2002), *Pichia pastoris* cells (see for example *Pichia* Expression Kit Instruction Manual, Invitrogen Corporation, Carlsbad, Calif.)], bacterial cells preferably *E. coli* cells (BL21(DE3), K-12 and derivatives) (see for example Applied Microbiology and Biotechnology, 72, 211, 2006) or *B. subtilis* cells (1012 wild type, 168 Marburg or WB800N)(see for example Westers et al., (2004) Mol. Cell. Res. Volume 1694, Issues 1-3 P: 299-310), plant cells, preferably *Nicotiana tabacum* or *Physcomitrella patens* (see e.g. Lau and Sun, Biotechnol Adv. 2009 May 18. [electronic publication ahead of print]), NIH-3T3 mammalian cells (see for example Sambrook and Russell, 2001), Human Embryonic Kidney 293 cells (HEK 293, adherent or in suspension, also large T antigen transformed HEK 293T cells), Chinese hamster ovary (CHO) cells, COS cells, and insect cells, preferably sf9 insect cells (see for example Bac-to-Bac Expression Kit Handbook, Invitrogen Corporation, Carlsbad, Calif.).

A further aspect of the present invention relates to a kit of parts comprising at least one fibronectin binding polypeptide (FnBP) and at least one diagnostic or therapeutic agent, and optionally one or more chemical agents for linking the fibronectin binding polypeptide (FnBP) to the diagnostic or therapeutic agent.

In a preferred embodiment, the kit of parts of the invention comprises at least one fibronectin binding polypeptide (FnBP) and at least one diagnostic or therapeutic agent, wherein the fibronectin binding polypeptide (FnBP) and the at least one diagnostic or therapeutic agent comprise at least one moiety each that link the fibronectin binding polypeptide (FnBP) to the at least one diagnostic or therapeutic agent under physiological conditions.

In a further preferred embodiment, the kit of parts comprises an FnBP and a diagnostic or therapeutic agent separately, both of which components have binding affinity towards each other, preferably due to complementary nucleic acid sequences on each component that will specifically link the components to each other upon contact under suitable conditions for hybridization in vitro or in vivo (PAINT technology), e.g. in blood.

Another aspect of the present invention is directed to a use of a composition or a kit of parts according to the invention for binding at least one diagnostic or therapeutic agent to fibronectin.

In a preferred embodiment, the composition or kit of parts of the invention are for use in the therapeutic or prophylactic treatment of a disease, preferably a disease associated with pathogenic fibronectin accumulation, more preferable a disease associated with abnormal accumulation of soluble plasma Fn and/or insoluble ECM Fn.

The term "pathological fibronectin accumulation" as used herein, refers to any disease or condition in which the amount of fibronectin deposited at a given site is higher than in a healthy state. For example, pathological fibronectin accumulation is found regularly in fibrosis or cancer.

The term "immune cell modulation" or "modulating immune cells" as used herein refers to inducing, enhancing or suppressing an immune response in a cell, preferably in an immune effector cell, e.g. in lymphocytes, macrophages, dendritic cells, natural killer cells, T-cells, cytotoxic T lymphocytes, B-cells etc. An effect of modulation immune cells can be, e.g., the targeting of abnormal antigens expressed on the surface of, e.g., tumor cells.

As used herein, the term "fibrosis" can refer to any disease characterized by fibrosis, including but not limited to systemic sclerosis, multifocal fibrosclerosis, sclerodermatous graft-vs-host-disease, nephrogenic systemic fibrosis, organ specific fibrosis, mediastinal fibrosis, myelofibrosis, retroperitoneal fibrosis, progressive massive fibrosis, Crohn's Disease, Keloid, arthrofibrosis, Peyronie's Disease, Dupuytren's Contracture, adhesive capsulitis, and the like. Illustrative organ specific fibrosis include, but are not limited to, pulmonary fibrosis, pulmonary hypertension, cystic fibrosis, asthma, chronic obstructive pulmonary disease, liver fibrosis, kidney fibrosis, fibrosis of the pancreas, non-alcoholic steatohepatitis (NASH), lymph node fibrosis, corneal fibrosis, fibrous cartilage, endometriosis, and the like. Many fibrosis diseases, disorders or conditions have disordered and/or exaggerated deposition of extracellular matrix in affected tissues. Fibrosis may be associated with inflammation, occur as a symptom of underlying disease, and/or caused by surgical procedure or injuries with limited wound healing capacities.

A "cancer" or "tumor" as used herein refers to an uncontrolled growth of cells which interferes with the normal functioning of the bodily organs and systems. Examples of cancer include, but are not limited to B-cell lymphomas (Hodgkin's lymphomas and/or non-Hodgkin's lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma and other skin cancers, head and neck cancer (preferably head and neck squamous cell carcinoma), brain cancer, and prostate cancer, including but not limited to androgen-dependent prostate cancer and androgen-independent prostate cancer.

In a preferred embodiment, the composition or kit of parts of the invention is for use in the therapeutic or prophylactic treatment of a disease selected from the group consisting of fibrosis, cancer, lymphedema, immune diseases, autoimmune diseases, atherosclerotic plaques, preferably systemic sclerosis, pulmonary fibrosis, liver fibrosis, kidney fibrosis, breast cancer, head and neck squamous cell carcinoma, prostate cancer, renal cancer, pancreatic cancer and lung cancer, more preferably non-small lung cell cancer.

In further aspect, the present invention is directed to a use of the composition or kit of parts of the invention in the manufacture of a medicament for the treatment or prophylaxis of a disease, preferably a disease associated with abnormal fibronectin accumulation, more preferably a disease selected from the group consisting from the group consisting of fibrosis, cancer, lymphedema, atherosclerotic plaques, immune diseases and autoimmune diseases, preferably systemic sclerosis, pulmonary fibrosis, liver fibrosis, kidney fibrosis, breast cancer, head and neck squamous cell carcinoma, prostate cancer, renal cancer, pancreatic cancer, lung cancer and autoimmune diseases, more preferably non-small lung cell cancer, diabetes type 1, graves diseases, multiple sclerosis and rheumatoid arthritis.

In the above respect the present invention also relates to a pharmaceutical composition comprising as active substance at least one fibronectin binding polypeptide (FnBP) linked to at least one diagnostic or therapeutic agent, one or more polypeptides, nucleic acids, a recombinant vector and/or a host cell according to the invention, optionally combined with conventional excipients and/or carriers.

For therapeutic or prophylactic use the composition, polypeptides, nucleic acids, recombinant vectors and/or host cells of the invention may be administered in any conventional dosage form in any conventional manner. Routes of administration include, but are not limited to, intravenously, intraperitoneally, intramuscularly, subcutaneously, intrasynovially, by infusion, sublingually, transdermally, orally, topically, or by inhalation. The preferred modes of administration are by infusion and intravenous, or inhalation administration for treating for lung fibrosis.

The compounds for use in the present invention may be administered alone or in combination with adjuvants that enhance stability, facilitate administration of pharmaceutical compositions containing them, provide increased dissolution or dispersion, increase inhibitory activity, provide adjunct therapy, and the like, including other active ingredients. Advantageously such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference in this regard may be made to Cappola et al.: U.S. patent application Ser. No. 09/902,822, PCT/US 01/21860 und U.S. provisional application No. 60/313,527, each incorporated by reference herein in their entirety. The optimum percentage (w/w) of a compound or composition of the invention may vary and is within the purview of those skilled in the art. Alternatively, the compounds may be administered separately (either serially or in parallel). Separate dosing allows for greater flexibility in the dosing regimen.

As mentioned above, dosage forms of the compounds for use in the present invention include pharmaceutically acceptable carriers and adjuvants known to those of ordinary skill in the art. These carriers and adjuvants include, for example, ion exchangers, alumina, aluminium stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical *Dosage Forms and Drug Delivery Systems*, $5^{th}$ ed., Lea and Febiger (1990)). Dosage levels and requirements are well-recognized in the art and may be selected by those of ordinary skill in the art from available methods and techniques suitable for a particular patient. In some embodiments, dosage levels range from about 0.5 µg-100 mg/dose for a 70 kg patient. Although one dose per day may be sufficient, up to 5 doses per day may be given. For oral doses, up to 2000 mg/day may be required. For radionuclide therapy a dose every 4 to 8 week for 2 to 8 times may be applicable. Reference in this regard may also be made to U.S. provisional application No. 60/339,249. As the skilled artisan will appreciate, lower or higher doses may be required depending on particular factors. For instance, specific doses and treatment regimens will depend on factors such as the patient's general health profile, the severity and course of the patient's disorder or disposition thereto, and the judgment of the treating physician. For example, the compounds of the present invention can be administered the same way as other peptide-based medicaments.

Compounds for use in the present invention may be formulated into capsules the same way other peptide-based medicaments are formulated. Each capsule may contain 100 to 500, preferably 150 to 300, more preferably 200 to 250 mg of a compound of the invention. For example, non-medicinal ingredients in capsules for the compounds of the present invention are—capsule shell: D&C yellow No. 10, FD&C blue No. 1, FD&C red No. 3, FD&C yellow No. 6, gelatin and titanium dioxide. Bottles of 100. (see also Martindale: the complete drug reference, $34^{th}$ Edition, 2005, Pharmaceutical Press, p 612.)

In view of the above, the present invention is also directed to a method for treating a subject suffering from a disease associated with pathological fibronectin accumulation, preferably suffering from a disease selected from the group consisting of fibrosis, cancer, lymphedema, immune diseases, autoimmune diseases and atherosclerotic plaques, preferably systemic sclerosis, pulmonary fibrosis, liver fibrosis, kidney fibrosis, breast cancer, head and neck squamous cell carcinoma, prostate cancer, renal cancer, pancreatic cancer and lung cancer, more preferably non-small lung cell cancer, diabetes type 1, graves diseases, multiple sclerosis and rheumatoid arthritis, comprising the steps of:
  (a) providing a composition or kit of parts of the instant invention comprising a therapeutic agent and optionally further physiologically acceptable excipients and diluents in a physiologically effective amount, (b) administering the composition or kit of parts of (a) to the subject in need thereof, preferably by intravenous administration.

In a further aspect, the present invention reads on a composition or kit of parts according to the invention for use in the diagnosis of a disease, preferably a disease associated with pathologic fibronectin accumulation. Preferably the disease to be diagnosed is selected from the group consisting of fibrosis, cancer, lymphedema, immune diseases, autoimmune diseases and atherosclerotic plaques, preferably systemic sclerosis, pulmonary fibrosis, liver fibrosis, cornea fibrosis, fibrous cartilage, kidney fibrosis, breast cancer, head and neck squamous cell carcinoma, prostate cancer, renal cancer, pancreatic cancer and lung cancer, more preferably non-small lung cell cancer, diabetes type 1, graves diseases, multiple sclerosis and rheumatoid arthritis.

The invention also provides for the use of a composition or kit of parts of the invention in the manufacture of a diagnostic composition for the diagnosis of a disease, preferably a disease associated with pathological fibronectin accumulation, more preferably a disease selected from the group consisting of fibrosis, cancer, lymphedema, immune diseases, autoimmune diseases and atherosclerotic plaques, preferably systemic sclerosis, pulmonary fibrosis, liver fibrosis, kidney fibrosis, breast cancer, head and neck squamous cell carcinoma, prostate cancer, renal cancer, pancreatic cancer and lung cancer, more preferably non-small lung cell cancer, diabetes type 1, graves diseases, multiple sclerosis and rheumatoid arthritis.

Furthermore, the invention includes a method for the diagnosis of a disease associated with pathological fibronectin accumulation in a subject, preferably a disease selected from the group consisting of fibrosis, cancer, lymphedema, immune diseases, autoimmune diseases and atherosclerotic plaques, preferably systemic sclerosis, pulmonary fibrosis, liver fibrosis, kidney fibrosis, cornea fibrosis, cartilage fibrosis, breast cancer, head and neck squamous cell carcinoma, prostate cancer, renal cancer, pancreatic cancer and lung cancer, more preferably non-small lung cell cancer, diabetes type 1, graves diseases, multiple sclerosis and rheumatoid arthritis comprising the steps of:
  (a) providing a composition or kit of parts according to the invention comprising a diagnostic agent and optionally further physiologically acceptable excipients and diluents in a physiologically effective amount,
  (b) administering the composition or kit of parts of (a) to the subject in need thereof, preferably by intravenous administration, and
  (c) identifying pathological fibronectin accumulation by accumulation of the fibronectin binding peptide (FnBP) in said composition.

The invention has been described generally and also with emphasis upon preferred embodiments and will be further illustrated by the following examples, none of which should not be construed to limit the scope of the invention beyond the scope of the appended claims.

DETAILED DESCRIPTION OF THE INVENTION

Examples

Example 1: General Material and Methods

Fn Isolation and Labelling

Fn was isolated from human plasma (Zürcher Blutspendedienst SRK Switzerland) using gelatin sepharose chromatography, as previously described (E. Engvall and E. Ruoslahti, "Binding of soluble form of fibroblast surface protein, fibronectin, to collagen," *Int. J. Cancer*, vol. 20, no. 1, pp. 1-5, July 1977). Plasma was thawed and passed through a PD-10 column (GE Healthcare, Little Chalfont, UK) to remove aggregates. Effluent was collected and run through a gelatin sepharose column. After washing the column Fn was eluted from the gelatin column with a 6 M urea solution. Unlabelled Fn was then rebuffered to PBS before usage. For single labelling Fn was denatured in a 4 M guanidinium hydrochloride (GdnHCI, Applichem, Darmstadt, Germany) solution to open up cryptic cysteines at FnIII7 and FnIII15. Fn was incubated with an excess of Cy5 maleimide dye (GE Healthcare, Little Chalfont, UK) and separated from the dye using a PD-10 column.

Synthesis and Labelling of FnBPA5 and Derivatives

Figure 1:
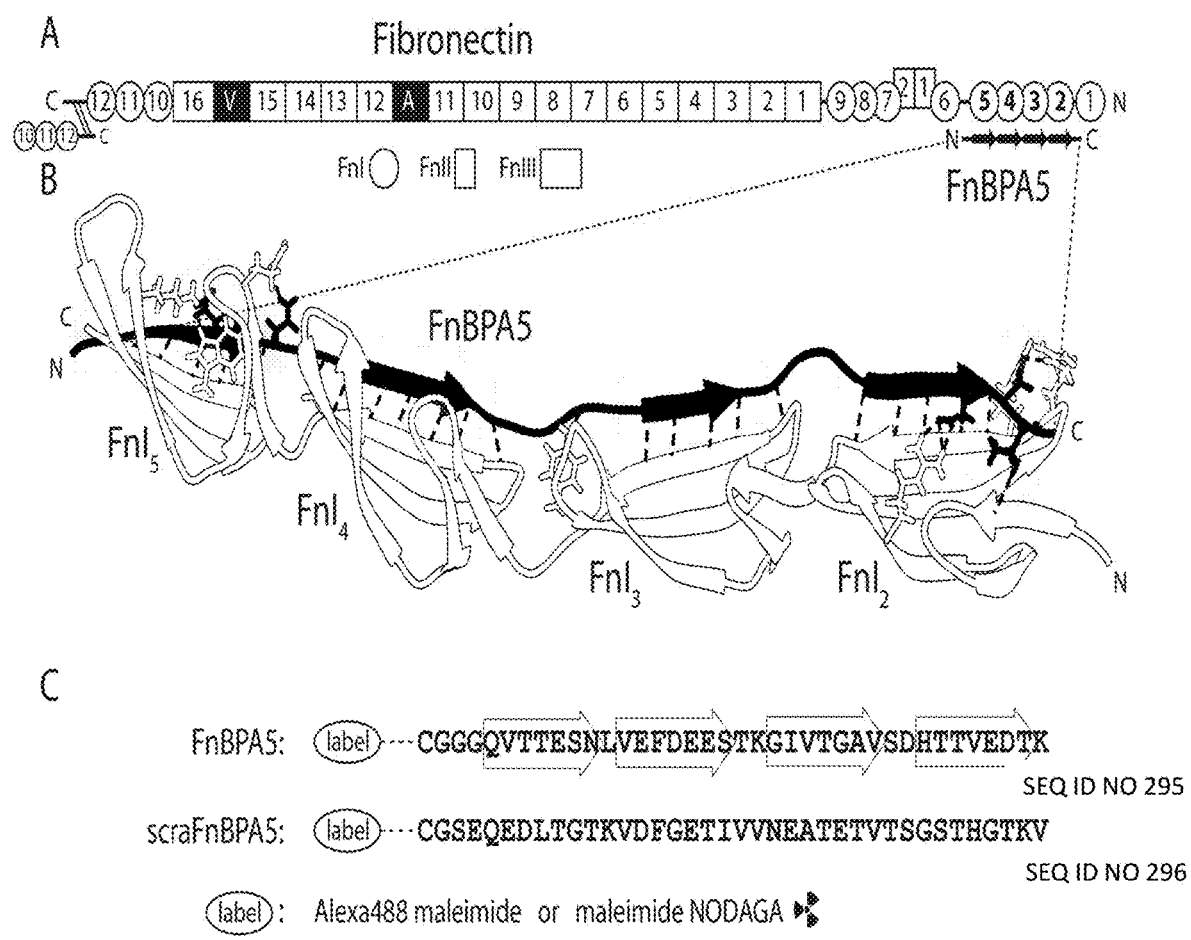
FIG. 1 shows binding of FnBPA5 peptide (solid black) to extracellular matrix protein fibronectin on different length scales. (A) Schematic representation of the modular structure of Fn consisting of three different types of modules with FnBPA5 binding to the $FnI_2$-$FnI_5$ domains close to the N-terminus of the Fn monomer. (B) Structure of FnBPA5 bound to $FnI_2$-$FnI_5$ via addition of an antiparallel beta-sheet to each FnI module. (C) Schematic representation of bacterial derived fibronectin binding peptide sequences (FnBPA5 (SEQ ID NO 295) and scrambled derivative (SEQ ID NO 296)).

Peptides were commercially synthesized (Pichem, Graz, Austria) with a spacer of three glycines and a cysteine residue at the N-terminus of the original peptide sequence from *S. aureus* for further labelling with a radioligand or fluorophore. FnBPA5 was labelled using a fluorophore attached to a maleimide residue or conjugated with a maleimide NODAGA complexing unit for further radiolabeling with $^{111}$In. Peptides were HPLC purified after conjugation to remove remaining free binding residues. A negative control of FnBPA5 with scrambled sequence was designed to investigate whether FnBPA5 binding to Fn is sequence specific. All peptide sequences are shown in FIG. 1C (SEQ ID NOs 295 and 296). Lyophilized peptides were dissolved in water with 10% DMF and stored at −20° C. upon further usage.

In Vitro Fn Fiber Assay

Manually pulled Fn fibers were used as a model system for fibrillar Fn as described previously (W. C. Little, M. L. Smith, U. Ebneter, and V. Vogel, "Assay to mechanically tune and optically probe fibrillar fibronectin conformations from fully relaxed to breakage," *Matrix Biology*, vol. 27, no. 5, pp. 451-461, June 2008). Fibers containing 5% of photolabeled Fn-Cy5 were deposited onto a stretchable silicone sheet, relaxed to half of their original length, corresponding to a total 7% molecular strain and after a blocking step with 4% bovine serum albumin in PBS, they were incubated with different concentrations of Alexa488 fluorescently labeled FnBPA5 to obtain a binding curve.

Confocal Microscopy

Manually pulled Fn fiber samples were imaged with an Olympus FV1000 confocal microscope using a 40× water immersion objective with a numerical aperture of 0.9. Alexa488-FnBPA5 and Fn-Cy5 channels were imaged with a 512×512 pixel resolution and photomultiplier tube voltage and laser powers were kept constant within an experiment.

Fibroblast ECM samples (FIG. 2C) were acquired with the same microscope using an oil immersion 1.45 NA 60× objective with a pixel resolution of 1024×1024.

Image Analysis

Images were analyzed using Fiji-ImageJ and Matlab (MathWorks, Natick, Mass., USA). For the Fn fiber affinity study the pixelwise ratio of FnBPA5-Alexa488 signal intensity divided by Fn-Cy5 intensity was calculated for each fiber using a custom made Matlab script. Dark current values were subtracted from images and pixels with intensities below a cutoff threshold and at saturation were excluded from analysis. Approximately 10 fibers were imaged per experimental condition and each of these conditions was done in triplicate. Binding ratio of 10 µM FnBPA5-Alexa488 concentration was set to 1 and all other points were normalized to this reference point. Data points were fit using the Hill model assuming non-cooperative binding (using the below equation) and plot using Origin.

$$\theta = \frac{[L]}{K_d + [L]}$$

$\theta$ = ratio of occupied binding sites divided by total binding sites;

$[L]$ = free (unbound ligand concentration;

$K_d$ = dissociation constant.

Radiolabelling of FnBPA5-NODAGA and Scrambled FnBPA5-NODAGA

The fibronectin binding peptide (FnBPA5) and its scrambled derivative (scraFnBPA5) were purchased from Peptide Specialty Laboratories GmbH (Heidelberg, Germany) conjugated with a malemide NODAGA. The compounds were dissolved in TraceSELECT® Water (Sigma Aldrich) to a final concentration of 0.25 mM. For the labelling, 14 nmol of each peptide were radiolabelled in 0.5 M ammonium acetate pH 5.5 by adding 80 MBq $^{111}$InCl$_3$ (Mallincrodt, Wollerau, Switzerland) followed by a 30 minute incubation step at 50° C. Quality control was performed by radio-HPLC (Varian Prostar, Santa Clara, USA); column Dr. Maisch Reprospher (Ammerbuch, Germany) 300 C18-TN, 4.6 cm×150 mm; 5 m with acetonitrile/water gradient starting with 15% acetonitrile up to 95% over 15 minutes with a flow rate of 1 mL/min.

Tumor Model

PC-3 cells (human prostate carcinoma cell line, ACC-465, DSMZ, Braunschweig, Germany) were cultured in Roswell Park Memorial Institute 1640 medium (Amimed, Bioconcept, Switzerland). Cells were cultured as monolayers at 37° C. in a humidified atmosphere containing 5% $CO_2$.

In vivo experiments were approved by the local veterinarian department and conducted in accordance with the Swiss law for animal protection. The 3-5 weeks-old female CD1 nude mice were purchased from Charles River (Germany). After 5-7 days acclimatisation period, the tumor cells were subcutaneously inoculated in both shoulders of the mice (3*106-1*107 cells in 100-150 µL PBS per side). Experiments were performed 3-4 weeks after inoculation.

Statistical Analysis

Statistical analysis was performed using two-tailed type 3 t-test (Microsoft Excel). Statistical significance was assumed for p-values smaller than 0.05.

Figure 2A:
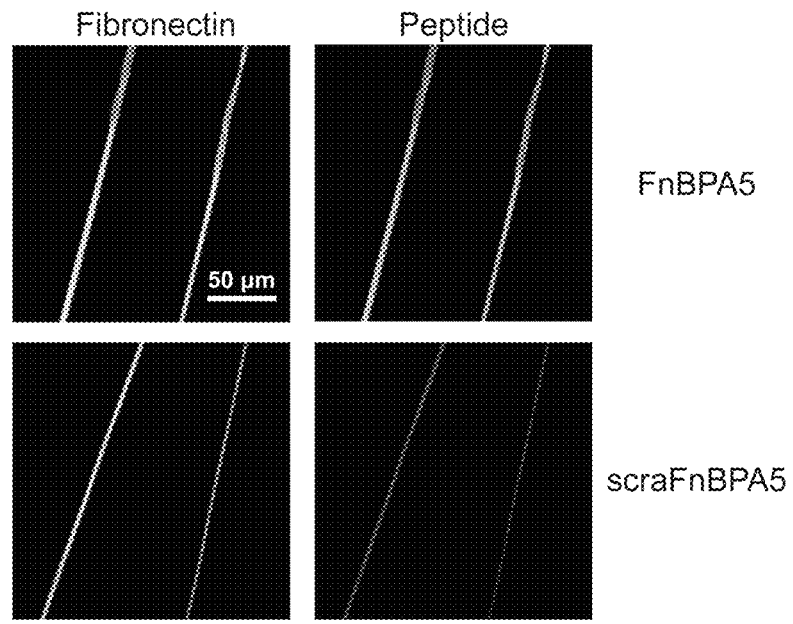
FIG. 2 shows in vitro binding studies of FnBPA5 and scrambled derivative to soluble and fibrillar Fn (A) Binding of FnBPA5 and scrambled derivative to manually pulled Fn fibers. Fn (left column) and peptide signal (right column) show specific peptide binding only for FnBPA5 and not for its scrambled derivative. (B) Quantification of FnBPA5 and scraFnBPA5 binding to Fn fibers showing a significantly higher binding of FnBPA5 compared to scrambled derivative. Data from 30 fibers from three independent experiments was analyzed. Shown error bars represent standard deviation, student-t-test was carried out to shown significance. (C) Fibroblast ECM was stained for fibronectin, FnBPA5 or scraFnBPA5, actin and cell nuclei. Representative images show specific binding of FnBPA5 to Fn whereas scraFnBPA5 unspecificly attached to the matrix. (D) Binding of FnBPA5 and scrambled FnBPA5 to soluble plasma Fn using anisotropy measurement, showing a $K_d$ of 75 nM for FnBPA5 and no specific binding of scrambled derivative. (E) Measurement of affinity of FnBPA5 to manually pulled relaxed Fn fibers, showing a $K_d$ of 28 nM.
Figure 2B:
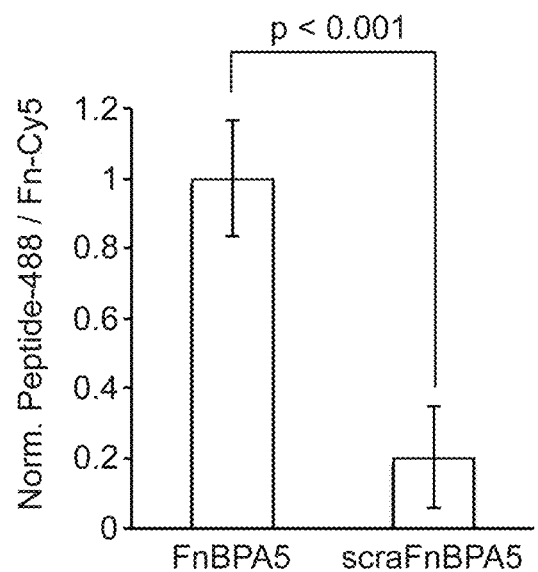

Example 2: Manually Pulled Fn Fiber System to Assess Binding Specificity and Binding Affinity of FnBPA5 or Other FnBPs To assess binding constant of Alexa488-FnBPA5 and of its scrambled analogue to Fn fibers a fiber stretch assay as described above and before (Little et al., *Matrix Biology*, vol. 27, no. 5, pp. 451-461, June 2008) was used. Fn fibers are manually pulled from a Fn solution containing 5% fluorophore labeled Fn and deposited onto a silicone membrane. Silicone membranes can then be stretched or relaxed to desired mechanical strain state. Confocal microscopy images of manually pulled Fn fibers exposed to FnBPA5 peptide in solution are shown in FIG. 2A. FnBPA5 peptide was shown to bind to Fn much stronger than the scrambled control derivative, whose signal is within the background noise (FIG. 2A). This result is confirmed in the analysis and quantification of multiple fibers from several fields of view (FIG. 2B).

Figure 2C:
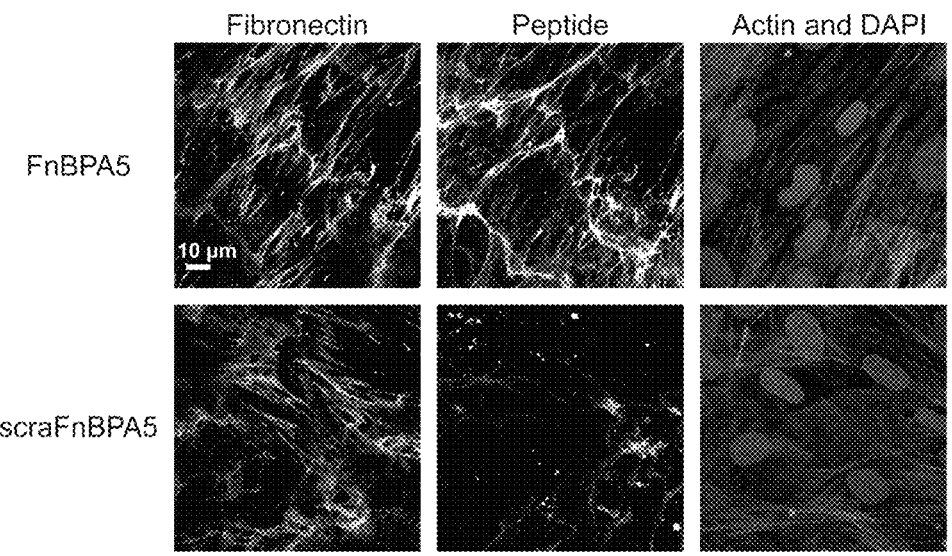
Figure 2D:
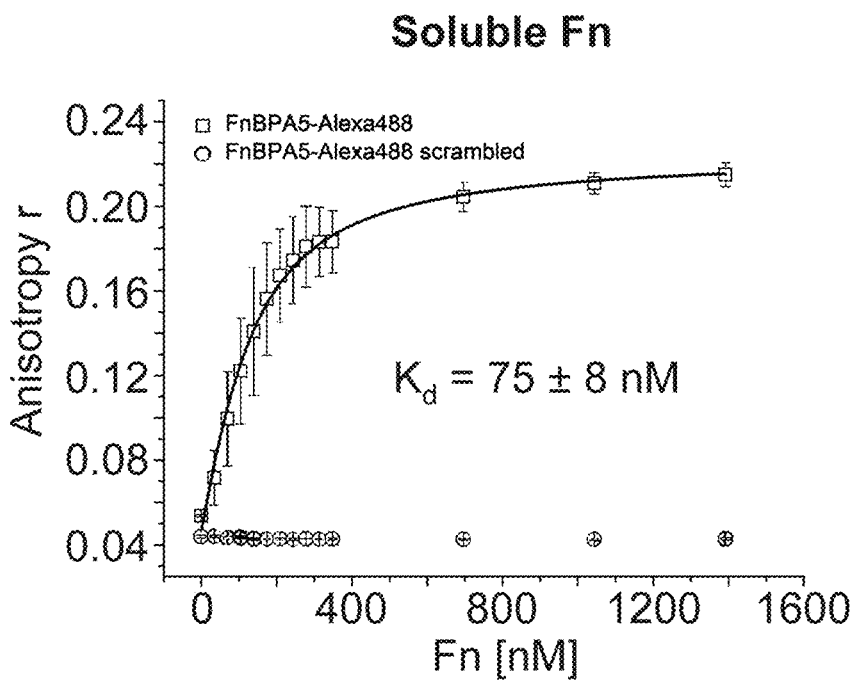
Figure 2E:
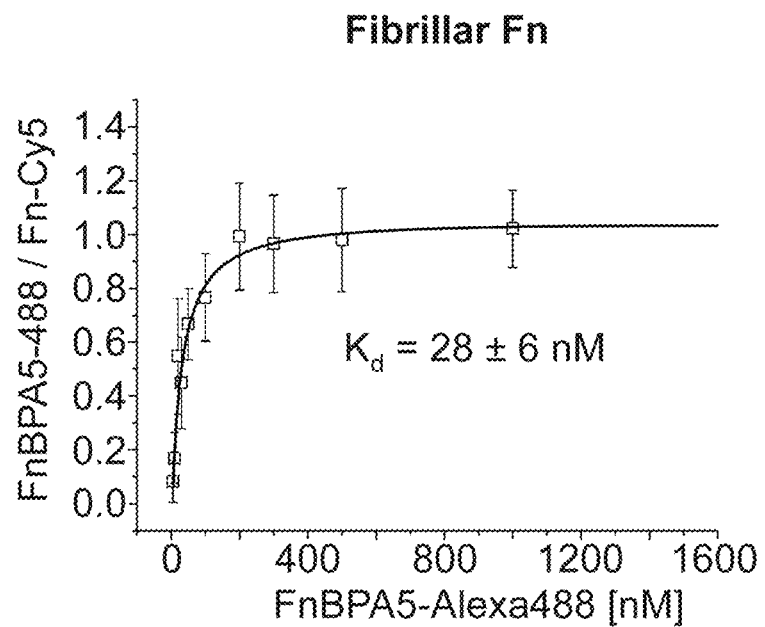

To measure a quantitative binding curve Fn fibers of equal mechanical strain were incubated with different concentrations of FnBPA5-Alexa488. Peptide fluorescence intensity normalized against the Cy5-intensity from the Fn-fibers for different peptide concentrations was assessed. Intensity ratio of 10 µM FnBPA5-488 was defined as saturated and all other intensity ratios were normalized with this factor. In FIG. 2E all points of the analysis are plotted and fit leading to a binding curve with a dissociation constant $K_d$ of 28 nM. Importantly, this affinity of FnBPA5 peptide to fibrillar Fn is of the same order of magnitude as those reported for the FnBPA5 peptide binding to N-terminal Fn fragments in solution ($K_d$=44.2 nM) (Meenan et al., *J. Biol. Chem.*, vol. 282, no. 35, pp. 25893-25902, August 2007) and also comparable to affinities reported for several antibodies that target ECM proteins and are in clinical use (Viti et al., *Cancer Research*, vol. 59, no. 2, pp. 347-352, January 1999).

Figure 6:
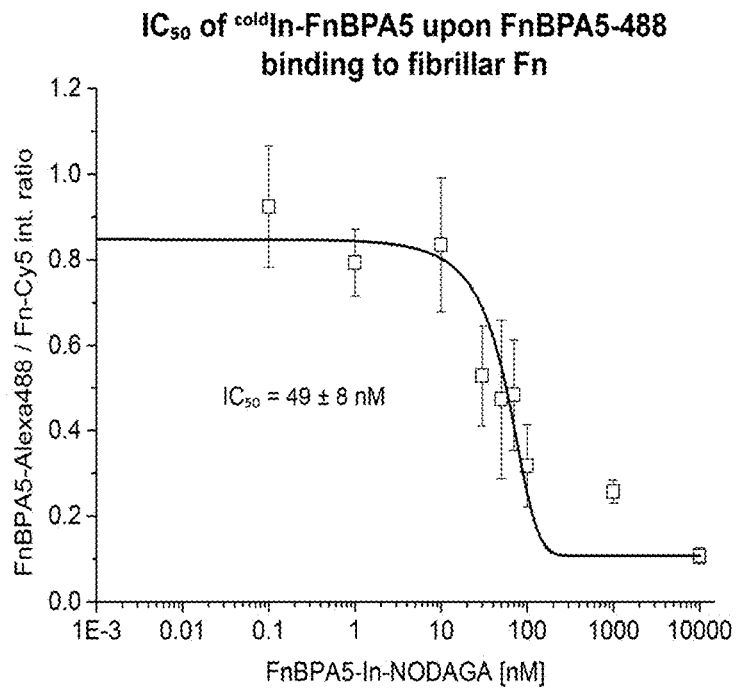
FIG. 6 shows $IC_{50}$ measurement of $^{nat}$In-FnBPA5. Relaxed Fn fibers were incubated with FnBPA5-Alexa488 peptide, washed and then incubated with different concentrations of FnBPA5-In to measure the concentration of competitor. At the midpoint between high and low plateau of the curve is the $IC_{50}$ value at 49 nM.

To assess whether the presence of the chelator for the radiolabeled $^{111}$In-isotope impairs FnBPA5 binding to manually pulled Fn fibers, a displacement assay was performed using $^{nat}$In-FnBPA5 (cold labeled) against FnBPA5-Alexa488. Extrapolated IC$_{50}$ value for $^{nat}$In-FnBPA5 of 49 nM (FIG. 6) show that the radiolabeling process did not affect binding properties of FnBPA5.

Example 3: Assessment of Binding of FnBPA5 or Other FnBPs to Fibrillar Fn in Cell Culture Matrices To ensure that such tight binding can be observed also in native extracellular matrix, Fn-rich ECM assembled by fibroblasts for 2 days was incubated for 1 hour with native or scrambled FnBPA5 prior to fixation and showed specific binding of FnBPA5 to fibrillar Fn, but not of the scrambled derivative (FIG. 2C). To achieve this, normal human dermal fibroblasts (PromoCell, Heidelberg, Germany) were cultured in alpha minimum essential medium (α-MEM) with 10% fetal bovine serum (FBS) from BioWest, Nuaillé, France, and split before reaching confluence. Cells were seeded onto Fn-coated 8-well chambered coverglasses (Lab-Tek, Nalgene Nunc, Thermo Scientific, Waltham, Mass., USA) at a density of 30×10$^3$ cells per cm$^2$ and allowed to attach to the surface before medium exchange to medium containing 50 µg/ml unlabeled Fn. Cells were cultured for 48 hours. Fibronectin was then stained using a rabbit polyclonal anti-fibronectin antibody (ab23750, abcam, Cambridge, UK) and 5 µg/ml FnBPA5-Alexa488 respectively scr-FnBPA5-Alexa488 peptide for 1 hour before fixation with a 4% paraformaldehyde solution in PBS. After fixation cells were permeabilized for 10 minutes with PBS containing 0.01% Triton X-100. After a washing step samples were blocked in 4% BSA and 4% donkey serum for 1 hour at room temperature. Samples were then incubated for 1 hour with a donkey anti-rabbit Alexa 546 (Invitrogen) secondary antibody and Phalloidin-633 (Invitrogen, Carlsbad, Calif., USA). Before imaging cell nuclei were stained using DAPI. Fibroblast ECM samples (FIG. 2C) were acquired with an Olympus FV1000 confocal microscope using an oil immersion 1.45 NA 60× objective with a pixel resolution of 1024×1024. Specific binding can then be assessed via colocalization of peptide with Fn using a scrambled peptide derivative as negative control (FIG. 2C).

Example 4: Plasma Stability of FnBPA5

Figure 5:
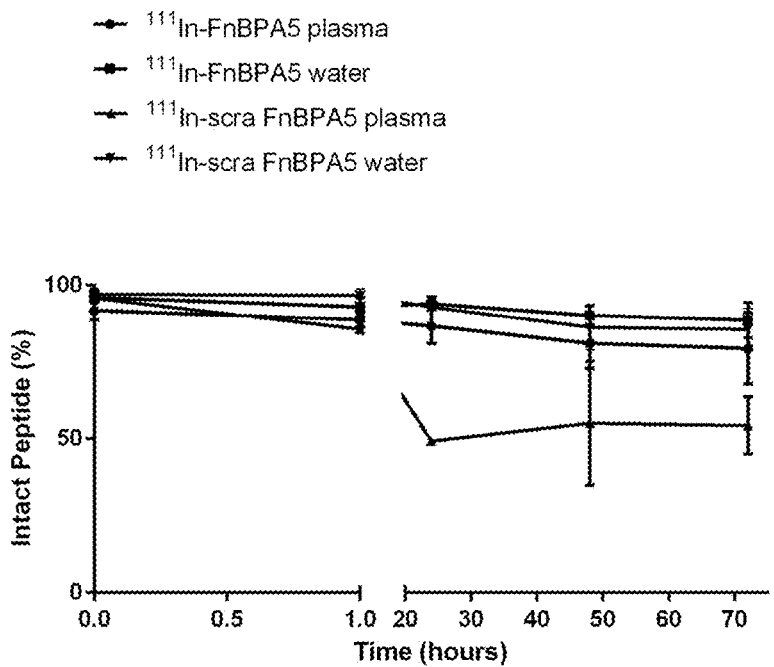
FIG. 5 shows plasma stability of FnBPA5 and its scrambled derivative measured at 37° C. at different time points in blood plasma and water. Both FnBPA5 and scraFnBPA5 show high stability at 1 hour time point.

To assess in vitro plasma stability 12 MBq $^{111}$In-[FnBPA5-NODAGA] and $^{111}$In-[scraFnBPA5-NODAGA] were incubated with 400 µL human blood plasma at 37° C. At different time points (0, 0.25, 0.5, 1, 2, 48 and 72 hours) 40 µL of plasma was taken out and precipitated by the addition of 200 µL EtOH, acetonitrile, 0.1% TFA. After filtrating the sample (MiniPrep, Qiagen, Valencia, Calif., USA) the supernatant was analysed by radio-HPLC (Varian Prostar, USA); column D-Bio Discovery C18, 25×4.6; 5 m with acetonitrile/water gradient starting with 5% acetonitrile up to 95% over 30 minutes with a flow rate of 1 mL/min. $^{111}$In-FnBPA5 peptide was still intact after 72 hours (FIG. 5), thus verifying that the FnBPA5 peptide has sufficient plasma stability to be used for in vivo applications.

Example 5: Fluorescence Polarization Experiments

The binding affinities of Fn to FnBPA5 were determined in three independent measurements by anisotropy titrations in a Cary Eclipse Fluorescence Spectrophotometer (Agilent Technologies) equipped with automated polarizers. FnBPA5 and its scrambled derivative were synthesized with an N-terminal Alexa-488 dye. The anisotropy of 100 nM Alexa-488 labelled peptide was measured in PBS at Fn concentrations ranging from 0 to 1.4 µM. Excitation and emission were at $\lambda_{ex}$ 480 nm and $\lambda_{em}$ 520 nm respectively with both slit 10 nm, 20° C., 5 s signal acquisition and g=1.4. The $K_d$ values were determined by fitting the data to a one-site-binding model using Origin 7 (OriginLab Northampton, Mass., USA).

With higher Fn concentration an increasing amount of peptide is bound to Fn leading to a shift in fluorescence anisotropy. Anisotropy values for each sample was plotted against the corresponding Fn concentration yielding to a binding curve from which a dissociation constant $K_d$ of 75 nM for Alexa 488-FnBPA5 was extrapolated. In contrast, the scrambled control did not show significant binding (FIG. 2D).

Example 6: Radiotracing of $^{111}$In-FnBPA5 Injected into Living Mice

SPECT/CT experiments were performed using a 4-head multiplexing multipinhole camera (NanoSPECT/CTplus, Bioscan Inc., Washington D.C., USA). CT scans were performed with a tube voltage of 45 kV and a tube current of 145 IA. SPECT scans at 24, 72 and 96 hours post injection were obtained with an acquisition time of 20-90 sec. per view resulting in a total scanning time of 20-45 min per mouse.

The distribution of $^{111}$In-radiolabeled FnBPA5 peptide injected into the tail vein of a living mouse was monitored by means of SPECT/CT for a period of 96 hours. Since Fn is upregulated in cancer stroma, PC-3-bearing CD1 nu/nu mice, a subcutaneous model for prostate carcinoma, were injected 33 days from the inoculation of the tumor cells, with 12 MBq $^{111}$In-[FnBPA5-NODAGA] resp. $^{111}$In-[scrambled FnBPA5-NODAGA] (2.4 nmol, 100 µL PBS) into the tail vein. The specific activity of both peptides was 6.2 MBq/nmol and the samples were scanned 96 hours post injection (p.i. and post mortem) with an acquisition time of approximately 20 seconds ($^{111}$In-[FnBPA5-NODAGA]) and 200 seconds ($^{111}$In-[scraFnBPA5-NODAGA]) resulting in a total scanning time of 2.5 h for $^{111}$In-[scraFnBPA5]. SPECT images were reconstructed using HiSPECT software (Scivis GmbH, Goettingen, Germany). The images were reconstituted and processed with InVivoScope® software (Bioscan-Inc., Washington D.C., USA) and zoom in videos were generated using Adobe Flash.

Figure 3:
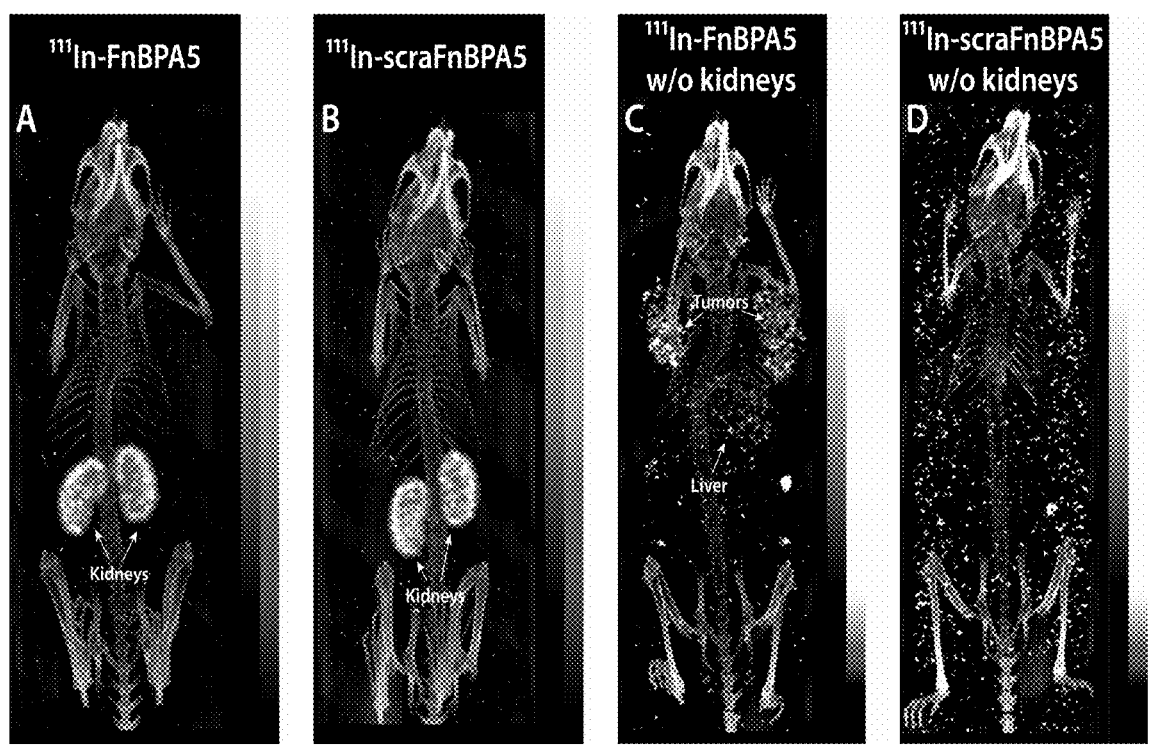
FIG. 3 shows SPECT/CT images of mice bearing PC-3 xenografts 96 hours post injection. Mice were injected with 12 MBq $^{111}$In-FnBPA5 (A and C) respectively $^{111}$In-scrambled FnBPA5 (B and D). Images were acquired post mortem 96 hours post injection. In A and B dominant kidney uptake of both FnBPA5 and scrambled control indicate unspecific clearance via the kidney. The body kidneys were removed in C and D and show uptake in tumors and liver for FnBPA5, whereas scraFnBPA5 does not show any specific uptake in other organs.

As typically observed also for other peptides 111In-FnBPA5 (FIG. 3A) and the negative scrambled control (FIG. 3B) mainly accumulated in the kidneys, indicating an Fn-independent uptake by this organ, presumably due to its blood filtration tasks. To visualize additional binding of the tracer to tissues throughout the body, the kidneys were subsequently removed from the sacrificed mice and the scan was repeated. Mice injected with 111In-FnBPA5 showed activity in different organs, with a predominant uptake in tumor and liver (FIG. 3C). For mice injected with 111In-scraFnBPA5 no uptake into other tissues was visible (FIG. 3D).

Figure 4A:
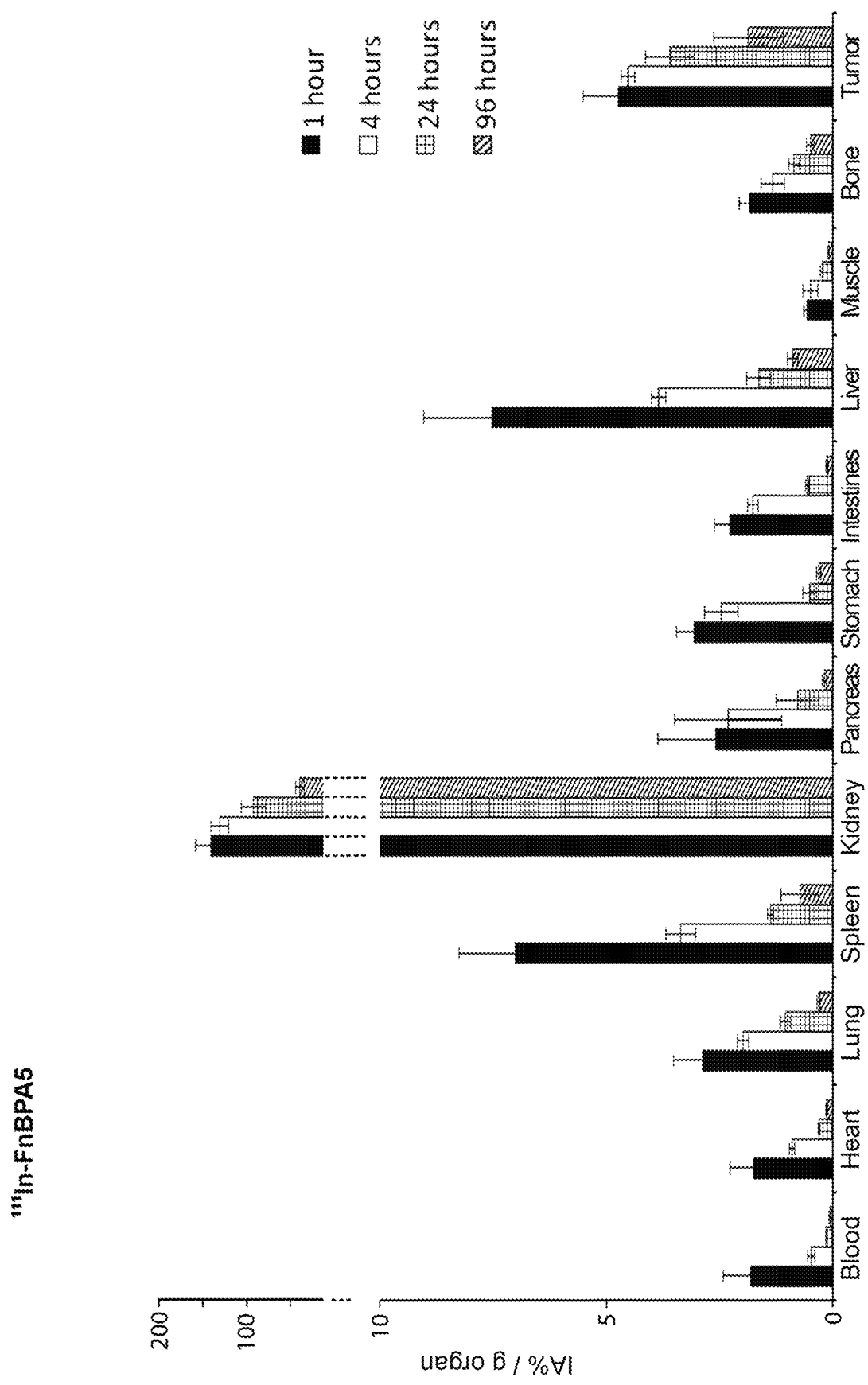
FIG. 4 shows a biodistribution and blocking study of radiolabeled $^{111}$In-FnBPA5 and $^{111}$In-scrambled FnBPA5. (A) Biodistribution of FnBPA5 in PC-3 bearing mice was monitored at different time points in various organs. (B) Biodistribution of scrambled FnBPA5 derivative was monitored the same way. $^{111}$In-FnBPA5 showed a significantly higher uptake than $^{111}$In-scrambled FnBPA5 in all organs except for kidneys and pancreas, confirming the specificity of the accumulation. (C) Blocking studies were performed and uptake was analyzed 4 hour post-injection. Blocking binding sites via pre-injection of unlabeled peptide caused a significant reduction in the uptake of $^{111}$In-FnBPA5 in both liver and tumor (*p<0.05) whereas it did not change uptake in kidneys. Pre-injection showed a higher influence on peptide uptake in the liver than in the tumor, demonstrating the presence of a higher amount of binding sites (fibronectin) in the tumor. (D) Higher retention time of $^{111}$In-FnBPA5 in tumor compared to the other organs is reflected in increasing tumor-to-blood and tumor-to-liver ratios with increasing time.
Figure 4B:
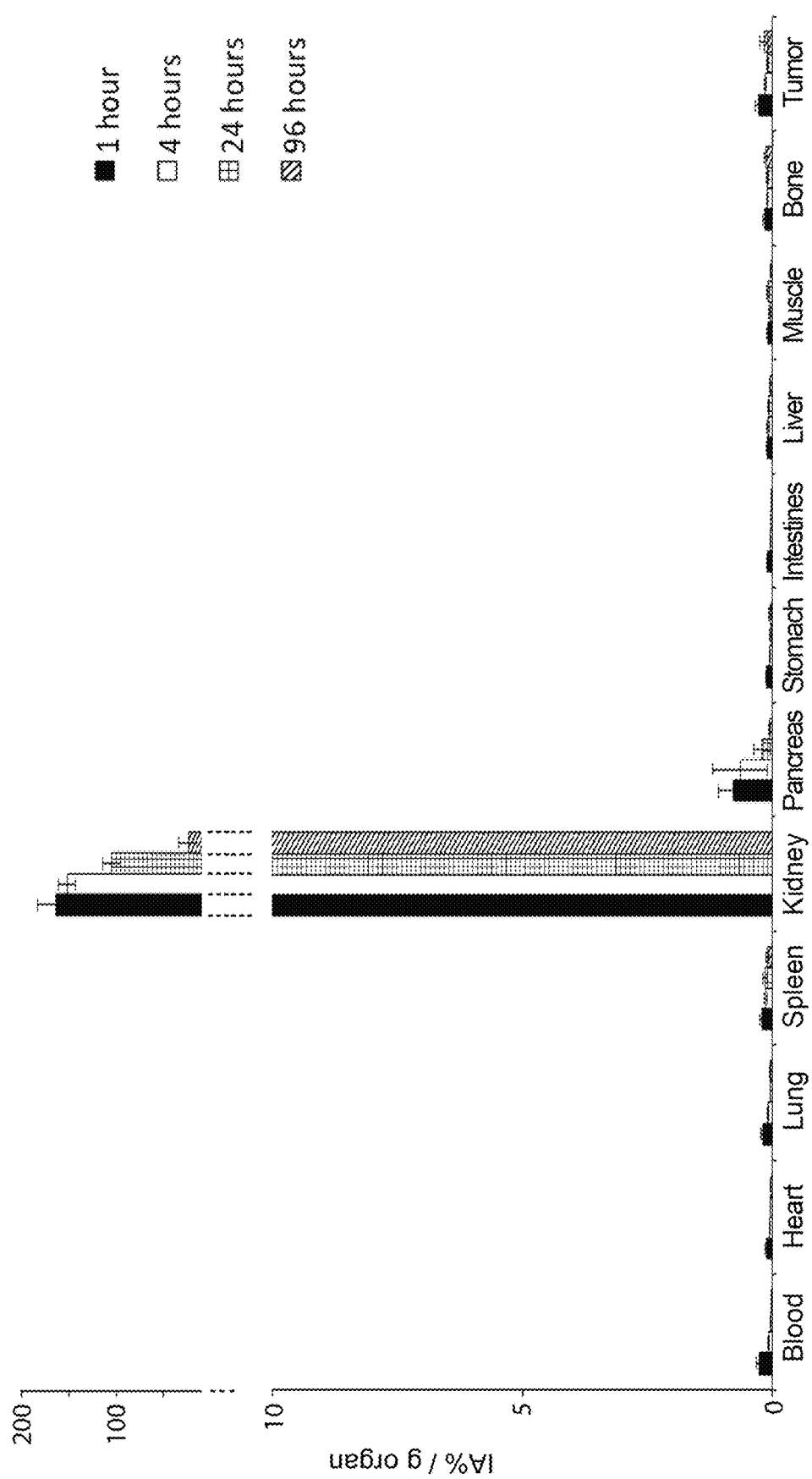
Figures 7, 8:
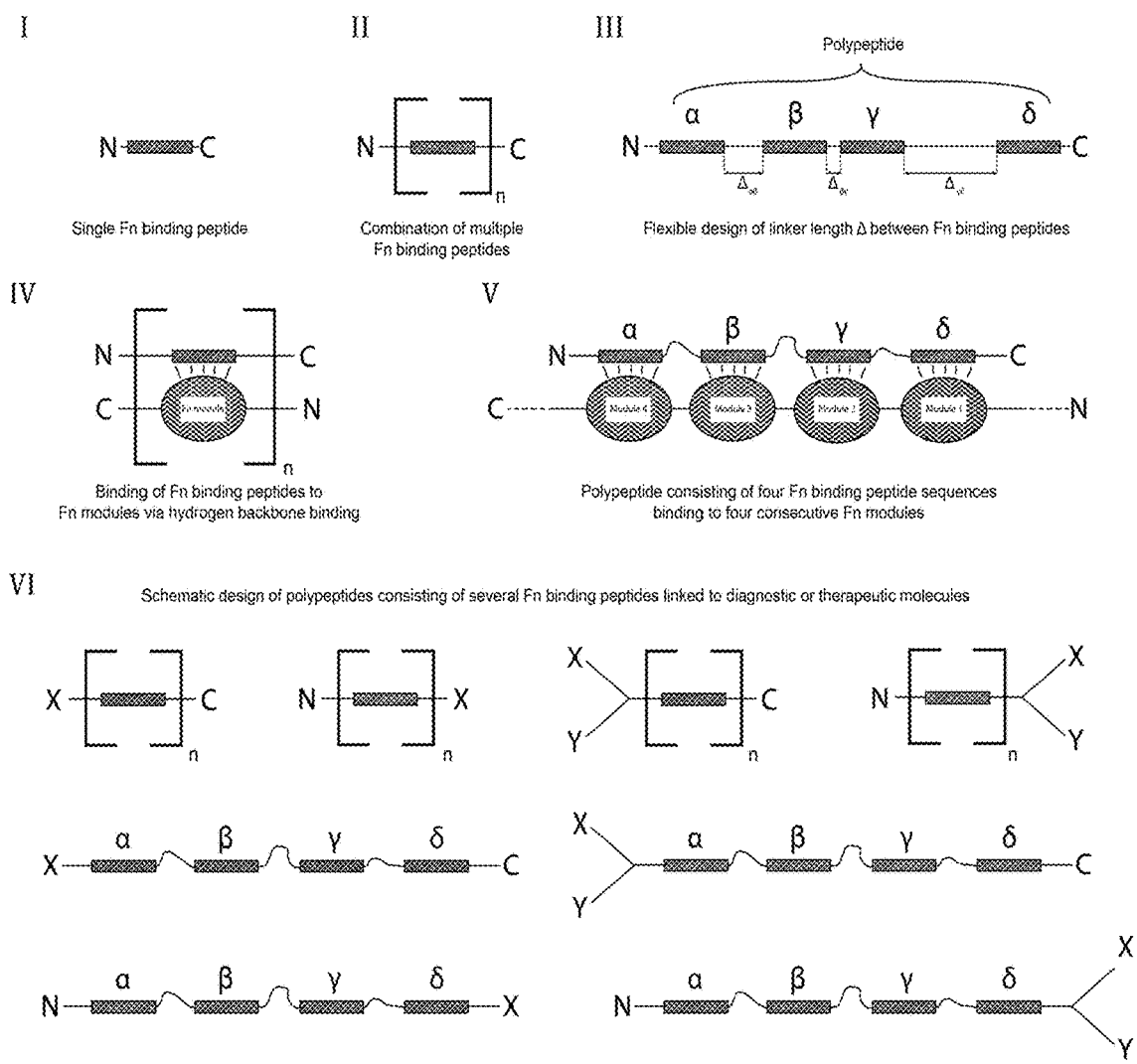
FIG. 7 shows a table containing biodistribution data of $^{111}$In-[FnBPA5-NODAGA] in PC-3 grafted mice.
FIG. 8 shows design modes for fibronectin binding peptides via combination of several Fn binding peptides into polypeptides with variable linker length. (I) Single Fn binding peptide as smallest unit. (II) Combination of several different Fn binding peptides into a Fn binding polypeptide. (III) Amino acid linker length between individual Fn binding peptides within a Fn binding polypeptide is flexible and can be adjusted for individual applications. (IV) Binding of a Fn binding peptide to a Fn module via hydrogen backbone binding. (V) Polypeptide comprised of 4 different Fn binding peptides binding to four consecutive Fn modules via hydrogen backbone binding. (VI) Different functionalization possibilities of Fn binding polypeptides at the N or C-terminus via addition of a functional molecule, such as a chelator-radionuclide complex, a fluorophore, an active component, a drug or prodrug or any kind of particle.

Example 7: Pharmacokinetics of $^{111}$In-FnBPA5 Injected into Living Mice Shows Prolonged Accumulation in Mouse Prostate Tumor Xenografts The tissue-specific peptide pharmacokinetics, particularly in cancer stroma, were assessed in groups of 4 PC-3-bearing mice that were injected with approximately 150 kBq $^{111}$In-FnBPA5 respectively $^{111}$In-scraFnBPA5 (2.4 nmol/100 L PBS) into the tail vein and biodistribution of peptides was analyzed at different time points (1, 4, 24 and 96 hours post injection (p.i. and after sacrification)) by means of percentage of injected activity per gram tissue (% IA/g). An equal accumulation of both peptides was observed in the kidneys (FIGS. 4A, B), confirming the findings from SPECT/CT imaging (see Example 5). In both cases, a maximum at 1 hour p.i. was seen (140.58±18.10% IA/g for $^{111}$In-FnBPA5 and 163.70±18.90% IA/g for $^{111}$In-scra FnBPA5). $^{111}$In-FnBPA5 showed an accumulation in all other examined organs (FIG. 4A), again in contrast to its scrambled derivative. Particularly, in tumor, liver and spleen, the FnBPA5 uptake is significantly higher compared to the scrambled derivative. Tumor uptake was significantly higher for all time points with a maximum at 1 h p.i. (4.74±0.77% IA/g). The retention of $^{111}$In-FnBPA5 in the tumor tissue was longer compared to the other organs (FIG. 4A). In fact, the tumor-to-blood ratio increased from 3.05±1.66 at 1 h p.i. to 34.03±18.36 at 96 h p.i (FIG. 4D and FIG. 7 (ex. supplementary table 1)). Results from the biodistribution are in accordance with the SPECT/CT analysis shown in FIG. 3, and illustrate that the organ uptake of $^{111}$In-FnBPA5 is, apart from the kidneys, specific and related to extracellular matrix protein fibronectin. To further confirm Fn-specific binding of $^{111}$In-FnBPA5, in vivo blocking experiments were performed: an approximately 10-fold excess of unlabeled FnBPA5 (100 µg in 100 L PBS) was pre-injected directly before $^{111}$In-FnBPA5 to block the binding sites (FIG. 4C). The pre-injection of unlabeled FnBPA5 causes a significant reduction (p<0.05) of $^{111}$In-FnBPA5 accumulation in all examined organs with exception of the kidneys and the pancreas. The blocking effect was thereby less pronounced for the tumor tissue (uptake decrease of 35.6%) compared to the liver (58.2%). In contrast, no significant differences were seen for $^{111}$In-scraFnBPA5.

We claim:

1. A composition comprising at least one fibronectin binding polypeptide (FnBP) linked to at least one diagnostic or therapeutic agent, wherein the at least one FnBP is a polypeptide consisting of SEQ ID NO: 295.

2. The composition according to claim 1, wherein the FnBP binds specifically to at least one of fibronectin subunits $FnI_{1-6}$, $FnII_{1-2}$, $FnI_{7-9}$ or $FnIII_{7-15}$.

3. The composition according to claim 1, wherein the diagnostic agent is at least one of a radionuclide, magnetic resonance imaging (MRI) active compound, ultrasound contrast agent, fluorophore, positron emission tomography (PET) marker, single-photon emission computed tomography (SPECT) marker, fluorophore in the far red/near-infrared (IR) spectral region, Gd-based particle based MRI contrast agent, or Fe-oxide particle based MRI contrast agent.

4. The composition according to claim 1, wherein the therapeutic agent is at least one of a cytostatic agent, cytotoxic agent, cytokine, transcription factor inhibitor, proteasome inhibitor, protease inhibitor, apoptosis modulator, cell cycle modulator, angiogenesis inhibitor, hormone, hormone derivative, photodynamic therapy molecule, nanoparticles for thermoablation therapy, microparticles for thermoablation therapy, radionuclide, miRNA, siRNA, immunomodulatory antigen molecule, Doxorubicin, Paclitaxel, Chlorambucil, Topotecan, Vincristine, Interleukin-2, Interleukin-7, Interferon-γ, tumor necrosis factor, Curcumin, Ribavirin, Genistein, Imatinib, Erlotinib, Bryostatin, Flavopiridol, Roscovitine, Endostatin, Celexocib, ADH-1 (exherin), Sunitinib, Flutamide, Fosfestrol, Tamoxifen, Relaxin, $^{64}Cu$, $^{90}Y$, $^{111}In$, $^{131}I$, $^{161}Tb$, $^{169}Er$, $^{177}Lu$, miRNAs specific for CD40, miRNA specific for CD80, miRNA specific for CD86, siRNAs specific for CD40, siRNA specific for CD80, siRNA specific for CD86, insulin-associated antigens, P31, whole gliadin, myelin oligodendrocyte glycoprotein, amino acids 35-55 of myelin oligodendrocyte glycoprotein (SEQ ID NO.: 297), proteolipid protein 1, amino acids 139-151 of proteolipid protein 1 (SEQ ID NO.: 298), amino acids 178-191 of proteolipid protein 1 (SEQ ID NO.: 299), Factor V, amino acids 75-89 of Factor V (SEQ ID NO.: 300), amino acids 1723-1737 of Factor V (SEQ ID NO.: 301), or amino acids 2191-2210 of Factor V (SEQ ID NO.: 302).

5. The composition according to claim 1, wherein the therapeutic agent is at least one of an antifibrotic agent, integrin inhibitor, bone morphogenic protein 7 (BMP-7), relaxin and relaxin-like peptides, lysyl oxidase (LOX) inhibitor beta-aminoproprionitrile (BAPN), or Interleukin-7 (IL-7).

6. The composition according to claim 1, wherein the therapeutic agent is at least one of an immune modulating agent, Interleukin 12, inhibitors that target the EGFR signalling cascade, myelin oligodendrocyte glycoprotein peptide sequence 35-55, a miRNA, an siRNA, PSA-TRICOM, Ipilimumab, anti-CTLA-4 antibody, anti-PD1 antibody, anti-PD-L1 antibody, or HDAC inhibitor.

7. A kit comprising the composition of claim 1.

8. The kit of claim 7, wherein the composition further comprises one or more chemical agents for linking the FnBP to the diagnostic or therapeutic agent.

9. A method for treating a subject suffering from a disease associated with pathological fibronectin accumulation, the method comprising:
(a) providing the composition of claim 1, wherein the FnBP is linked to at least one therapeutic agent, and
(b) administering the composition to the subject in need thereof, wherein the composition is effective for treating the disease associated with pathological fibronectin accumulation, wherein the disease is selected from the group consisting of fibrosis and cancer associated with pathological fibronectin accumulation.

10. A method for diagnosing a disease associated with pathological fibronectin accumulation in a subject, the method comprising:
(a) providing the composition of claim 1, wherein the FnBP is linked to at least one diagnostic agent,
(b) administering the composition to the subject in need thereof, and
(c) identifying pathological fibronectin accumulation by detecting accumulation of the FnBP in said subject.

11. The method according to claim 9, wherein the disease is selected from the group consisting of pulmonary fibrosis, liver fibrosis, kidney fibrosis, breast cancer, and prostate cancer.

12. The method according to claim 10, wherein the disease is selected from the group consisting of fibrosis and cancer associated with pathological fibronectin accumulation.

13. The composition according to claim 5, wherein the relaxin peptide is selected from relaxin-1 and relaxin-2.

14. The composition according to claim 6, wherein the miRNA is selected from a miRNA specific for CD40, miRNA specific for CD80, and miRNA specific for CD86.

15. The composition according to claim 6, wherein the siRNA is selected from an siRNA specific for CD40, siRNA specific for CD80, and siRNA specific for CD86.

16. The method according to claim 12, wherein the disease is selected from the group consisting of pulmonary fibrosis, liver fibrosis, kidney fibrosis, breast cancer and prostate cancer.

* * * * *

SEQUENCE LISTING

<160> NUMBER OF SEQ ID NOS: 302

<210> SEQ ID NO 1
<211> LENGTH: 7
<212> TYPE: PRT
<213> ORGANISM: Streptococcus pyogenes

<400> SEQUENCE: 1

Thr Glu Val Tyr Gly Asn Gln
1               5

<210> SEQ ID NO 2
<211> LENGTH: 7
<212> TYPE: PRT
<213> ORGANISM: Streptococcus pyogenes

<400> SEQUENCE: 2

Val Asp Ile Asp Lys Lys Leu
1               5

```
<210> SEQ ID NO 3
<211> LENGTH: 7
<212> TYPE: PRT
<213> ORGANISM: Streptococcus pyogenes

<400> SEQUENCE: 3

Pro Asn Glu Thr Gly Phe Ser
1               5

<210> SEQ ID NO 4
<211> LENGTH: 7
<212> TYPE: PRT
<213> ORGANISM: Streptococcus pyogenes

<400> SEQUENCE: 4

Met Val Glu Thr Glu Asp Thr
1               5

<210> SEQ ID NO 5
<211> LENGTH: 7
<212> TYPE: PRT
<213> ORGANISM: Streptococcus pyogenes

<400> SEQUENCE: 5

Glu Val Leu Met Gly Gly Gln
1               5

<210> SEQ ID NO 6
<211> LENGTH: 7
<212> TYPE: PRT
<213> ORGANISM: Streptococcus pyogenes

<400> SEQUENCE: 6

Val Glu Phe Thr Lys Asp Thr
1               5

<210> SEQ ID NO 7
<211> LENGTH: 7
<212> TYPE: PRT
<213> ORGANISM: Streptococcus pyogenes

<400> SEQUENCE: 7

Thr Gly Met Ser Gly Gln Thr
1               5

<210> SEQ ID NO 8
<211> LENGTH: 7
<212> TYPE: PRT
<213> ORGANISM: Streptococcus pyogenes

<400> SEQUENCE: 8

Gln Val Glu Thr Glu Asp Thr
1               5

<210> SEQ ID NO 9
<211> LENGTH: 7
<212> TYPE: PRT
<213> ORGANISM: Streptococcus pyogenes

<400> SEQUENCE: 9

Gly Val Leu Met Gly Gly Gln
1               5

<210> SEQ ID NO 10
```

```
<211> LENGTH: 7
<212> TYPE: PRT
<213> ORGANISM: Streptococcus pyogenes

<400> SEQUENCE: 10

Thr Gly Met Ser Gly Phe Ser
1               5

<210> SEQ ID NO 11
<211> LENGTH: 7
<212> TYPE: PRT
<213> ORGANISM: Streptococcus pyogenes

<400> SEQUENCE: 11

Val Thr Ile Ile Glu Asp Thr
1               5

<210> SEQ ID NO 12
<211> LENGTH: 7
<212> TYPE: PRT
<213> ORGANISM: Streptococcus pyogenes

<400> SEQUENCE: 12

Leu Val Phe His Phe Asp Asn
1               5

<210> SEQ ID NO 13
<211> LENGTH: 7
<212> TYPE: PRT
<213> ORGANISM: Streptococcus pyogenes

<400> SEQUENCE: 13

Val Ser Thr Gln Glu Asn Lys
1               5

<210> SEQ ID NO 14
<211> LENGTH: 7
<212> TYPE: PRT
<213> ORGANISM: Streptococcus pyogenes

<400> SEQUENCE: 14

Val Asp Ile Thr Glu Asp Thr
1               5

<210> SEQ ID NO 15
<211> LENGTH: 7
<212> TYPE: PRT
<213> ORGANISM: Streptococcus pyogenes

<400> SEQUENCE: 15

Pro Gly Met Ser Gly Ser Asn
1               5

<210> SEQ ID NO 16
<211> LENGTH: 7
<212> TYPE: PRT
<213> ORGANISM: Streptococcus pyogenes

<400> SEQUENCE: 16

Thr Val Val Glu Glu Asp Thr
1               5

<210> SEQ ID NO 17
<211> LENGTH: 7
<212> TYPE: PRT
```

<213> ORGANISM: Streptococcus pyogenes

<400> SEQUENCE: 17

Asp Val Leu Val Gly Gly Gln
1               5

<210> SEQ ID NO 18
<211> LENGTH: 7
<212> TYPE: PRT
<213> ORGANISM: Streptococcus pyogenes

<400> SEQUENCE: 18

Ile Asp Ile Thr Glu Asp Thr
1               5

<210> SEQ ID NO 19
<211> LENGTH: 7
<212> TYPE: PRT
<213> ORGANISM: Streptococcus pyogenes

<400> SEQUENCE: 19

Asp Ile Leu Val Gly Gly Gln
1               5

<210> SEQ ID NO 20
<211> LENGTH: 7
<212> TYPE: PRT
<213> ORGANISM: Streptococcus pyogenes

<400> SEQUENCE: 20

Thr Val Ile Glu Glu Asp Thr
1               5

<210> SEQ ID NO 21
<211> LENGTH: 7
<212> TYPE: PRT
<213> ORGANISM: Streptococcus pyogenes

<400> SEQUENCE: 21

Arg Phe Phe His Phe Asp Asn
1               5

<210> SEQ ID NO 22
<211> LENGTH: 7
<212> TYPE: PRT
<213> ORGANISM: Streptococcus pyogenes

<400> SEQUENCE: 22

Arg Glu Val Ile Thr Gln Gln
1               5

<210> SEQ ID NO 23
<211> LENGTH: 7
<212> TYPE: PRT
<213> ORGANISM: Streptococcus pyogenes

<400> SEQUENCE: 23

Asn Leu Glu Ile Glu Glu Thr
1               5

<210> SEQ ID NO 24
<211> LENGTH: 7
<212> TYPE: PRT
<213> ORGANISM: Streptococcus pyogenes

```
<400> SEQUENCE: 24

Pro Leu Glu Ser Gly Ala Ser
1               5

<210> SEQ ID NO 25
<211> LENGTH: 7
<212> TYPE: PRT
<213> ORGANISM: Streptococcus pyogenes

<400> SEQUENCE: 25

Thr Thr Thr Val Glu Asp Ser
1               5

<210> SEQ ID NO 26
<211> LENGTH: 7
<212> TYPE: PRT
<213> ORGANISM: Streptococcus pyogenes

<400> SEQUENCE: 26

Tyr Lys Pro Thr Lys Gly Ser
1               5

<210> SEQ ID NO 27
<211> LENGTH: 7
<212> TYPE: PRT
<213> ORGANISM: Streptococcus pyogenes

<400> SEQUENCE: 27

Val Ile Asp Ile Glu Glu Lys
1               5

<210> SEQ ID NO 28
<211> LENGTH: 7
<212> TYPE: PRT
<213> ORGANISM: Streptococcus pyogenes

<400> SEQUENCE: 28

Pro Asp Glu Gln Gly His Ser
1               5

<210> SEQ ID NO 29
<211> LENGTH: 7
<212> TYPE: PRT
<213> ORGANISM: Streptococcus pyogenes

<400> SEQUENCE: 29

Thr Thr Glu Ile Glu Asp Ser
1               5

<210> SEQ ID NO 30
<211> LENGTH: 7
<212> TYPE: PRT
<213> ORGANISM: Streptococcus pyogenes

<400> SEQUENCE: 30

Asp Val Ile Ile Gly Gly Gln
1               5

<210> SEQ ID NO 31
<211> LENGTH: 7
<212> TYPE: PRT
<213> ORGANISM: Streptococcus pyogenes

<400> SEQUENCE: 31
```

Val Asp Thr Thr Glu Asp Thr
1               5

<210> SEQ ID NO 32
<211> LENGTH: 7
<212> TYPE: PRT
<213> ORGANISM: Streptococcus pyogenes

<400> SEQUENCE: 32

Ser Gly Met Thr Gly His Ser
1               5

<210> SEQ ID NO 33
<211> LENGTH: 7
<212> TYPE: PRT
<213> ORGANISM: Streptococcus pyogenes

<400> SEQUENCE: 33

Val Glu Thr Thr Glu Asp Thr
1               5

<210> SEQ ID NO 34
<211> LENGTH: 7
<212> TYPE: PRT
<213> ORGANISM: Streptococcus pyogenes

<400> SEQUENCE: 34

Thr Gly Met His Gly Asp Ser
1               5

<210> SEQ ID NO 35
<211> LENGTH: 7
<212> TYPE: PRT
<213> ORGANISM: Streptococcus pyogenes

<400> SEQUENCE: 35

Lys Thr Glu Val Glu Asp Thr
1               5

<210> SEQ ID NO 36
<211> LENGTH: 7
<212> TYPE: PRT
<213> ORGANISM: Streptococcus pyogenes

<400> SEQUENCE: 36

Gln Leu Phe His Phe Asp Asn
1               5

<210> SEQ ID NO 37
<211> LENGTH: 7
<212> TYPE: PRT
<213> ORGANISM: Streptococcus equi

<400> SEQUENCE: 37

Pro Gly Gln Thr Gly Gly Gln
1               5

<210> SEQ ID NO 38
<211> LENGTH: 7
<212> TYPE: PRT
<213> ORGANISM: Streptococcus equi

<400> SEQUENCE: 38

Ile Glu Thr Thr Glu Asp Thr
1               5

<210> SEQ ID NO 39
<211> LENGTH: 7
<212> TYPE: PRT
<213> ORGANISM: Streptococcus equi

<400> SEQUENCE: 39

Lys Gly Met Ser Gly Gln Ser
1               5

<210> SEQ ID NO 40
<211> LENGTH: 7
<212> TYPE: PRT
<213> ORGANISM: Streptococcus equi

<400> SEQUENCE: 40

Thr Ile Glu Ser Glu Asn Thr
1               5

<210> SEQ ID NO 41
<211> LENGTH: 7
<212> TYPE: PRT
<213> ORGANISM: Streptococcus equi

<400> SEQUENCE: 41

Glu Val Met Ile Gly Gly Gln
1               5

<210> SEQ ID NO 42
<211> LENGTH: 7
<212> TYPE: PRT
<213> ORGANISM: Streptococcus equi

<400> SEQUENCE: 42

Thr Ile Glu Ser Glu Asp Thr
1               5

<210> SEQ ID NO 43
<211> LENGTH: 7
<212> TYPE: PRT
<213> ORGANISM: Streptococcus equi

<400> SEQUENCE: 43

Ile Asp Phe Ser Glu Asn Thr
1               5

<210> SEQ ID NO 44
<211> LENGTH: 7
<212> TYPE: PRT
<213> ORGANISM: Streptococcus equi

<400> SEQUENCE: 44

Ser Gly Met Ser Gly Gln Ser
1               5

<210> SEQ ID NO 45
<211> LENGTH: 7
<212> TYPE: PRT
<213> ORGANISM: Streptococcus equi

<400> SEQUENCE: 45

Thr Thr Val Ile Glu Asp Thr
1               5

```
<210> SEQ ID NO 46
<211> LENGTH: 7
<212> TYPE: PRT
<213> ORGANISM: Streptococcus equi

<400> SEQUENCE: 46

Glu Ile Ile Ile Gly Gly Gln
1               5

<210> SEQ ID NO 47
<211> LENGTH: 7
<212> TYPE: PRT
<213> ORGANISM: Streptococcus equi

<400> SEQUENCE: 47

Ile Asp Phe Ser Glu Asp Thr
1               5

<210> SEQ ID NO 48
<211> LENGTH: 7
<212> TYPE: PRT
<213> ORGANISM: Streptococcus equi

<400> SEQUENCE: 48

Pro Gly Met Ser Gly Gln Ser
1               5

<210> SEQ ID NO 49
<211> LENGTH: 7
<212> TYPE: PRT
<213> ORGANISM: Streptococcus equi

<400> SEQUENCE: 49

Thr Thr Ile Val Glu Asp Thr
1               5

<210> SEQ ID NO 50
<211> LENGTH: 7
<212> TYPE: PRT
<213> ORGANISM: Streptococcus dysgalactiae

<400> SEQUENCE: 50

Glu Asn Asn Leu Gly Gly Gln
1               5

<210> SEQ ID NO 51
<211> LENGTH: 7
<212> TYPE: PRT
<213> ORGANISM: Streptococcus dysgalactiae

<400> SEQUENCE: 51

Ile Thr Ile Thr Glu Asp Ser
1               5

<210> SEQ ID NO 52
<211> LENGTH: 7
<212> TYPE: PRT
<213> ORGANISM: Streptococcus dysgalactiae

<400> SEQUENCE: 52

Ser Gly Met Ser Gly Gln Asn
1               5

<210> SEQ ID NO 53
<211> LENGTH: 7
```

```
<212> TYPE: PRT
<213> ORGANISM: Streptococcus dysgalactiae

<400> SEQUENCE: 53

Glu Thr Val Val Glu Asp Thr
1               5

<210> SEQ ID NO 54
<211> LENGTH: 7
<212> TYPE: PRT
<213> ORGANISM: Streptococcus dysgalactiae

<400> SEQUENCE: 54

Asp Ile Val Leu Gly Gly Pro
1               5

<210> SEQ ID NO 55
<211> LENGTH: 7
<212> TYPE: PRT
<213> ORGANISM: Streptococcus dysgalactiae

<400> SEQUENCE: 55

Ile Asp Phe Thr Glu Asp Ser
1               5

<210> SEQ ID NO 56
<211> LENGTH: 7
<212> TYPE: PRT
<213> ORGANISM: Streptococcus dysgalactiae

<400> SEQUENCE: 56

Pro Gly Met Ser Gly Asn Asn
1               5

<210> SEQ ID NO 57
<211> LENGTH: 7
<212> TYPE: PRT
<213> ORGANISM: Streptococcus dysgalactiae

<400> SEQUENCE: 57

His Thr Ile Thr Glu Asp Ser
1               5

<210> SEQ ID NO 58
<211> LENGTH: 7
<212> TYPE: PRT
<213> ORGANISM: Streptococcus dysgalactiae

<400> SEQUENCE: 58

Glu Val Ile Ile Gly Gly Gln
1               5

<210> SEQ ID NO 59
<211> LENGTH: 7
<212> TYPE: PRT
<213> ORGANISM: Streptococcus dysgalactiae

<400> SEQUENCE: 59

Ile Asp Phe Thr Glu Asp Thr
1               5

<210> SEQ ID NO 60
<211> LENGTH: 7
<212> TYPE: PRT
<213> ORGANISM: Streptococcus dysgalactiae
```

<400> SEQUENCE: 60

Ser Gly Met Ser Gly Asp Asn
1               5

<210> SEQ ID NO 61
<211> LENGTH: 7
<212> TYPE: PRT
<213> ORGANISM: Streptococcus dysgalactiae

<400> SEQUENCE: 61

Thr Val Leu Glu Glu Asp Ser
1               5

<210> SEQ ID NO 62
<211> LENGTH: 7
<212> TYPE: PRT
<213> ORGANISM: Streptococcus dysgalactiae

<400> SEQUENCE: 62

Thr Gly Met Ser Gly Ala Gly
1               5

<210> SEQ ID NO 63
<211> LENGTH: 7
<212> TYPE: PRT
<213> ORGANISM: Streptococcus dysgalactiae

<400> SEQUENCE: 63

Pro Thr Ile Thr Glu Glu Thr
1               5

<210> SEQ ID NO 64
<211> LENGTH: 7
<212> TYPE: PRT
<213> ORGANISM: Streptococcus dysgalactiae

<400> SEQUENCE: 64

Glu Ile Ile Met Gly Gly Gln
1               5

<210> SEQ ID NO 65
<211> LENGTH: 7
<212> TYPE: PRT
<213> ORGANISM: Streptococcus dysgalactiae

<400> SEQUENCE: 65

Ile Asp Met Val Glu Asp Thr
1               5

<210> SEQ ID NO 66
<211> LENGTH: 7
<212> TYPE: PRT
<213> ORGANISM: Streptococcus dysgalactiae

<400> SEQUENCE: 66

Pro Gly Met Ser Gly Ser Asn
1               5

<210> SEQ ID NO 67
<211> LENGTH: 7
<212> TYPE: PRT
<213> ORGANISM: Streptococcus dysgalactiae

<400> SEQUENCE: 67

```
<210> SEQ ID NO 68
<211> LENGTH: 7
<212> TYPE: PRT
<213> ORGANISM: Streptococcus dysgalactiae

<400> SEQUENCE: 68

Thr Val Val Glu Glu Asp Thr
1               5

<210> SEQ ID NO 68
<211> LENGTH: 7
<212> TYPE: PRT
<213> ORGANISM: Streptococcus dysgalactiae

<400> SEQUENCE: 68

Leu Gln Phe His Phe Asp Asn
1               5

<210> SEQ ID NO 69
<211> LENGTH: 7
<212> TYPE: PRT
<213> ORGANISM: Streptococcus dysgalactiae

<400> SEQUENCE: 69

Glu Val Ile Ile Gln Gln Gly
1               5

<210> SEQ ID NO 70
<211> LENGTH: 7
<212> TYPE: PRT
<213> ORGANISM: Streptococcus dysgalactiae

<400> SEQUENCE: 70

Ile Leu Gly Leu Glu Glu Thr
1               5

<210> SEQ ID NO 71
<211> LENGTH: 7
<212> TYPE: PRT
<213> ORGANISM: Streptococcus dysgalactiae

<400> SEQUENCE: 71

Pro Thr Glu Glu His Gln Ser
1               5

<210> SEQ ID NO 72
<211> LENGTH: 7
<212> TYPE: PRT
<213> ORGANISM: Streptococcus dysgalactiae

<400> SEQUENCE: 72

Thr Thr Thr Ile Glu Asp Thr
1               5

<210> SEQ ID NO 73
<211> LENGTH: 7
<212> TYPE: PRT
<213> ORGANISM: Streptococcus dysgalactiae

<400> SEQUENCE: 73

Asp Lys Pro Ile Thr Glu Ala
1               5

<210> SEQ ID NO 74
<211> LENGTH: 7
<212> TYPE: PRT
<213> ORGANISM: Streptococcus dysgalactiae

<400> SEQUENCE: 74

Ser Ile Asp Phe Glu Glu Thr
```

<210> SEQ ID NO 75
<211> LENGTH: 7
<212> TYPE: PRT
<213> ORGANISM: Streptococcus dysgalactiae

<400> SEQUENCE: 75

Pro Thr Glu Gln Gly Gln Ser
1               5

<210> SEQ ID NO 76
<211> LENGTH: 7
<212> TYPE: PRT
<213> ORGANISM: Streptococcus dysgalactiae

<400> SEQUENCE: 76

Thr Thr Glu Val Glu Asp Thr
1               5

<210> SEQ ID NO 77
<211> LENGTH: 7
<212> TYPE: PRT
<213> ORGANISM: Streptococcus dysgalactiae

<400> SEQUENCE: 77

Ile Val Asp Ile Glu Glu Asn
1               5

<210> SEQ ID NO 78
<211> LENGTH: 7
<212> TYPE: PRT
<213> ORGANISM: Streptococcus dysgalactiae

<400> SEQUENCE: 78

Val Val Asp Ile Glu Glu Ser
1               5

<210> SEQ ID NO 79
<211> LENGTH: 7
<212> TYPE: PRT
<213> ORGANISM: Streptococcus dysgalactiae

<400> SEQUENCE: 79

Thr Thr Glu Val Glu Asp Ser
1               5

<210> SEQ ID NO 80
<211> LENGTH: 7
<212> TYPE: PRT
<213> ORGANISM: Streptococcus dysgalactiae

<400> SEQUENCE: 80

Leu Ser Ile His Phe Asp Asn
1               5

<210> SEQ ID NO 81
<211> LENGTH: 7
<212> TYPE: PRT
<213> ORGANISM: Staphylococcus aureus

<400> SEQUENCE: 81

Gly Pro Ile Ile Gln Asn Asn
1               5

```
<210> SEQ ID NO 82
<211> LENGTH: 7
<212> TYPE: PRT
<213> ORGANISM: Staphylococcus aureus

<400> SEQUENCE: 82

Phe Glu Tyr Lys Glu Asp Thr
1               5

<210> SEQ ID NO 83
<211> LENGTH: 7
<212> TYPE: PRT
<213> ORGANISM: Staphylococcus aureus

<400> SEQUENCE: 83

Glu Thr Leu Thr Gly Gln Tyr
1               5

<210> SEQ ID NO 84
<211> LENGTH: 7
<212> TYPE: PRT
<213> ORGANISM: Staphylococcus aureus

<400> SEQUENCE: 84

Thr Thr Val Glu Glu Glu Tyr
1               5

<210> SEQ ID NO 85
<211> LENGTH: 6
<212> TYPE: PRT
<213> ORGANISM: Staphylococcus aureus

<400> SEQUENCE: 85

Ile Asp Phe Glu Glu Ser
1               5

<210> SEQ ID NO 86
<211> LENGTH: 7
<212> TYPE: PRT
<213> ORGANISM: Staphylococcus aureus

<400> SEQUENCE: 86

Glu Asn Ser Lys His His Ala
1               5

<210> SEQ ID NO 87
<211> LENGTH: 7
<212> TYPE: PRT
<213> ORGANISM: Staphylococcus aureus

<400> SEQUENCE: 87

Val Glu Tyr Glu Glu Asp Thr
1               5

<210> SEQ ID NO 88
<211> LENGTH: 7
<212> TYPE: PRT
<213> ORGANISM: Staphylococcus aureus

<400> SEQUENCE: 88

Gln Val Thr Thr Glu Ser Asn
1               5

<210> SEQ ID NO 89
```

```
<211> LENGTH: 7
<212> TYPE: PRT
<213> ORGANISM: Staphylococcus aureus

<400> SEQUENCE: 89

Val Glu Phe Asp Glu Glu Ser
1               5

<210> SEQ ID NO 90
<211> LENGTH: 7
<212> TYPE: PRT
<213> ORGANISM: Staphylococcus aureus

<400> SEQUENCE: 90

Gly Ile Val Thr Gly Ala Val
1               5

<210> SEQ ID NO 91
<211> LENGTH: 7
<212> TYPE: PRT
<213> ORGANISM: Staphylococcus aureus

<400> SEQUENCE: 91

His Thr Thr Val Glu Asp Thr
1               5

<210> SEQ ID NO 92
<211> LENGTH: 7
<212> TYPE: PRT
<213> ORGANISM: Staphylococcus aureus

<400> SEQUENCE: 92

Lys Tyr Glu Gln Gly Gly Asn
1               5

<210> SEQ ID NO 93
<211> LENGTH: 7
<212> TYPE: PRT
<213> ORGANISM: Staphylococcus aureus

<400> SEQUENCE: 93

Val Asp Ile Asp Phe Asp Ser
1               5

<210> SEQ ID NO 94
<211> LENGTH: 7
<212> TYPE: PRT
<213> ORGANISM: Staphylococcus aureus

<400> SEQUENCE: 94

Pro Gln Ile His Gly Gln Asn
1               5

<210> SEQ ID NO 95
<211> LENGTH: 7
<212> TYPE: PRT
<213> ORGANISM: Staphylococcus aureus

<400> SEQUENCE: 95

Gln Ser Phe Glu Glu Asp Thr
1               5

<210> SEQ ID NO 96
<211> LENGTH: 7
<212> TYPE: PRT
```

```
<213> ORGANISM: Staphylococcus aureus

<400> SEQUENCE: 96

Lys Tyr Glu His Gly Gly Asn
1               5

<210> SEQ ID NO 97
<211> LENGTH: 7
<212> TYPE: PRT
<213> ORGANISM: Staphylococcus aureus

<400> SEQUENCE: 97

Ile Asp Ile Asp Phe Asp Ser
1               5

<210> SEQ ID NO 98
<211> LENGTH: 7
<212> TYPE: PRT
<213> ORGANISM: Staphylococcus aureus

<400> SEQUENCE: 98

Pro His Ile His Gly Phe Asn
1               5

<210> SEQ ID NO 99
<211> LENGTH: 7
<212> TYPE: PRT
<213> ORGANISM: Staphylococcus aureus

<400> SEQUENCE: 99

Glu Ile Ile Glu Glu Asp Thr
1               5

<210> SEQ ID NO 100
<211> LENGTH: 7
<212> TYPE: PRT
<213> ORGANISM: Staphylococcus aureus

<400> SEQUENCE: 100

Ser Tyr Gln Phe Gly Gly His
1               5

<210> SEQ ID NO 101
<211> LENGTH: 7
<212> TYPE: PRT
<213> ORGANISM: Staphylococcus aureus

<400> SEQUENCE: 101

Val Asp Phe Glu Glu Asp Thr
1               5

<210> SEQ ID NO 102
<211> LENGTH: 7
<212> TYPE: PRT
<213> ORGANISM: Staphylococcus aureus

<400> SEQUENCE: 102

Pro Lys Val Ser Gly Gln Asn
1               5

<210> SEQ ID NO 103
<211> LENGTH: 7
<212> TYPE: PRT
<213> ORGANISM: Staphylococcus aureus
```

```
<400> SEQUENCE: 103

Gln Thr Ile Glu Glu Asp Thr
1               5

<210> SEQ ID NO 104
<211> LENGTH: 6
<212> TYPE: PRT
<213> ORGANISM: Borrelia burgdorferi

<400> SEQUENCE: 104

Glu Pro Ile Glu Ser Asn
1               5

<210> SEQ ID NO 105
<211> LENGTH: 7
<212> TYPE: PRT
<213> ORGANISM: Borrelia burgdorferi

<400> SEQUENCE: 105

Ile Asp Leu Thr Ile Asp Ser
1               5

<210> SEQ ID NO 106
<211> LENGTH: 7
<212> TYPE: PRT
<213> ORGANISM: Borrelia burgdorferi

<400> SEQUENCE: 106

Gln Gly Ile Ala Gly Ser Asn
1               5

<210> SEQ ID NO 107
<211> LENGTH: 7
<212> TYPE: PRT
<213> ORGANISM: Borrelia burgdorferi

<400> SEQUENCE: 107

Glu Ile Glu Glu Glu Asp Tyr
1               5

<210> SEQ ID NO 108
<211> LENGTH: 11
<212> TYPE: PRT
<213> ORGANISM: Mycobacterium tuberculosis

<400> SEQUENCE: 108

Phe Glu Trp Tyr Asp Gln Ser Gly Leu Ser Val
1               5                   10

<210> SEQ ID NO 109
<211> LENGTH: 11
<212> TYPE: PRT
<213> ORGANISM: Mycobacterium tuberculosis

<400> SEQUENCE: 109

Phe Glu Trp Tyr Tyr Gln Ser Gly Leu Ser Ile
1               5                   10

<210> SEQ ID NO 110
<211> LENGTH: 11
<212> TYPE: PRT
<213> ORGANISM: Mycobacterium tuberculosis

<400> SEQUENCE: 110
```

```
Phe Glu Glu Tyr Tyr Gln Ser Gly Leu Ser Val
1               5                   10
```

<210> SEQ ID NO 111
<211> LENGTH: 110
<212> TYPE: PRT
<213> ORGANISM: Streptococcus equi subsp. equi

<400> SEQUENCE: 111

```
Leu Pro Glu Lys Gly Leu Asn Gly Glu Asn Gln Lys Glu Pro Glu Gln
1               5                   10                  15

Gly Glu Arg Gly Glu Ala Gly Pro Pro Leu Ser Gly Leu Ser Gly Asn
                20                  25                  30

Asn Gln Gly Arg Pro Ser Leu Pro Gly Leu Asn Gly Glu Asn Gln Lys
            35                  40                  45

Glu Pro Glu Gln Gly Glu Arg Gly Glu Ala Gly Pro Pro Ser Thr Pro
        50                  55                  60

Asn Leu Glu Gly Asn Asn Arg Lys Asn Pro Leu Lys Gly Leu Asp Gly
65                  70                  75                  80

Glu Asn Lys Pro Lys Glu Asp Leu Asp Gly Lys Gly Leu Ser Gly Glu
                85                  90                  95

Asn Asp Glu Ser Pro Lys Leu Lys Asp Glu His Pro Tyr Asn
            100                 105                 110
```

<210> SEQ ID NO 112
<211> LENGTH: 110
<212> TYPE: PRT
<213> ORGANISM: Streptococcus equi subsp. zooepidemicus

<400> SEQUENCE: 112

```
Leu Pro Glu Lys Gly Leu Asn Gly Glu Asn Gln Lys Glu Pro Glu Gln
1               5                   10                  15

Gly Glu Arg Gly Glu Ala Gly Pro Pro Ser Thr Pro Asn Leu Glu Gly
                20                  25                  30

Asn Asn Arg Lys Asn Pro Leu Lys Gly Leu Asp Gly Glu Asn Lys Pro
            35                  40                  45

Lys Glu Asp Leu Asp Gly Lys Gly Leu Ser Gly Glu Asn Asp Glu Ser
        50                  55                  60

Pro Lys Leu Lys Asp Glu His Pro Tyr Asn His Gly Arg Arg Asp Gly
65                  70                  75                  80

Tyr Arg Val Gly Tyr Glu Asp Gly Tyr Gly Lys His Lys Gly
                85                  90                  95

Asp Tyr Pro Lys Arg Phe Asp Glu Ser Ser Pro Lys Glu Tyr
            100                 105                 110
```

<210> SEQ ID NO 113
<211> LENGTH: 20
<212> TYPE: PRT
<213> ORGANISM: Homo sapiens

<400> SEQUENCE: 113

```
Arg Phe Lys Gln Asp Gly Gly Trp Ser His Trp Ser Pro Trp Ser Ser
1               5                   10                  15

Cys Ser Val Thr
            20
```

<210> SEQ ID NO 114
<211> LENGTH: 40
<212> TYPE: PRT

<213> ORGANISM: Homo sapiens

<400> SEQUENCE: 114

Gly Pro Ala Gly Ala Pro Gly Thr Pro Gly Pro Gln Gly Ile Ala Gly
1               5                   10                  15

Gln Arg Gly Val Val Gly Leu Pro Gly Gln Arg Gly Glu Arg Gly Phe
            20                  25                  30

Pro Gly Leu Pro Gly Pro Ser Gly
        35                  40

<210> SEQ ID NO 115
<211> LENGTH: 12
<212> TYPE: PRT
<213> ORGANISM: Homo sapiens

<400> SEQUENCE: 115

Thr Leu Gln Pro Val Tyr Glu Tyr Met Val Gly Val
1               5                   10

<210> SEQ ID NO 116
<211> LENGTH: 15
<212> TYPE: PRT
<213> ORGANISM: Homo sapiens

<400> SEQUENCE: 116

Thr Gly Leu Pro Val Gly Val Gly Tyr Val Val Thr Val Leu Thr
1               5                   10                  15

<210> SEQ ID NO 117
<211> LENGTH: 36
<212> TYPE: PRT
<213> ORGANISM: Streptococcus pyogenes

<400> SEQUENCE: 117

Thr Glu Val Tyr Gly Asn Gln Gln Asn Pro Val Asp Ile Asp Lys Lys
1               5                   10                  15

Leu Pro Asn Glu Thr Gly Phe Ser Gly Asn Met Val Glu Thr Glu Asp
            20                  25                  30

Thr Lys Glu Pro
        35

<210> SEQ ID NO 118
<211> LENGTH: 37
<212> TYPE: PRT
<213> ORGANISM: Streptococcus pyogenes

<400> SEQUENCE: 118

Glu Val Leu Met Gly Gly Gln Ser Glu Ser Val Glu Phe Thr Lys Asp
1               5                   10                  15

Thr Gln Thr Gly Met Ser Gly Gln Thr Thr Pro Gln Val Glu Thr Glu
            20                  25                  30

Asp Thr Lys Glu Pro
        35

<210> SEQ ID NO 119
<211> LENGTH: 37
<212> TYPE: PRT
<213> ORGANISM: Streptococcus pyogenes

<400> SEQUENCE: 119

Gly Val Leu Met Gly Gly Gln Ser Glu Ser Val Glu Phe Thr Lys Asp
1               5                   10                  15

-continued

Thr Gln Thr Gly Met Ser Gly Gln Thr Thr Pro Gln Val Glu Thr Glu
            20                  25                  30

Asp Thr Lys Glu Pro
        35

<210> SEQ ID NO 120
<211> LENGTH: 51
<212> TYPE: PRT
<213> ORGANISM: Streptococcus pyogenes

<400> SEQUENCE: 120

Gly Val Leu Met Gly Gly Gln Ser Glu Ser Val Glu Phe Thr Lys Asp
1               5                   10                  15

Thr Gln Thr Gly Met Ser Gly Phe Ser Glu Thr Val Thr Ile Ile Glu
            20                  25                  30

Asp Thr Arg Pro Lys Leu Val Phe His Phe Asp Asn Asn Glu Pro Lys
        35                  40                  45

Val Glu Glu
    50

<210> SEQ ID NO 121
<211> LENGTH: 39
<212> TYPE: PRT
<213> ORGANISM: Streptococcus pyogenes

<400> SEQUENCE: 121

Val Ser Thr Gln Glu Asn Lys Asp Pro Ile Val Asp Ile Thr Glu Asp
1               5                   10                  15

Thr Gln Pro Gly Met Ser Gly Ser Asn Asp Ala Thr Val Val Glu Glu
            20                  25                  30

Asp Thr Thr Pro Gln Arg Pro
        35

<210> SEQ ID NO 122
<211> LENGTH: 39
<212> TYPE: PRT
<213> ORGANISM: Streptococcus pyogenes

<400> SEQUENCE: 122

Asp Val Leu Val Gly Gly Gln Ser Asp Pro Ile Asp Ile Thr Glu Asp
1               5                   10                  15

Thr Gln Pro Gly Met Ser Gly Ser Asn Asp Ala Thr Val Val Glu Glu
            20                  25                  30

Asp Thr Val Pro Lys Arg Pro
        35

<210> SEQ ID NO 123
<211> LENGTH: 82
<212> TYPE: PRT
<213> ORGANISM: Streptococcus pyogenes

<400> SEQUENCE: 123

Asp Ile Leu Val Gly Gly Gln Ser Asp Pro Ile Asp Ile Thr Glu Asp
1               5                   10                  15

Thr Gln Pro Gly Met Ser Gly Ser Asn Asp Ala Thr Val Ile Glu Glu
            20                  25                  30

Asp Thr Lys Pro Lys Arg Phe Phe His Phe Asp Asn Glu Pro Gln Ala
        35                  40                  45

Pro Glu Lys Pro Lys Glu Gln Pro Ser Leu Ser Leu Pro Gln Ala Pro

-continued

```
            50                  55                  60
Val Tyr Lys Ala Ala His His Leu Pro Ala Ser Gly Asp Lys Arg Glu
 65                  70                  75                  80

Ala Ser

<210> SEQ ID NO 124
<211> LENGTH: 36
<212> TYPE: PRT
<213> ORGANISM: Streptococcus pyogenes

<400> SEQUENCE: 124

Arg Glu Val Ile Thr Gln Gln Gly Pro Asn Leu Glu Ile Glu Glu Thr
  1               5                  10                  15

Leu Pro Leu Glu Ser Gly Ala Ser Gly Gly Thr Thr Thr Val Glu Asp
             20                  25                  30

Ser Arg Pro Val
         35

<210> SEQ ID NO 125
<211> LENGTH: 36
<212> TYPE: PRT
<213> ORGANISM: Streptococcus pyogenes

<400> SEQUENCE: 125

Tyr Lys Pro Thr Lys Gly Ser Gly Gln Val Ile Asp Ile Glu Glu Lys
  1               5                  10                  15

Leu Pro Asp Glu Gln Gly His Ser Gly Ser Thr Thr Glu Ile Glu Asp
             20                  25                  30

Ser Lys Pro Ser
         35

<210> SEQ ID NO 126
<211> LENGTH: 37
<212> TYPE: PRT
<213> ORGANISM: Streptococcus pyogenes

<400> SEQUENCE: 126

Asp Val Ile Ile Gly Gly Gln Gly Glu Val Val Asp Thr Thr Glu Asp
  1               5                  10                  15

Thr Gln Ser Gly Met Thr Gly His Ser Gly Ser Thr Thr Glu Ile Glu
             20                  25                  30

Asp Ser Lys Ser Ser
         35

<210> SEQ ID NO 127
<211> LENGTH: 47
<212> TYPE: PRT
<213> ORGANISM: Streptococcus pyogenes

<400> SEQUENCE: 127

Asp Val Ile Ile Gly Gly Gln Gly Gln Val Val Glu Thr Thr Glu Asp
  1               5                  10                  15

Thr Gln Thr Gly Met His Gly Asp Ser Gly Cys Lys Thr Glu Val Glu
             20                  25                  30

Asp Thr Lys Leu Val Gln Leu Phe His Phe Asp Asn Lys Glu Pro
             35                  40                  45

<210> SEQ ID NO 128
<211> LENGTH: 38
<212> TYPE: PRT
```

<213> ORGANISM: Streptococcus equi

<400> SEQUENCE: 128

Lys Pro Gly Gln Thr Gly Gly Gln Gly Pro Val Ile Glu Thr Thr Glu
1               5                   10                  15

Asp Thr Gln Lys Gly Met Ser Gly Gln Ser Gly Gly Thr Ile Glu Ser
            20                  25                  30

Glu Asn Thr Lys Lys Pro
        35

<210> SEQ ID NO 129
<211> LENGTH: 37
<212> TYPE: PRT
<213> ORGANISM: Streptococcus equi

<400> SEQUENCE: 129

Glu Val Met Ile Gly Gly Gln Gly Gln Thr Ile Glu Thr Thr Glu Asp
1               5                   10                  15

Thr Gln Lys Gly Met Ser Gly Gln Ser Gly Gly Thr Ile Glu Ser Glu
            20                  25                  30

Asp Thr Lys Lys Pro
        35

<210> SEQ ID NO 130
<211> LENGTH: 37
<212> TYPE: PRT
<213> ORGANISM: Streptococcus equi

<400> SEQUENCE: 130

Glu Val Met Ile Gly Gly Gln Gly Gln Ile Ile Asp Phe Ser Glu Asn
1               5                   10                  15

Thr Gln Ser Gly Met Ser Gly Gln Ser Gly Asp Thr Thr Val Ile Glu
            20                  25                  30

Asp Thr Lys Lys Ser
        35

<210> SEQ ID NO 131
<211> LENGTH: 38
<212> TYPE: PRT
<213> ORGANISM: Streptococcus equi

<400> SEQUENCE: 131

Glu Ile Ile Ile Gly Gly Gln Gly Gln Ile Ile Asp Phe Ser Glu Asp
1               5                   10                  15

Thr Gln Pro Gly Met Ser Gly Gln Ser Gly Gly Thr Thr Ile Val Glu
            20                  25                  30

Asp Thr Lys Lys Pro Thr
        35

<210> SEQ ID NO 132
<211> LENGTH: 47
<212> TYPE: PRT
<213> ORGANISM: Streptococcus dysgalactiae

<400> SEQUENCE: 132

Gly Pro Thr Glu Gly Glu Asn Asn Leu Gly Gly Gln Ser Glu Glu Ile
1               5                   10                  15

Thr Ile Thr Glu Asp Ser Gln Ser Gly Met Ser Gly Gln Asn Pro Gly
            20                  25                  30

Ser Gly Asn Glu Thr Val Val Glu Asp Thr Gln Thr Ser Gln Glu

<210> SEQ ID NO 133
<211> LENGTH: 39
<212> TYPE: PRT
<213> ORGANISM: Streptococcus dysgalactiae

<400> SEQUENCE: 133

Asp Ile Val Leu Gly Gly Pro Gly Gln Val Ile Asp Phe Thr Glu Asp
1               5                   10                  15

Ser Gln Pro Gly Met Ser Gly Asn Asn Ser His Thr Ile Thr Glu Asp
                20                  25                  30

Ser Lys Pro Ser Gln Glu Asp
            35

<210> SEQ ID NO 134
<211> LENGTH: 43
<212> TYPE: PRT
<213> ORGANISM: Streptococcus dysgalactiae

<400> SEQUENCE: 134

Glu Val Ile Ile Gly Gly Gln Gly Gln Val Ile Asp Phe Thr Glu Asp
1               5                   10                  15

Thr Gln Ser Gly Met Ser Gly Asp Asn Ser His Thr Asp Gly Thr Val
                20                  25                  30

Leu Glu Glu Asp Ser Lys Pro Ser Gln Glu Asp
            35                  40

<210> SEQ ID NO 135
<211> LENGTH: 39
<212> TYPE: PRT
<213> ORGANISM: Streptococcus dysgalactiae

<400> SEQUENCE: 135

Glu Val Ile Ile Gly Gly Gln Gly Gln Val Ile Asp Phe Thr Glu Asp
1               5                   10                  15

Thr Gln Thr Gly Met Ser Gly Ala Gly Gln Val Glu Ser Pro Thr Ile
                20                  25                  30

Thr Glu Glu Thr His Lys Pro
            35

<210> SEQ ID NO 136
<211> LENGTH: 52
<212> TYPE: PRT
<213> ORGANISM: Streptococcus dysgalactiae

<400> SEQUENCE: 136

Glu Ile Ile Met Gly Gly Gln Ser Asp Pro Ile Asp Met Val Glu Asp
1               5                   10                  15

Thr Leu Pro Gly Met Ser Gly Ser Asn Glu Ala Thr Val Val Glu Glu
                20                  25                  30

Asp Thr Arg Pro Lys Leu Gln Phe His Phe Asp Asn Glu Glu Pro Val
            35                  40                  45

Pro Ala Thr Val
    50

<210> SEQ ID NO 137
<211> LENGTH: 37
<212> TYPE: PRT
<213> ORGANISM: Streptococcus dysgalactiae

```
<400> SEQUENCE: 137

Thr Lys Arg Glu Val Ile Ile Gln Gln Gly Pro Ile Leu Gly Leu Glu
1               5                   10                  15

Glu Thr Leu Pro Thr Glu Glu His Gln Ser Gly Asp Thr Thr Ile
            20                  25                  30

Glu Asp Thr Arg Pro
        35

<210> SEQ ID NO 138
<211> LENGTH: 36
<212> TYPE: PRT
<213> ORGANISM: Streptococcus dysgalactiae

<400> SEQUENCE: 138

Asp Lys Pro Ile Thr Glu Ala Ser Gln Ser Ile Asp Phe Glu Glu Thr
1               5                   10                  15

Leu Pro Thr Glu Gln Gly Gln Ser Gly Ser Thr Thr Glu Val Glu Asp
            20                  25                  30

Thr Lys Gly Pro
        35

<210> SEQ ID NO 139
<211> LENGTH: 36
<212> TYPE: PRT
<213> ORGANISM: Streptococcus dysgalactiae

<400> SEQUENCE: 139

Glu Val Ile Ile Gly Gly Gln Gly Glu Ile Val Asp Ile Glu Glu Asn
1               5                   10                  15

Leu Pro Thr Glu Gln Gly Gln Ser Gly Ser Thr Thr Glu Val Glu Asp
            20                  25                  30

Thr Lys Gly Pro
        35

<210> SEQ ID NO 140
<211> LENGTH: 83
<212> TYPE: PRT
<213> ORGANISM: Streptococcus dysgalactiae

<400> SEQUENCE: 140

Glu Val Ile Ile Gly Gly Gln Gly Glu Val Val Asp Ile Glu Glu Ser
1               5                   10                  15

Leu Pro Thr Glu Gln Gly Gln Ser Gly Ser Thr Thr Glu Val Glu Asp
            20                  25                  30

Ser Lys Pro Lys Leu Ser Ile His Phe Asp Asn Glu Trp Pro Lys Glu
            35                  40                  45

Asp Lys Pro Gln Leu Pro Ala Val Glu Lys Pro Lys Thr Lys Glu Ser
    50                  55                  60

Leu Pro Ala Ala Gly Glu Ala Glu His Val Leu Ser Thr Ile Val Gly
65                  70                  75                  80

Ala Met Ile

<210> SEQ ID NO 141
<211> LENGTH: 39
<212> TYPE: PRT
<213> ORGANISM: Staphylococcus aureus

<400> SEQUENCE: 141

Gly Pro Ile Ile Gln Asn Asn Lys Phe Glu Tyr Lys Glu Asp Thr Ile
```

```
1               5                   10                  15
Lys Glu Thr Leu Thr Gly Gln Tyr Asp Lys Asn Leu Val Thr Thr Val
                20                  25                  30

Glu Glu Glu Tyr Asp Ser Ser
                35
```

<210> SEQ ID NO 142
<211> LENGTH: 29
<212> TYPE: PRT
<213> ORGANISM: Staphylococcus aureus

<400> SEQUENCE: 142

```
Ile Asp Phe Glu Glu Ser Thr His Glu Asn Ser Lys His His Ala Asp
1               5                   10                  15

Val Val Glu Tyr Glu Glu Asp Thr Asn Pro Gly Gly Gly
                20                  25
```

<210> SEQ ID NO 143
<211> LENGTH: 34
<212> TYPE: PRT
<213> ORGANISM: Staphylococcus aureus

<400> SEQUENCE: 143

```
Gln Val Thr Thr Glu Ser Asn Leu Val Glu Phe Asp Glu Glu Ser Thr
1               5                   10                  15

Lys Gly Ile Val Thr Gly Ala Val Ser Asp His Thr Thr Val Glu Asp
                20                  25                  30

Thr Lys
```

<210> SEQ ID NO 144
<211> LENGTH: 38
<212> TYPE: PRT
<213> ORGANISM: Staphylococcus aureus

<400> SEQUENCE: 144

```
Lys Tyr Glu Gln Gly Gly Asn Ile Val Asp Ile Asp Phe Asp Ser Val
1               5                   10                  15

Pro Gln Ile His Gly Gln Asn Lys Gly Asn Gln Ser Phe Glu Glu Asp
                20                  25                  30

Thr Glu Lys Asp Lys Pro
                35
```

<210> SEQ ID NO 145
<211> LENGTH: 38
<212> TYPE: PRT
<213> ORGANISM: Staphylococcus aureus

<400> SEQUENCE: 145

```
Lys Tyr Glu His Gly Gly Asn Ile Ile Asp Ile Asp Phe Asp Ser Val
1               5                   10                  15

Pro His Ile His Gly Phe Asn Lys His Thr Glu Ile Ile Glu Glu Asp
                20                  25                  30

Thr Asn Lys Asp Lys Pro
                35
```

<210> SEQ ID NO 146
<211> LENGTH: 36
<212> TYPE: PRT
<213> ORGANISM: Staphylococcus aureus

<400> SEQUENCE: 146

Ser Tyr Gln Phe Gly Gly His Asn Ser Val Asp Phe Glu Glu Asp Thr
1               5                   10                  15

Leu Pro Lys Val Ser Gly Gln Asn Glu Gly Gln Gln Thr Ile Glu Glu
            20                  25                  30

Asp Thr Thr Pro
        35

<210> SEQ ID NO 147
<211> LENGTH: 60
<212> TYPE: PRT
<213> ORGANISM: Borrelia burgdorferi

<400> SEQUENCE: 147

Ser Gly Glu Leu Glu Glu Pro Ile Glu Ser Asn Glu Ile Asp Leu Thr
1               5                   10                  15

Ile Asp Ser Asp Leu Arg Pro Lys Ser Ser Leu Gln Gly Ile Ala Gly
            20                  25                  30

Ser Asn Ser Ile Ser Tyr Thr Asp Glu Ile Glu Glu Asp Tyr Asp
            35                  40                  45

Gln Tyr Tyr Leu Asp Glu Tyr Asp Glu Glu Asp Glu
    50                  55                  60

<210> SEQ ID NO 148
<211> LENGTH: 21
<212> TYPE: DNA
<213> ORGANISM: Streptococcus pyogenes

<400> SEQUENCE: 148
accgaagtgt atggcaacca g                                        21

<210> SEQ ID NO 149
<211> LENGTH: 21
<212> TYPE: DNA
<213> ORGANISM: Streptococcus pyogenes

<400> SEQUENCE: 149
gtggatattg ataaaaaact g                                        21

<210> SEQ ID NO 150
<211> LENGTH: 21
<212> TYPE: DNA
<213> ORGANISM: Streptococcus pyogenes

<400> SEQUENCE: 150
ccgaacgaaa ccggctttag c                                        21

<210> SEQ ID NO 151
<211> LENGTH: 21
<212> TYPE: DNA
<213> ORGANISM: Streptococcus pyogenes

<400> SEQUENCE: 151
atggtggaaa ccgaagatac c                                        21

<210> SEQ ID NO 152
<211> LENGTH: 21
<212> TYPE: DNA
<213> ORGANISM: Streptococcus pyogenes

<400> SEQUENCE: 152
gaagtgctga tgggcggcca g                                        21

```
<210> SEQ ID NO 153
<211> LENGTH: 21
<212> TYPE: DNA
<213> ORGANISM: Streptococcus pyogenes

<400> SEQUENCE: 153
gtggaattta ccaaagatac c                                              21

<210> SEQ ID NO 154
<211> LENGTH: 21
<212> TYPE: DNA
<213> ORGANISM: Streptococcus pyogenes

<400> SEQUENCE: 154
accggcatga gcggccagac c                                              21

<210> SEQ ID NO 155
<211> LENGTH: 21
<212> TYPE: DNA
<213> ORGANISM: Streptococcus pyogenes

<400> SEQUENCE: 155
caggtggaaa ccgaagatac c                                              21

<210> SEQ ID NO 156
<211> LENGTH: 21
<212> TYPE: DNA
<213> ORGANISM: Streptococcus pyogenes

<400> SEQUENCE: 156
ggcgtgctga tgggcggcca g                                              21

<210> SEQ ID NO 157
<211> LENGTH: 21
<212> TYPE: DNA
<213> ORGANISM: Streptococcus pyogenes

<400> SEQUENCE: 157
accggcatga gcggctttag c                                              21

<210> SEQ ID NO 158
<211> LENGTH: 21
<212> TYPE: DNA
<213> ORGANISM: Streptococcus pyogenes

<400> SEQUENCE: 158
gtgaccatta ttgaagatac c                                              21

<210> SEQ ID NO 159
<211> LENGTH: 21
<212> TYPE: DNA
<213> ORGANISM: Streptococcus pyogenes

<400> SEQUENCE: 159
ctggtgtttc attttgataa c                                              21

<210> SEQ ID NO 160
<211> LENGTH: 21
<212> TYPE: DNA
<213> ORGANISM: Streptococcus pyogenes

<400> SEQUENCE: 160
```
gtgagcaccc aggaaaacaa a                                              21

<210> SEQ ID NO 161
<211> LENGTH: 21
<212> TYPE: DNA
<213> ORGANISM: Streptococcus pyogenes

<400> SEQUENCE: 161
gtggatatta ccgaagatac c                                              21

<210> SEQ ID NO 162
<211> LENGTH: 21
<212> TYPE: DNA
<213> ORGANISM: Streptococcus pyogenes

<400> SEQUENCE: 162
ccgggcatga gcggcagcaa c                                              21

<210> SEQ ID NO 163
<211> LENGTH: 21
<212> TYPE: DNA
<213> ORGANISM: Streptococcus pyogenes

<400> SEQUENCE: 163
accgtggtgg aagaagatac c                                              21

<210> SEQ ID NO 164
<211> LENGTH: 21
<212> TYPE: DNA
<213> ORGANISM: Streptococcus pyogenes

<400> SEQUENCE: 164
gatgtgctgg tgggcggcca g                                              21

<210> SEQ ID NO 165
<211> LENGTH: 21
<212> TYPE: DNA
<213> ORGANISM: Streptococcus pyogenes

<400> SEQUENCE: 165
attgatatta ccgaagatac c                                              21

<210> SEQ ID NO 166
<211> LENGTH: 21
<212> TYPE: DNA
<213> ORGANISM: Streptococcus pyogenes

<400> SEQUENCE: 166
gatattctgg tgggcggcca g                                              21

<210> SEQ ID NO 167
<211> LENGTH: 21
<212> TYPE: DNA
<213> ORGANISM: Streptococcus pyogenes

<400> SEQUENCE: 167
accgtgattg aagaagatac c                                              21

<210> SEQ ID NO 168
<211> LENGTH: 21
<212> TYPE: DNA
<213> ORGANISM: Streptococcus pyogenes

<400> SEQUENCE: 168
cgcttttttc attttgataa c                                              21

<210> SEQ ID NO 169
<211> LENGTH: 21
<212> TYPE: DNA
<213> ORGANISM: Streptococcus pyogenes

<400> SEQUENCE: 169
cgcgaagtga ttacccagca g                                              21

<210> SEQ ID NO 170
<211> LENGTH: 21
<212> TYPE: DNA
<213> ORGANISM: Streptococcus pyogenes

<400> SEQUENCE: 170
aacctggaaa ttgaagaaac c                                              21

<210> SEQ ID NO 171
<211> LENGTH: 21
<212> TYPE: DNA
<213> ORGANISM: Streptococcus pyogenes

<400> SEQUENCE: 171
ccgctggaaa gcggcgcgag c                                              21

<210> SEQ ID NO 172
<211> LENGTH: 21
<212> TYPE: DNA
<213> ORGANISM: Streptococcus pyogenes

<400> SEQUENCE: 172
accaccaccg tggaagatag c                                              21

<210> SEQ ID NO 173
<211> LENGTH: 21
<212> TYPE: DNA
<213> ORGANISM: Streptococcus pyogenes

<400> SEQUENCE: 173
tataaaccga ccaaaggcag c                                              21

<210> SEQ ID NO 174
<211> LENGTH: 21
<212> TYPE: DNA
<213> ORGANISM: Streptococcus pyogenes

<400> SEQUENCE: 174
gtgattgata ttgaagaaaa a                                              21

<210> SEQ ID NO 175
<211> LENGTH: 21
<212> TYPE: DNA
<213> ORGANISM: Streptococcus pyogenes

<400> SEQUENCE: 175
ccggatgaac agggccatag c                                              21

<210> SEQ ID NO 176
<211> LENGTH: 21
<212> TYPE: DNA
<213> ORGANISM: Streptococcus pyogenes

<400> SEQUENCE: 176
accaccgaaa ttgaagatag c                                             21

<210> SEQ ID NO 177
<211> LENGTH: 21
<212> TYPE: DNA
<213> ORGANISM: Streptococcus pyogenes

<400> SEQUENCE: 177
gatgtgatta ttggcggcca g                                             21

<210> SEQ ID NO 178
<211> LENGTH: 21
<212> TYPE: DNA
<213> ORGANISM: Streptococcus pyogenes

<400> SEQUENCE: 178
gtggatacca ccgaagatac c                                             21

<210> SEQ ID NO 179
<211> LENGTH: 21
<212> TYPE: DNA
<213> ORGANISM: Streptococcus pyogenes

<400> SEQUENCE: 179
agcggcatga ccggccatag c                                             21

<210> SEQ ID NO 180
<211> LENGTH: 21
<212> TYPE: DNA
<213> ORGANISM: Streptococcus pyogenes

<400> SEQUENCE: 180
gtggaaacca ccgaagatac c                                             21

<210> SEQ ID NO 181
<211> LENGTH: 21
<212> TYPE: DNA
<213> ORGANISM: Streptococcus pyogenes

<400> SEQUENCE: 181
accggcatgc atggcgatag c                                             21

<210> SEQ ID NO 182
<211> LENGTH: 21
<212> TYPE: DNA
<213> ORGANISM: Streptococcus pyogenes

<400> SEQUENCE: 182
aaaaccgaag tggaagatac c                                             21

<210> SEQ ID NO 183
<211> LENGTH: 21
<212> TYPE: DNA
<213> ORGANISM: Streptococcus pyogenes

<400> SEQUENCE: 183
cagctgtttc attttgataa c                                             21

<210> SEQ ID NO 184
<211> LENGTH: 21
<212> TYPE: DNA
<213> ORGANISM: Streptococcus equi

```
<400> SEQUENCE: 184
ccgggccaga ccggcggcca g                                              21

<210> SEQ ID NO 185
<211> LENGTH: 21
<212> TYPE: DNA
<213> ORGANISM: Streptococcus equi

<400> SEQUENCE: 185
attgaaacca ccgaagatac c                                              21

<210> SEQ ID NO 186
<211> LENGTH: 21
<212> TYPE: DNA
<213> ORGANISM: Streptococcus equi

<400> SEQUENCE: 186
aaaggcatga gcggccagag c                                              21

<210> SEQ ID NO 187
<211> LENGTH: 21
<212> TYPE: DNA
<213> ORGANISM: Streptococcus equi

<400> SEQUENCE: 187
accattgaaa gcgaaaacac c                                              21

<210> SEQ ID NO 188
<211> LENGTH: 21
<212> TYPE: DNA
<213> ORGANISM: Streptococcus equi

<400> SEQUENCE: 188
gaagtgatga ttggcggcca g                                              21

<210> SEQ ID NO 189
<211> LENGTH: 21
<212> TYPE: DNA
<213> ORGANISM: Streptococcus equi

<400> SEQUENCE: 189
accattgaaa gcgaagatac c                                              21

<210> SEQ ID NO 190
<211> LENGTH: 21
<212> TYPE: DNA
<213> ORGANISM: Streptococcus equi

<400> SEQUENCE: 190
attgatttta gcgaaaacac c                                              21

<210> SEQ ID NO 191
<211> LENGTH: 21
<212> TYPE: DNA
<213> ORGANISM: Streptococcus equi

<400> SEQUENCE: 191
agcggcatga gcggccagag c                                              21

<210> SEQ ID NO 192
<211> LENGTH: 21
<212> TYPE: DNA
```

```
<213> ORGANISM: Streptococcus equi

<400> SEQUENCE: 192
accaccgtga ttgaagatac c                                        21

<210> SEQ ID NO 193
<211> LENGTH: 21
<212> TYPE: DNA
<213> ORGANISM: Streptococcus equi

<400> SEQUENCE: 193
gaaattatta ttggcggcca g                                        21

<210> SEQ ID NO 194
<211> LENGTH: 21
<212> TYPE: DNA
<213> ORGANISM: Streptococcus equi

<400> SEQUENCE: 194
attgatttta gcgaagatac c                                        21

<210> SEQ ID NO 195
<211> LENGTH: 21
<212> TYPE: DNA
<213> ORGANISM: Streptococcus equi

<400> SEQUENCE: 195
ccgggcatga gcggccagag c                                        21

<210> SEQ ID NO 196
<211> LENGTH: 21
<212> TYPE: DNA
<213> ORGANISM: Streptococcus equi

<400> SEQUENCE: 196
accaccattg tggaagatac c                                        21

<210> SEQ ID NO 197
<211> LENGTH: 21
<212> TYPE: DNA
<213> ORGANISM: Streptococcus dysgalactiae

<400> SEQUENCE: 197
gaaaacaacc tgggcggcca g                                        21

<210> SEQ ID NO 198
<211> LENGTH: 21
<212> TYPE: DNA
<213> ORGANISM: Streptococcus dysgalactiae

<400> SEQUENCE: 198
attaccatta ccgaagatag c                                        21

<210> SEQ ID NO 199
<211> LENGTH: 21
<212> TYPE: DNA
<213> ORGANISM: Streptococcus dysgalactiae

<400> SEQUENCE: 199
agcggcatga gcggccagaa c                                        21

<210> SEQ ID NO 200
<211> LENGTH: 21
```

<212> TYPE: DNA
<213> ORGANISM: Streptococcus dysgalactiae

<400> SEQUENCE: 200
gaaaccgtgg tggaagatac c                                          21

<210> SEQ ID NO 201
<211> LENGTH: 21
<212> TYPE: DNA
<213> ORGANISM: Streptococcus dysgalactiae

<400> SEQUENCE: 201
gatattgtgc tgggcggccc g                                          21

<210> SEQ ID NO 202
<211> LENGTH: 21
<212> TYPE: DNA
<213> ORGANISM: Streptococcus dysgalactiae

<400> SEQUENCE: 202
attgatttta ccgaagatag c                                          21

<210> SEQ ID NO 203
<211> LENGTH: 21
<212> TYPE: DNA
<213> ORGANISM: Streptococcus dysgalactiae

<400> SEQUENCE: 203
ccgggcatga gcggcaacaa c                                          21

<210> SEQ ID NO 204
<211> LENGTH: 21
<212> TYPE: DNA
<213> ORGANISM: Streptococcus dysgalactiae

<400> SEQUENCE: 204
cataccatta ccgaagatag c                                          21

<210> SEQ ID NO 205
<211> LENGTH: 21
<212> TYPE: DNA
<213> ORGANISM: Streptococcus dysgalactiae

<400> SEQUENCE: 205
gaagtgatta ttggcggcca g                                          21

<210> SEQ ID NO 206
<211> LENGTH: 21
<212> TYPE: DNA
<213> ORGANISM: Streptococcus dysgalactiae

<400> SEQUENCE: 206
attgatttta ccgaagatac c                                          21

<210> SEQ ID NO 207
<211> LENGTH: 21
<212> TYPE: DNA
<213> ORGANISM: Streptococcus dysgalactiae

<400> SEQUENCE: 207
agcggcatga gcggcgataa c                                          21

<210> SEQ ID NO 208

-continued

<211> LENGTH: 21
<212> TYPE: DNA
<213> ORGANISM: Streptococcus dysgalactiae

<400> SEQUENCE: 208
accgtgctgg aagaagatag c                                              21

<210> SEQ ID NO 209
<211> LENGTH: 21
<212> TYPE: DNA
<213> ORGANISM: Streptococcus dysgalactiae

<400> SEQUENCE: 209
accggcatga gcggcgcggg c                                              21

<210> SEQ ID NO 210
<211> LENGTH: 21
<212> TYPE: DNA
<213> ORGANISM: Streptococcus dysgalactiae

<400> SEQUENCE: 210
ccgaccatta ccgaagaaac c                                              21

<210> SEQ ID NO 211
<211> LENGTH: 21
<212> TYPE: DNA
<213> ORGANISM: Streptococcus dysgalactiae

<400> SEQUENCE: 211
gaaattatta tgggcggcca g                                              21

<210> SEQ ID NO 212
<211> LENGTH: 21
<212> TYPE: DNA
<213> ORGANISM: Streptococcus dysgalactiae

<400> SEQUENCE: 212
attgatatgg tggaagatac c                                              21

<210> SEQ ID NO 213
<211> LENGTH: 21
<212> TYPE: DNA
<213> ORGANISM: Streptococcus dysgalactiae

<400> SEQUENCE: 213
ccgggcatga gcggcagcaa c                                              21

<210> SEQ ID NO 214
<211> LENGTH: 21
<212> TYPE: DNA
<213> ORGANISM: Streptococcus dysgalactiae

<400> SEQUENCE: 214
accgtggtgg aagaagatac c                                              21

<210> SEQ ID NO 215
<211> LENGTH: 21
<212> TYPE: DNA
<213> ORGANISM: Streptococcus dysgalactiae

<400> SEQUENCE: 215
ctgcagtttc attttgataa c                                              21

<210> SEQ ID NO 216
<211> LENGTH: 21
<212> TYPE: DNA
<213> ORGANISM: Streptococcus dysgalactiae

<400> SEQUENCE: 216
gaagtgatta ttcagcaggg c                                              21

<210> SEQ ID NO 217
<211> LENGTH: 21
<212> TYPE: DNA
<213> ORGANISM: Streptococcus dysgalactiae

<400> SEQUENCE: 217
attctgggcc tggaagaaac c                                              21

<210> SEQ ID NO 218
<211> LENGTH: 21
<212> TYPE: DNA
<213> ORGANISM: Streptococcus dysgalactiae

<400> SEQUENCE: 218
ccgaccgaag aacatcagag c                                              21

<210> SEQ ID NO 219
<211> LENGTH: 21
<212> TYPE: DNA
<213> ORGANISM: Streptococcus dysgalactiae

<400> SEQUENCE: 219
accaccacca ttgaagatac c                                              21

<210> SEQ ID NO 220
<211> LENGTH: 21
<212> TYPE: DNA
<213> ORGANISM: Streptococcus dysgalactiae

<400> SEQUENCE: 220
gataaaccga ttaccgaagc g                                              21

<210> SEQ ID NO 221
<211> LENGTH: 21
<212> TYPE: DNA
<213> ORGANISM: Streptococcus dysgalactiae

<400> SEQUENCE: 221
agcattgatt ttgaagaaac c                                              21

<210> SEQ ID NO 222
<211> LENGTH: 21
<212> TYPE: DNA
<213> ORGANISM: Streptococcus dysgalactiae

<400> SEQUENCE: 222
ccgaccgaac agggccagag c                                              21

<210> SEQ ID NO 223
<211> LENGTH: 21
<212> TYPE: DNA
<213> ORGANISM: Streptococcus dysgalactiae

<400> SEQUENCE: 223
accaccgaag tggaagatac c                                              21

```
<210> SEQ ID NO 224
<211> LENGTH: 21
<212> TYPE: DNA
<213> ORGANISM: Streptococcus dysgalactiae

<400> SEQUENCE: 224
attgtggata ttgaagaaaa c                                              21

<210> SEQ ID NO 225
<211> LENGTH: 21
<212> TYPE: DNA
<213> ORGANISM: Streptococcus dysgalactiae

<400> SEQUENCE: 225
gtggtggata ttgaagaaag c                                              21

<210> SEQ ID NO 226
<211> LENGTH: 21
<212> TYPE: DNA
<213> ORGANISM: Streptococcus dysgalactiae

<400> SEQUENCE: 226
accaccgaag tggaagatag c                                              21

<210> SEQ ID NO 227
<211> LENGTH: 21
<212> TYPE: DNA
<213> ORGANISM: Streptococcus dysgalactiae

<400> SEQUENCE: 227
ctgagcattc attttgataa c                                              21

<210> SEQ ID NO 228
<211> LENGTH: 21
<212> TYPE: DNA
<213> ORGANISM: Staphylococcus aureus

<400> SEQUENCE: 228
ggtccaatta ttcaaaataa t                                              21

<210> SEQ ID NO 229
<211> LENGTH: 21
<212> TYPE: DNA
<213> ORGANISM: Staphylococcus aureus

<400> SEQUENCE: 229
tttgaatata aagaagatac a                                              21

<210> SEQ ID NO 230
<211> LENGTH: 21
<212> TYPE: DNA
<213> ORGANISM: Staphylococcus aureus

<400> SEQUENCE: 230
gaaacattaa caggtcaata t                                              21

<210> SEQ ID NO 231
<211> LENGTH: 21
<212> TYPE: DNA
<213> ORGANISM: Staphylococcus aureus

<400> SEQUENCE: 231
acaacagttg aagaagaata t                                              21
```

```
<210> SEQ ID NO 232
<211> LENGTH: 18
<212> TYPE: DNA
<213> ORGANISM: Staphylococcus aureus

<400> SEQUENCE: 232
attgattttg aagaatca                                                   18

<210> SEQ ID NO 233
<211> LENGTH: 21
<212> TYPE: DNA
<213> ORGANISM: Staphylococcus aureus

<400> SEQUENCE: 233
gaaaattcaa aacatcatgc a                                               21

<210> SEQ ID NO 234
<211> LENGTH: 21
<212> TYPE: DNA
<213> ORGANISM: Staphylococcus aureus

<400> SEQUENCE: 234
gttgaatatg aagaagatac a                                               21

<210> SEQ ID NO 235
<211> LENGTH: 21
<212> TYPE: DNA
<213> ORGANISM: Staphylococcus aureus

<400> SEQUENCE: 235
caagttacaa cagaatcaaa t                                               21

<210> SEQ ID NO 236
<211> LENGTH: 21
<212> TYPE: DNA
<213> ORGANISM: Staphylococcus aureus

<400> SEQUENCE: 236
gttgaatttg atgaagaatc a                                               21

<210> SEQ ID NO 237
<211> LENGTH: 21
<212> TYPE: DNA
<213> ORGANISM: Staphylococcus aureus

<400> SEQUENCE: 237
ggtattgtta caggtgcagt t                                               21

<210> SEQ ID NO 238
<211> LENGTH: 21
<212> TYPE: DNA
<213> ORGANISM: Staphylococcus aureus

<400> SEQUENCE: 238
catacaacag ttgaagatac a                                               21

<210> SEQ ID NO 239
<211> LENGTH: 21
<212> TYPE: DNA
<213> ORGANISM: Staphylococcus aureus

<400> SEQUENCE: 239
```

```
aaatatgaac aaggtggtaa t                                              21

<210> SEQ ID NO 240
<211> LENGTH: 21
<212> TYPE: DNA
<213> ORGANISM: Staphylococcus aureus

<400> SEQUENCE: 240
gttgatattg attttgattc a                                              21

<210> SEQ ID NO 241
<211> LENGTH: 21
<212> TYPE: DNA
<213> ORGANISM: Staphylococcus aureus

<400> SEQUENCE: 241
ccacaaattc atggtcaaaa t                                              21

<210> SEQ ID NO 242
<211> LENGTH: 21
<212> TYPE: DNA
<213> ORGANISM: Staphylococcus aureus

<400> SEQUENCE: 242
caatcatttg aagaagatac a                                              21

<210> SEQ ID NO 243
<211> LENGTH: 21
<212> TYPE: DNA
<213> ORGANISM: Staphylococcus aureus

<400> SEQUENCE: 243
aaatatgaac atggtggtaa t                                              21

<210> SEQ ID NO 244
<211> LENGTH: 21
<212> TYPE: DNA
<213> ORGANISM: Staphylococcus aureus

<400> SEQUENCE: 244
attgatattg attttgattc a                                              21

<210> SEQ ID NO 245
<211> LENGTH: 21
<212> TYPE: DNA
<213> ORGANISM: Staphylococcus aureus

<400> SEQUENCE: 245
ccacatattc atggttttaa t                                              21

<210> SEQ ID NO 246
<211> LENGTH: 21
<212> TYPE: DNA
<213> ORGANISM: Staphylococcus aureus

<400> SEQUENCE: 246
gaaattattg aagaagatac a                                              21

<210> SEQ ID NO 247
<211> LENGTH: 21
<212> TYPE: DNA
<213> ORGANISM: Staphylococcus aureus

<400> SEQUENCE: 247
```

```
tcatatcaat ttggtggtca t                                              21

<210> SEQ ID NO 248
<211> LENGTH: 21
<212> TYPE: DNA
<213> ORGANISM: Staphylococcus aureus

<400> SEQUENCE: 248
gttgattttg aagaagatac a                                              21

<210> SEQ ID NO 249
<211> LENGTH: 21
<212> TYPE: DNA
<213> ORGANISM: Staphylococcus aureus

<400> SEQUENCE: 249
ccaaaagttt caggtcaaaa t                                              21

<210> SEQ ID NO 250
<211> LENGTH: 21
<212> TYPE: DNA
<213> ORGANISM: Staphylococcus aureus

<400> SEQUENCE: 250
caaacaattg aagaagatac a                                              21

<210> SEQ ID NO 251
<211> LENGTH: 18
<212> TYPE: DNA
<213> ORGANISM: Borrelia burgdorferi

<400> SEQUENCE: 251
gaaccgattg aaagcaac                                                  18

<210> SEQ ID NO 252
<211> LENGTH: 21
<212> TYPE: DNA
<213> ORGANISM: Borrelia burgdorferi

<400> SEQUENCE: 252
attgatctga ccattgatag c                                              21

<210> SEQ ID NO 253
<211> LENGTH: 21
<212> TYPE: DNA
<213> ORGANISM: Borrelia burgdorferi

<400> SEQUENCE: 253
cagggcattg cgggcagcaa c                                              21

<210> SEQ ID NO 254
<211> LENGTH: 21
<212> TYPE: DNA
<213> ORGANISM: Borrelia burgdorferi

<400> SEQUENCE: 254
gaaattgaag aagaagatta t                                              21

<210> SEQ ID NO 255
<211> LENGTH: 33
<212> TYPE: DNA
<213> ORGANISM: Mycobacterium tuberculosis
```

<400> SEQUENCE: 255
ttcgagtggt acgaccagtc gggcctgtcg gtg				33

<210> SEQ ID NO 256
<211> LENGTH: 33
<212> TYPE: DNA
<213> ORGANISM: Mycobacterium tuberculosis

<400> SEQUENCE: 256
ttcgagtggt actaccagtc gggcctgtcg atc				33

<210> SEQ ID NO 257
<211> LENGTH: 33
<212> TYPE: DNA
<213> ORGANISM: Mycobacterium tuberculosis

<400> SEQUENCE: 257
ttcgaggagt actaccagtc gggcctgtcg gtg				33

<210> SEQ ID NO 258
<211> LENGTH: 330
<212> TYPE: DNA
<213> ORGANISM: Streptococcus equi subsp. equi

<400> SEQUENCE: 258
ctgccggaaa aaggcctgaa cggcgaaaac cagaaagaac cggaacaggg cgaacgcggc		60 gaagcgggcc cgccgctgag cggcctgagc ggcaacaacc agggccgccc gagcctgccg		120 ggcctgaacg gcgaaaacca gaaagaaccg gaacagggcg aacgcggcga agcgggcccg		180 ccgagcaccc cgaacctgga aggcaacaac cgcaaaaacc cgctgaaagg cctggatggc		240 gaaaacaaac cgaaagaaga tctggatggc aaaggcctga gcggcgaaaa cgatgaaagc		300 ccgaaactga aagatgaaca tccgtataac					330

<210> SEQ ID NO 259
<211> LENGTH: 330
<212> TYPE: DNA
<213> ORGANISM: Streptococcus equi subsp. zooepidemicus

<400> SEQUENCE: 259
ctgccggaaa aaggcctgaa cggcgaaaac cagaaagaac cggaacaggg cgaacgcggc		60 gaagcgggcc cgccgagcac cccgaacctg gaaggcaaca accgcaaaaa cccgctgaaa		120 ggcctggatg gcgaaaacaa accgaaagaa gatctggatg gcaaaggcct gagcggcgaa		180 aacgatgaaa gcccgaaact gaaagatgaa catccgtata accatggccg ccgcgatggc		240 tatcgcgtgg gctatgaaga tggctatggc ggcaaaaaac ataaaggcga ttatccgaaa		300 cgctttgatg aaagcagccc gaaagaatat					330

<210> SEQ ID NO 260
<211> LENGTH: 60
<212> TYPE: DNA
<213> ORGANISM: Homo sapiens

<400> SEQUENCE: 260
aggttcaagc aggacggcgg ctggagccac tggagcccct ggagcagctg cagcgtgacc		60

<210> SEQ ID NO 261
<211> LENGTH: 120
<212> TYPE: DNA
<213> ORGANISM: Homo sapiens

<400> SEQUENCE: 261
ggccccgccg gcgcccccgg caccccccggc ccccagggca tcgccggcca gaggggcgtg     60
gtgggcctgc ccggccagag gggcgagagg ggcttccccg gcctgcccgg ccccagcggc    120

<210> SEQ ID NO 262
<211> LENGTH: 36
<212> TYPE: DNA
<213> ORGANISM: Homo sapiens

<400> SEQUENCE: 262
accctgcagc ccgtgtacga gtacatggtg ggcgtg                                36

<210> SEQ ID NO 263
<211> LENGTH: 45
<212> TYPE: DNA
<213> ORGANISM: Homo sapiens

<400> SEQUENCE: 263
accggcctgc ccgtgggcgt gggctacgtg gtgaccgtgc tgacc                      45

<210> SEQ ID NO 264
<211> LENGTH: 108
<212> TYPE: DNA
<213> ORGANISM: Streptococcus pyogenes

<400> SEQUENCE: 264
accgaagtgt atggcaacca gcagaacccg gtggatattg ataaaaaact gccgaacgaa     60
accggcttta gcggcaacat ggtggaaacc gaagatacca agaaccg                  108

<210> SEQ ID NO 265
<211> LENGTH: 111
<212> TYPE: DNA
<213> ORGANISM: Streptococcus pyogenes

<400> SEQUENCE: 265
gaagtgctga tgggcggcca gagcgaaagc gtggaattta ccaaagatac ccagaccggc     60
atgagcggcc agaccacccc gcaggtggaa accgaagata ccaaagaacc g             111

<210> SEQ ID NO 266
<211> LENGTH: 111
<212> TYPE: DNA
<213> ORGANISM: Streptococcus pyogenes

<400> SEQUENCE: 266
ggcgtgctga tgggcggcca gagcgaaagc gtggaattta ccaaagatac ccagaccggc     60
atgagcggcc agaccacccc gcaggtggaa accgaagata ccaaagaacc g             111

<210> SEQ ID NO 267
<211> LENGTH: 153
<212> TYPE: DNA
<213> ORGANISM: Streptococcus pyogenes

<400> SEQUENCE: 267
ggcgtgctga tgggcggcca gagcgaaagc gtggaattta ccaaagatac ccagaccggc     60
atgagcggct ttagcgaaac cgtgaccatt attgaagata cccgcccgaa actggtgttt    120
cattttgata caacgaacc gaaagtggaa gaa                                  153

<210> SEQ ID NO 268

```
<211> LENGTH: 117
<212> TYPE: DNA
<213> ORGANISM: Streptococcus pyogenes

<400> SEQUENCE: 268
gtgagcaccc aggaaaacaa agatccgatt gtggatatta ccgaagatac ccagccgggc    60
atgagcggca gcaacgatgc gaccgtggtg aagaagata ccaccccgca gcgcccg      117

<210> SEQ ID NO 269
<211> LENGTH: 117
<212> TYPE: DNA
<213> ORGANISM: Streptococcus pyogenes

<400> SEQUENCE: 269
gatgtgctgg tgggcggcca gagcgatccg attgatatta ccgaagatac ccagccgggc    60
atgagcggca gcaacgatgc gaccgtggtg aagaagata ccgtgccgaa acgcccg      117

<210> SEQ ID NO 270
<211> LENGTH: 246
<212> TYPE: DNA
<213> ORGANISM: Streptococcus pyogenes

<400> SEQUENCE: 270
gatattctgg tgggcggcca gagcgatccg attgatatta ccgaagatac ccagccgggc    60
atgagcggca gcaacgatgc gaccgtgatt gaagaagata ccaaaccgaa acgctttttt   120
cattttgata cgaaccgca ggcgccggaa aaaccgaaag aacagccgag cctgagcctg    180
ccgcaggcgc cggtgtataa agcggcgcat catctgccgg cgagcggcga taaacgcgaa    240
gcgagc                                                              246

<210> SEQ ID NO 271
<211> LENGTH: 108
<212> TYPE: DNA
<213> ORGANISM: Streptococcus pyogenes

<400> SEQUENCE: 271
cgcgaagtga ttacccagca gggcccgaac ctggaaattg aagaaccct gccgctggaa     60 agcggcgcga gcggcggcac caccaccgtg aagatagcc gcccggtg              108

<210> SEQ ID NO 272
<211> LENGTH: 108
<212> TYPE: DNA
<213> ORGANISM: Streptococcus pyogenes

<400> SEQUENCE: 272
tataaaccga ccaaaggcag cggccaggtg attgatattg aagaaaaact gccggatgaa     60
cagggccata gcggcagcac caccgaaatt gaagatagca accgagc              108

<210> SEQ ID NO 273
<211> LENGTH: 111
<212> TYPE: DNA
<213> ORGANISM: Streptococcus pyogenes

<400> SEQUENCE: 273
gatgtgatta ttggcggcca gggcgaagtg gtggatacca ccgaagatac ccagagcggc     60
atgaccggcc atagcggcag caccaccgaa attgaagata gcaaaagcag c            111

<210> SEQ ID NO 274
<211> LENGTH: 141
```

```
<212> TYPE: DNA
<213> ORGANISM: Streptococcus pyogenes

<400> SEQUENCE: 274
gatgtgatta ttggcggcca gggccaggtg gtggaaacca ccgaagatac ccagaccggc      60
atgcatggcg atagcggctg caaaaccgaa gtggaagata ccaaactggt gcagctgttt     120
cattttgata caaagaacc g                                                141

<210> SEQ ID NO 275
<211> LENGTH: 114
<212> TYPE: DNA
<213> ORGANISM: Streptococcus equi

<400> SEQUENCE: 275
aaaccgggcc agaccggcgg ccagggcccg gtgattgaaa ccaccgaaga tacccagaaa      60
ggcatgagcg gccagagcgg cggcaccatt gaaagcgaaa acaccaaaaa accg            114

<210> SEQ ID NO 276
<211> LENGTH: 111
<212> TYPE: DNA
<213> ORGANISM: Streptococcus equi

<400> SEQUENCE: 276
gaagtgatga ttggcggcca gggccagacc attgaaacca ccgaagatac ccagaaaggc      60
atgagcggcc agagcggcgg caccattgaa agcgaagata ccaaaaaacc g               111

<210> SEQ ID NO 277
<211> LENGTH: 111
<212> TYPE: DNA
<213> ORGANISM: Streptococcus equi

<400> SEQUENCE: 277
gaagtgatga ttggcggcca gggccagatt attgatttta gcgaaaacac ccagagcggc      60
atgagcggcc agagcggcga taccaccgtg attgaagata ccaaaaaaag c               111

<210> SEQ ID NO 278
<211> LENGTH: 114
<212> TYPE: DNA
<213> ORGANISM: Streptococcus equi

<400> SEQUENCE: 278
gaaattatta ttggcggcca gggccagatt attgatttta gcgaagatac ccagccgggc      60
atgagcggcc agagcggcgg caccaccatt gtggaagata ccaaaaaacc gacc            114

<210> SEQ ID NO 279
<211> LENGTH: 141
<212> TYPE: DNA
<213> ORGANISM: Streptococcus dysgalactiae

<400> SEQUENCE: 279
ggtccaacag aaggtgaaaa taatttaggt ggtcaatcag aagaaattac aattacagaa      60
gattcacaat caggtatgtc aggtcaaaat ccaggttcag gtaatgaaac agttgttgaa     120
gatacacaaa catcacaaga a                                               141

<210> SEQ ID NO 280
<211> LENGTH: 117
<212> TYPE: DNA
<213> ORGANISM: Streptococcus dysgalactiae
```

<400> SEQUENCE: 280
gatattgttt taggtggtcc aggtcaagtt attgatttta cagaagattc acaaccaggt    60
atgtcaggta ataattcaca tacaattaca gaagattcaa accatcaca agaagat       117

<210> SEQ ID NO 281
<211> LENGTH: 129
<212> TYPE: DNA
<213> ORGANISM: Streptococcus dysgalactiae

<400> SEQUENCE: 281
gaagttatta ttggtggtca aggtcaagtt attgatttta cagaagatac acaatcaggt    60
atgtcaggtg ataattcaca tacagatggt acagtttag aagaagattc aaaaccatca   120
caagaagat                                                          129

<210> SEQ ID NO 282
<211> LENGTH: 117
<212> TYPE: DNA
<213> ORGANISM: Streptococcus dysgalactiae

<400> SEQUENCE: 282
gaagttatta ttggtggtca aggtcaagtt attgatttta cagaagatac acaaacaggt    60
atgtcaggtg caggtcaagt tgaatcacca acaattacag aagaaacaca taaacca     117

<210> SEQ ID NO 283
<211> LENGTH: 156
<212> TYPE: DNA
<213> ORGANISM: Streptococcus dysgalactiae

<400> SEQUENCE: 283
gaaattatta tgggtggtca atcagatcca attgatatgg ttgaagatac attaccaggt    60
atgtcaggtt caaatgaagc aacagttgtt gaagaagata caagaccaaa attacaattt   120
cattttgata atgaagaacc agttccagca acagtt                             156

<210> SEQ ID NO 284
<211> LENGTH: 111
<212> TYPE: DNA
<213> ORGANISM: Streptococcus dysgalactiae

<400> SEQUENCE: 284
acaaaaagag aagttattat tcaacaaggt ccaattttag gtttagaaga acattacca    60 acagaagaac atcaatcagg tgatacaaca acaattgaag atacaagacc a            111

<210> SEQ ID NO 285
<211> LENGTH: 108
<212> TYPE: DNA
<213> ORGANISM: Streptococcus dysgalactiae

<400> SEQUENCE: 285
gataaaccaa ttacagaagc atcacaatca attgattttg aagaaacatt accaacagaa    60
caaggtcaat caggttcaac aacagaagtt gaagatacaa aaggtcca                108

<210> SEQ ID NO 286
<211> LENGTH: 108
<212> TYPE: DNA
<213> ORGANISM: Streptococcus dysgalactiae

<400> SEQUENCE: 286
gaagttatta ttggtggtca aggtgaaatt gttgatattg aagaaatttt accaacagaa    60
caaggtcaat caggttcaac aacagaagtt gaagatacaa aaggtcca       108

<210> SEQ ID NO 287
<211> LENGTH: 249
<212> TYPE: DNA
<213> ORGANISM: Streptococcus dysgalactiae

<400> SEQUENCE: 287
gaagttatta ttggtggtca aggtgaagtt gttgatattg aagaatcatt accaacagaa       60
caaggtcaat caggttcaac aacagaagtt gaagattcaa accaaaaatt atcaattcat      120
tttgataatg aatggccaaa agaagataaa ccacaattac cagcagttga aaaaccaaaa      180
acaaaagaat cattaccagc agcaggtgaa gcagaacatg ttttatcaac aattgttggt      240
gcaatgatt                                                               249

<210> SEQ ID NO 288
<211> LENGTH: 117
<212> TYPE: DNA
<213> ORGANISM: Staphylococcus aureus

<400> SEQUENCE: 288
ggtccaatta ttcaaaataa taaatttgaa tataaagaag atacaattaa agaaacatta       60
acaggtcaat atgataaaaa tttagttaca acagttgaag aagaatatga ttcatca         117

<210> SEQ ID NO 289
<211> LENGTH: 87
<212> TYPE: DNA
<213> ORGANISM: Staphylococcus aureus

<400> SEQUENCE: 289
attgattttg aagaatcaac acatgaaaat tcaaacatc atgcagatgt tgttgaatat       60
gaagaagata caaatccagg tggtggt                                           87

<210> SEQ ID NO 290
<211> LENGTH: 102
<212> TYPE: DNA
<213> ORGANISM: Staphylococcus aureus

<400> SEQUENCE: 290
caagttacaa cagaatcaaa tttagttgaa tttgatgaag aatcaacaaa aggtattgtt       60
acaggtgcag tttcagatca tacaacagtt gaagatacaa aa                         102

<210> SEQ ID NO 291
<211> LENGTH: 114
<212> TYPE: DNA
<213> ORGANISM: Staphylococcus aureus

<400> SEQUENCE: 291
aaatatgaac aaggtggtaa tattgttgat attgattttg attcagttcc acaaattcat       60
ggtcaaaata aaggtaatca atcatttgaa gaagatacag aaaaagataa acca            114

<210> SEQ ID NO 292
<211> LENGTH: 114
<212> TYPE: DNA
<213> ORGANISM: Staphylococcus aureus

<400> SEQUENCE: 292
aaatatgaac atggtggtaa tattattgat attgattttg attcagttcc acatattcat       60 ggtttaata aacatacaga aattattgaa gaagatacaa ataaagataa acca 114

<210> SEQ ID NO 293
<211> LENGTH: 108
<212> TYPE: DNA
<213> ORGANISM: Staphylococcus aureus

<400> SEQUENCE: 293
tcatatcaat ttggtggtca taattcagtt gattttgaag aagatacatt accaaaagtt 60
tcaggtcaaa atgaaggtca acaaacaatt gaagaagata caacacca 108

<210> SEQ ID NO 294
<211> LENGTH: 180
<212> TYPE: DNA
<213> ORGANISM: Borrelia burgdorferi

<400> SEQUENCE: 294
agcggcgaac tggaagaacc gattgaaagc aacgaaattg atctgaccat tgatagcgat 60
ctgcgcccga aaagcagcct gcagggcatt gcgggcagca acagcattag ctataccgat 120
gaaattgaag aagaagatta tgatcagtat tatctggatg aatatgatga agaagatgaa 180

<210> SEQ ID NO 295
<211> LENGTH: 38
<212> TYPE: PRT
<213> ORGANISM: Staphylococcus aureus

<400> SEQUENCE: 295

Cys Gly Gly Gly Gln Val Thr Thr Glu Ser Asn Leu Val Glu Phe Asp
1               5                   10                  15

Glu Glu Ser Thr Lys Gly Ile Val Thr Gly Ala Val Ser Asp His Thr
            20                  25                  30

Thr Val Glu Asp Thr Lys
        35

<210> SEQ ID NO 296
<211> LENGTH: 38
<212> TYPE: PRT
<213> ORGANISM: Artificial Sequence
<220> FEATURE:
<223> OTHER INFORMATION: Synthetic

<400> SEQUENCE: 296

Cys Gly Ser Glu Gln Glu Asp Leu Thr Gly Thr Lys Val Asp Phe Gly
1               5                   10                  15

Glu Thr Ile Val Val Asn Glu Ala Thr Glu Thr Val Thr Ser Gly Ser
            20                  25                  30

Thr His Gly Thr Lys Val
        35

<210> SEQ ID NO 297
<211> LENGTH: 21
<212> TYPE: PRT
<213> ORGANISM: Artificial Sequence
<220> FEATURE:
<223> OTHER INFORMATION: Synthetic

<400> SEQUENCE: 297

Met Glu Val Gly Trp Tyr Arg Ser Pro Phe Ser Arg Val Val His Leu
1               5                   10                  15

Tyr Arg Asn Gly Lys
            20

<210> SEQ ID NO 298
<211> LENGTH: 13
<212> TYPE: PRT
<213> ORGANISM: Artificial Sequence
<220> FEATURE:
<223> OTHER INFORMATION: Synthetic

<400> SEQUENCE: 298

Cys His Cys Leu Gly Lys Trp Leu Gly His Pro Asp Lys
1               5                   10

<210> SEQ ID NO 299
<211> LENGTH: 14
<212> TYPE: PRT
<213> ORGANISM: Artificial Sequence
<220> FEATURE:
<223> OTHER INFORMATION: Synthetic

<400> SEQUENCE: 299

Phe Asn Thr Trp Thr Thr Cys Gln Ser Ile Ala Phe Pro Ser
1               5                   10

<210> SEQ ID NO 300
<211> LENGTH: 15
<212> TYPE: PRT
<213> ORGANISM: Artificial Sequence
<220> FEATURE:
<223> OTHER INFORMATION: Synthetic

<400> SEQUENCE: 300

Lys Glu Lys Pro Gln Ser Thr Ile Ser Gly Leu Leu Gly Pro Thr
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Synthetic

<400> SEQUENCE: 301

Ser Ala Cys Arg Ala Trp Ala Tyr Tyr Ser Ala Val Asn Pro Glu
1               5                   10                  15

<210> SEQ ID NO 302
<211> LENGTH: 20
<212> TYPE: PRT
<213> ORGANISM: Artificial Sequence
<220> FEATURE:
<223> OTHER INFORMATION: Synthetic

<400> SEQUENCE: 302

Phe Phe Asn Pro Pro Ile Ile Ser Arg Phe Ile Arg Val Ile Pro Lys
1               5                   10                  15

Thr Trp Asn Gln
            20